(12) United States Patent
D'Andrea

(10) Patent No.: US 8,541,192 B2
(45) Date of Patent: Sep. 24, 2013

(54) METHODS TO IDENTIFY USP1 DEUBIQUITINATING ENZYME COMPLEX INHIBITORS

(75) Inventor: Alan D. D'Andrea, Winchester, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 377 days.

(21) Appl. No.: 12/835,559

(22) Filed: Jul. 13, 2010

(65) Prior Publication Data

US 2010/0330599 A1 Dec. 30, 2010

Related U.S. Application Data

(63) Continuation of application No. 11/820,674, filed on Jun. 20, 2007, now Pat. No. 7,754,463.

(60) Provisional application No. 60/815,483, filed on Jun. 20, 2006.

(51) Int. Cl.
*C12Q 1/37* (2006.01)

(52) U.S. Cl.
USPC .......................................................... 435/23

(58) Field of Classification Search
None
See application file for complete search history.

(56) References Cited

U.S. PATENT DOCUMENTS

| | | | |
|---|---|---|---|
| 5,217,964 | A | 6/1993 | Edwards et al. |
| 5,354,782 | A | 10/1994 | Edwards et al. |
| 5,434,145 | A | 7/1995 | Edwards et al. |
| 6,114,394 | A | 9/2000 | Edwards et al. |
| 7,041,994 | B2 | 5/2006 | Hayashi et al. |
| 7,754,463 | B2 | 7/2010 | D'Andrea |
| 2004/0053324 | A1* | 3/2004 | Wong et al. ............ 435/7.1 |

FOREIGN PATENT DOCUMENTS

| | | |
|---|---|---|
| WO | WO 97/21684 A1 | 6/1997 |
| WO | WO 97/21710 A1 | 6/1997 |

OTHER PUBLICATIONS

Liu et al, Chem Biol. Sep. 2003;10(9):837-46. Discovery of inhibitors that elucidate the role of UCH-L1 activity in the H1299 lung cancer cell line.*
Wishart et al, A single mutation converts a novel phosphotyrosine binding domain into a dual-specificity phosphatase. J Biol Chem. Nov. 10, 1995;270(45):26782-26785.*
Whisstock et al, Prediction of protein function from protein sequence and structure. Q Rev Biophys. Aug. 2003;36(3):307-40. Review.*
Cohen et al., CD4+ T-cells from mice immunized to syngeneic sarcomas recognize distinct, non-shared tumor antigens. Cancer Res. Feb. 15, 1994;54(4):1055-8.
Cohn et al., A UAF1-containing multisubunit protein complex regulates the Fanconi anemia pathway. Mol Cell. Dec. 14, 2007;28(5):786-97.

Cohn et al., UAF1 is a subunit of multiple deubiquitinating enzyme complexes. J Biol Chem. Feb. 20, 2009;284(8):5343-51. Epub Dec. 15, 2008.
D'Andrea et al., The Fanconi Anemia and Breast Cancer Susceptibility Pathways. N. Engl J Med. May 20, 2010;362(20):1909-19.
Hoege et al., RAD6-dependent DNA repair is linked to modification of PCNA by ubiquitin and SUMO. Nature. Sep. 12, 2002;419(6903):135-41.
Kee et al., WDR20 regulates activity of the USP12 x UAF1 deubiquitinating enzyme complex. J Biol Chem. Apr. 9, 2010;285(15):11252-7. Epub Feb. 10, 2010.
Kennedy et al., The Fanconi Anemia/BRCA pathway: new faces in the crowd. Genes Dev. Dec. 15, 2005;19(24):2925-40.
Kim et al., Inactivation of murine Usp 1 results in genomic instability and a Fanconi anemia phenotype. Dev Cell. Feb. 2009;16(2):314-20.
Nakatani et al., Immunoaffinity purification of mammalian protein complexes. Methods Enzymol. 2003;370:430-44.
Nijman et al., A genomic and functional inventory of deubiquitinating enzymes. Cell. Dec. 2, 2005;123(5):773-86.
Park et al., Herpesviral protein targets a cellular WD repeat endosomal protein to downregulate T lymphocyte receptor expression. Immunity. Aug. 2002;17(2):221-33.
Pickart et al., Ubiquitin: structures, functions, mechanisms. Biochim Biophys Acta. Nov. 29, 2004;1695(1-3):55-72.
Sondhi et al., A convenient, solvent free and high yielding synthesis of bicyclo-heterocyclic compounds. Letts Org Chem. 2008;5:51-54.
Yang et al., Targeted disruption of the murine Fanconi anemia gene, Fancg/Xrcc9. Blood. Dec. 1, 2001;98(12):3435-40.
Chen et al., Sequence and expression in *Escherichia coli* of the 40-kDa subunit of activator 1 (replication factor C) of HeLa cells. Proc Natl Acad Sci U S A. Apr. 1, 1992;89(7):2516-20.
Dang et al., Kinetic and mechanistic studies on the hydrolysis of ubiquitin C-terminal 7-amido-4-methylcoumarin by deubiquitinating enzymes. Biochemistry. Feb. 17, 1998;37(7):1868-79.
Fields et al., A novel genetic system to detect protein-protein interactions. Nature. Jul. 20, 1989;340(6230):245-6.
Fujiwara et al., Identification and chromosomal assignment of USP1, a novel gene encoding a human ubiquitin-specific protease. Genomics. Nov. 15, 1998;54(1):155-8.
Gayle et al., Identification of regions in interleukin-1 alpha important for activity. J Biol Chem. Oct. 15, 1993;268(29):22105-11.
Gavin et al., Functional organization of the yeast proteome by systematic analysis of protein complexes. Nature. Jan. 10, 2002;415(6868):141-7.
Gavin et al., Proteome survey reveals modularity of the yeast cell machinery. Nature. Mar. 30, 2006;440(7084):631-6. Epub Jan. 22, 2006.
Genbank Submission; NIH/NCBI, Accession No. NM_182649; Masuo et al.; Nov. 1, 2009.
Hershko et al., Ubiquitin-aldehyde: a general inhibitor of ubiquitin-recycling processes. Proc Natl Acad Sci U S A. Apr. 1987;84(7):1829-33.

(Continued)

*Primary Examiner* — Sheridan Swope
(74) *Attorney, Agent, or Firm* — Wolf, Greenfield & Sacks, P.C.

(57) ABSTRACT

The invention provides methods used to identify new inhibitors of USP1 deubiquitinase. The inhibitors can be identified by contacting isolated USP1 with a test compound in the presence of monoubiquitinated proliferating cell nuclear antigen (PCNA), monoubiquitinated human Fanconi anemia group D2 (FANCD2), or ubiquitin-7-amido-4-methylcoumarin, and detecting the deubiquitination of said PCNA, FANCD2, or ubiquitin-7-amido-4-methylcoumarin using an antibody or fluorescence, wherein a decrease in the deubiquitination of said PCNA, FANCD2, or ubiquitin-7-amido-4-methylcoumarin in the presence of the test compound relative to the absence of the test compound identifies said test compound as an inhibitor of USP1 deubiquitinase.

4 Claims, 23 Drawing Sheets

(56) References Cited

OTHER PUBLICATIONS

Ho et al., Systematic identification of protein complexes in *Saccharomyces cerevisiae* by mass spectrometry. Nature. Jan. 10, 2002;415(6868):180-3.

Hu et al., Crystal structure of a UBP-family deubiquitinating enzyme in isolation and in complex with ubiquitin aldehyde. Cell. Dec. 27, 2002;111(7):1041-54.

Huang et al., HAUSP hunting the Fox(O). Nat Cell Biol. Oct. 2006;8(10):1043-5.

Huang et al., Regulation of DNA repair by ubiquitylation. Nat Rev Mol Cell Biol. May 2006;7(5):323-34.

Huang et al., Regulation of monoubiquitinated PCNA by DUB autocleavage. Nat Cell Biol. Apr. 2006;8(4):339-47. Epub Mar. 12, 2006.

Ingvarsdottir et al., H2B ubiquitin protease Ubp8 and Sgf11 constitute a discrete functional module within the *Saccharomyces cerevisiae* SAGA complex. Mol Cell Biol. Feb. 2005;25(3):1162-72.

Krogan et al., Global landscape of protein complexes in the yeast *Saccharomyces cerevisiae*. Nature. Mar. 30, 2006;440(7084):637-43. Epub Mar. 22, 2006.

Lee et al., The deubiquitylation activity of Ubp8 is dependent upon Sgf11 and its association with the SAGA complex. Mol Cell Biol. Feb. 2005;25(3):1173-82.

Luchansky et al., Substrate recognition and catalysis by UCH-L1. Biochemistry. Dec. 12, 2006;45(49):14717-25.

Nijman et al., The deubiquitinating enzyme USP1 regulates the Fanconi anemia pathway. Mol Cell. Feb. 4, 2005;17(3):331-9.

Qui et al., hRpn13/ADRM1/GP110 is a novel proteasome subunit that binds the deubiquitinating enzyme, UCH37. EMBO J. Dec. 13, 2006;25(24):5742-53. Epub Nov. 30, 2006.

Renatus et al., Structural basis of ubiquitin recognition by the deubiquitinating protease USP2. Structure. Aug. 2006;14(8):1293-302.

Rumpf et al., Functional division of substrate processing cofactors of the ubiquitin-selective Cdc48 chaperone. Mol Cell. Jan. 20, 2006;21(2):261-9.

UniProt database ID. No. UBP1_HUMAN reference; Huang et al., Regulation of monoubiquitinated PCNA by DUB autocleavage. Nat Cell Biol. Apr. 2006; 8(4):339-47. Epub Mar. 12, 2006.

Whisstock et al., Prediction of protein function from protein sequence and structure. Q Rev Biophys. Aug. 2003;36(3):307-40.

Yao et al., Proteasome recruitment and activation of the Uch37 deubiquitinating enzyme by Adrm1. Nat Cell Biol. Sep. 2006;8(9):994-1002. Epub Aug. 13, 2006.

* cited by examiner

|  | Km (µM) | kcat (s⁻¹) | kcat/Km (s⁻¹ x M) |
|---|---|---|---|
| USP1 | 1.4 (±0.3) | $1.4 \times 10^{-2}$ (±$0.2 \times 10^{-2}$) | $1.02 \times 10^4$ (±$0.09 \times 10^4$) |
| USP1/UAF1 | 0.7 (±0.1) | $26 \times 10^{-2}$ (±$1.4 \times 10^{-2}$) | $36 \times 10^4$ (±$0.4 \times 10^4$) |

FIG. 3F

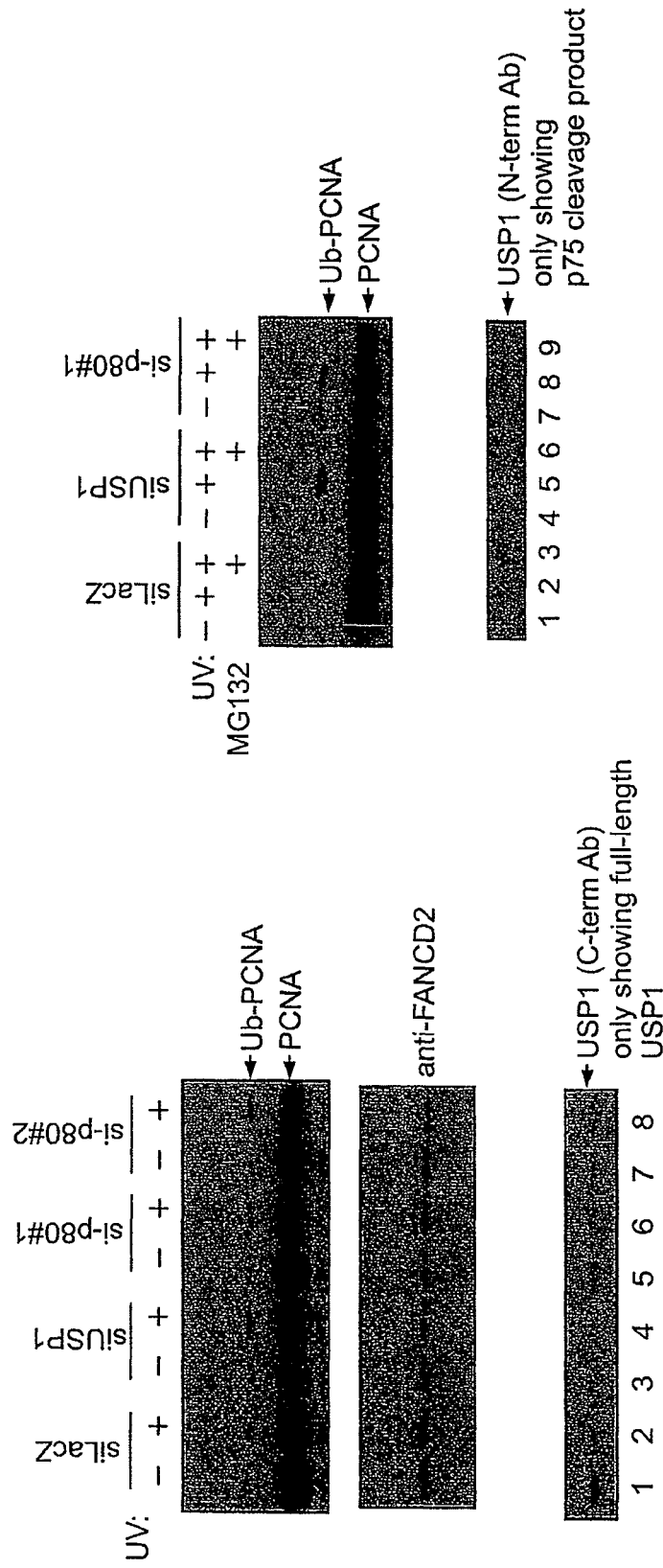

Reaction vol: 30ul

| UB-AMC Concentration | USP1/UAF1 concentration →   |||||||||||||||||||
|---|---|---|---|---|---|---|---|---|---|---|---|---|---|---|---|---|---|---|
| | 0.2nM ||| 0.4nM ||| 0.8nM ||| 1.6nM ||| 3.2nM |||
| 0.025μM | 1 | 2 | 3 | 1 | 2 | 3 | 1 | 2 | 3 | 1 | 2 | 3 | 1 | 2 | 3 |
| 0.05μM  | 1 | 2 | 3 | 1 | 2 | 3 | 1 | 2 | 3 | 1 | 2 | 3 | 1 | 2 | 3 |
| 0.1μM   | 1 | 2 | 3 | 1 | 2 | 3 | 1 | 2 | 3 | 1 | 2 | 3 | 1 | 2 | 3 |
| 0.2μM   | 1 | 2 | 3 | 1 | 2 | 3 | 1 | 2 | 3 | 1 | 2 | 3 | 1 | 2 | 3 |

FIG. 14A

SEQUENCE LISTING

<160> NUMBER OF SEQ ID NOS: 11

<210> SEQ ID NO 1
<211> LENGTH: 76
<212> TYPE: PRT
<213> ORGANISM: Homo sapiens

<400> SEQUENCE: 1

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
```

```
                50                  55                  60
Ser Thr Leu His Leu Val Leu Arg Leu Arg Gly Gly
 65                  70                  75
```

<210> SEQ ID NO 2
<211> LENGTH: 261
<212> TYPE: PRT
<213> ORGANISM: Homo sapiens

<400> SEQUENCE: 2

```
Met Phe Glu Ala Arg Leu Val Gln Gly Ser Ile Leu Lys Lys Val Leu
 1               5                  10                  15
Glu Ala Leu Lys Asp Leu Ile Asn Glu Ala Cys Trp Asp Ile Ser Ser
                20                  25                  30
Ser Gly Val Asn Leu Gln Ser Met Asp Ser Ser His Val Ser Leu Val
            35                  40                  45
Gln Leu Thr Leu Arg Ser Glu Gly Phe Asp Thr Tyr Arg Cys Asp Arg
         50                  55                  60
Asn Leu Ala Met Gly Val Asn Leu Thr Ser Met Ser Lys Ile Leu Lys
 65                  70                  75                  80
Cys Ala Gly Asn Glu Asp Ile Ile Thr Leu Arg Ala Glu Asp Asn Ala
                 85                  90                  95
Asp Thr Leu Ala Leu Val Phe Glu Ala Pro Asn Gln Glu Lys Val Ser
            100                 105                 110
Asp Tyr Glu Met Lys Leu Met Asp Leu Asp Val Glu Gln Leu Gly Ile
         115                 120                 125
Pro Glu Gln Glu Tyr Ser Cys Val Val Lys Met Pro Ser Gly Glu Phe
130                 135                 140
Ala Arg Ile Cys Arg Asp Leu Ser His Ile Gly Asp Ala Val Val Ile
145                 150                 155                 160
Ser Cys Ala Lys Asp Gly Val Lys Phe Ser Ala Ser Gly Glu Leu Gly
                165                 170                 175
Asn Gly Asn Ile Lys Leu Ser Gln Thr Ser Asn Val Asp Lys Glu Glu
            180                 185                 190
Glu Ala Val Thr Ile Glu Met Asn Glu Pro Val Gln Leu Thr Phe Ala
        195                 200                 205
Leu Arg Tyr Leu Asn Phe Phe Thr Lys Ala Thr Pro Leu Ser Ser Thr
    210                 215                 220
Val Thr Leu Ser Met Ser Ala Asp Val Pro Leu Val Val Glu Tyr Lys
225                 230                 235                 240
Ile Ala Asp Met Gly His Leu Lys Tyr Tyr Leu Ala Pro Lys Ile Glu
                245                 250                 255
Asp Glu Glu Gly Ser
            260
```

<210> SEQ ID NO 3
<211> LENGTH: 785
<212> TYPE: PRT
<213> ORGANISM: Homo sapiens

<400> SEQUENCE: 3

```
Met Pro Gly Val Ile Pro Ser Glu Ser Asn Gly Leu Ser Arg Gly Ser
 1               5                  10                  15
Pro Ser Lys Lys Asn Arg Leu Ser Leu Lys Phe Phe Gln Lys Lys Glu
                20                  25                  30
Thr Lys Arg Ala Leu Asp Phe Thr Asp Ser Gln Glu Asn Glu Glu Lys
            35                  40                  45
```

-continued

```
Ala Ser Glu Tyr Arg Ala Ser Glu Ile Asp Gln Val Val Pro Ala Ala
         50                  55                  60
Gln Ser Ser Pro Ile Asn Cys Glu Lys Arg Glu Asn Leu Leu Pro Phe
 65                  70                  75                  80
Val Gly Leu Asn Asn Leu Gly Asn Thr Cys Tyr Leu Asn Ser Ile Leu
                 85                  90                  95
Gln Val Leu Tyr Phe Cys Pro Gly Phe Lys Ser Gly Val Lys His Leu
            100                 105                 110
Phe Asn Ile Ile Ser Arg Lys Lys Glu Ala Leu Lys Asp Glu Ala Asn
            115                 120                 125
Gln Lys Asp Lys Gly Asn Cys Lys Glu Asp Ser Leu Ala Ser Tyr Glu
        130                 135                 140
Leu Ile Cys Ser Leu Gln Ser Leu Ile Ile Ser Val Glu Gln Leu Gln
145                 150                 155                 160
Ala Ser Phe Leu Leu Asn Pro Glu Lys Tyr Thr Asp Glu Leu Ala Thr
                165                 170                 175
Gln Pro Arg Arg Leu Leu Asn Thr Leu Arg Glu Leu Asn Pro Met Tyr
            180                 185                 190
Glu Gly Tyr Leu Gln His Asp Ala Gln Glu Val Leu Gln Cys Ile Leu
            195                 200                 205
Gly Asn Ile Gln Glu Thr Cys Gln Leu Leu Lys Lys Glu Glu Val Lys
        210                 215                 220
Asn Val Ala Glu Leu Pro Thr Lys Val Glu Glu Ile Pro His Pro Lys
225                 230                 235                 240
Glu Glu Met Asn Gly Ile Asn Ser Ile Glu Met Asp Ser Met Arg His
                245                 250                 255
Ser Glu Asp Phe Lys Glu Lys Leu Pro Lys Gly Asn Gly Lys Arg Lys
            260                 265                 270
Ser Asp Thr Glu Phe Gly Asn Met Lys Lys Val Lys Leu Ser Lys
            275                 280                 285
Glu His Gln Ser Leu Glu Glu Asn Gln Arg Gln Thr Arg Ser Lys Arg
        290                 295                 300
Lys Ala Thr Ser Asp Thr Leu Glu Ser Pro Pro Lys Ile Ile Pro Lys
305                 310                 315                 320
Tyr Ile Ser Glu Asn Glu Ser Pro Arg Pro Ser Gln Lys Lys Ser Arg
                325                 330                 335
Val Lys Ile Asn Trp Leu Lys Ser Ala Thr Lys Gln Pro Ser Ile Leu
            340                 345                 350
Ser Lys Phe Cys Ser Leu Gly Lys Ile Thr Thr Asn Gln Gly Val Lys
        355                 360                 365
Gly Gln Ser Lys Glu Asn Glu Cys Asp Pro Glu Asp Leu Gly Lys
    370                 375                 380
Cys Glu Ser Asp Asn Thr Thr Asn Gly Cys Gly Leu Glu Ser Pro Gly
385                 390                 395                 400
Asn Thr Val Thr Pro Val Asn Val Asn Glu Val Lys Pro Ile Asn Lys
                405                 410                 415
Gly Glu Glu Gln Ile Gly Phe Glu Leu Val Glu Lys Leu Phe Gln Gly
            420                 425                 430
Gln Leu Val Leu Arg Thr Arg Cys Leu Glu Cys Glu Ser Leu Thr Glu
        435                 440                 445
Arg Arg Glu Asp Phe Gln Asp Ile Ser Val Pro Val Gln Glu Asp Glu
450                 455                 460
Leu Ser Lys Val Glu Glu Ser Ser Glu Ile Ser Pro Glu Pro Lys Thr
```

```
            465                 470                 475                 480
        Glu Met Lys Thr Leu Arg Trp Ala Ile Ser Gln Phe Ala Ser Val Glu
                        485                 490                 495

Arg Ile Val Gly Glu Asp Lys Tyr Phe Cys Glu Asn Cys His His Tyr
                    500                 505                 510

Thr Glu Ala Glu Arg Ser Leu Leu Phe Asp Lys Met Pro Glu Val Ile
                    515                 520                 525

Thr Ile His Leu Lys Cys Phe Ala Ala Ser Gly Leu Glu Phe Asp Cys
                    530                 535                 540

Tyr Gly Gly Leu Ser Lys Ile Asn Thr Pro Leu Leu Thr Pro Leu
        545                 550                 555                 560

Lys Leu Ser Leu Glu Glu Trp Ser Thr Lys Pro Thr Asn Asp Ser Tyr
                        565                 570                 575

Gly Leu Phe Ala Val Val Met His Ser Gly Ile Thr Ile Ser Ser Gly
                    580                 585                 590

His Tyr Thr Ala Ser Val Lys Val Thr Asp Leu Asn Ser Leu Glu Leu
                    595                 600                 605

Asp Lys Gly Asn Phe Val Val Asp Gln Met Cys Glu Ile Gly Lys Pro
                610                 615                 620

Glu Pro Leu Asn Glu Glu Ala Arg Gly Val Val Glu Asn Tyr Asn
        625                 630                 635                 640

Asp Glu Glu Val Ser Ile Arg Val Gly Gly Asn Thr Gln Pro Ser Lys
                        645                 650                 655

Val Leu Asn Lys Lys Asn Val Glu Ala Ile Gly Leu Leu Gly Gly Gln
                    660                 665                 670

Lys Ser Lys Ala Asp Tyr Glu Leu Tyr Asn Lys Ala Ser Asn Pro Asp
                    675                 680                 685

Lys Val Ala Ser Thr Ala Phe Ala Glu Asn Arg Asn Ser Glu Thr Ser
                690                 695                 700

Asp Thr Thr Gly Thr His Glu Ser Asp Arg Asn Lys Glu Ser Ser Asp
        705                 710                 715                 720

Gln Thr Gly Ile Asn Ile Ser Gly Phe Glu Asn Lys Ile Ser Tyr Val
                        725                 730                 735

Val Gln Ser Leu Lys Glu Tyr Glu Gly Lys Trp Leu Leu Phe Asp Asp
                    740                 745                 750

Ser Glu Val Lys Val Thr Glu Lys Asp Phe Leu Asn Ser Leu Ser
                    755                 760                 765

Pro Ser Thr Ser Pro Thr Ser Thr Pro Tyr Leu Leu Phe Tyr Lys Lys
                770                 775                 780

Leu
        785

<210> SEQ ID NO 4
<211> LENGTH: 676
<212> TYPE: PRT
<213> ORGANISM: Homo sapiens

<400> SEQUENCE: 4

Met Ala Ala His His Arg Gln Asn Thr Ala Gly Arg Arg Lys Val Gln
1               5                   10                  15

Val Ser Tyr Val Ile Arg Asp Glu Val Glu Lys Tyr Asn Arg Asn Gly
                20                  25                  30

Val Asn Ala Leu Gln Leu Asp Pro Ala Leu Asn Arg Leu Phe Thr Ala
            35                  40                  45

Gly Arg Asp Ser Ile Ile Arg Ile Trp Ser Val Asn Gln His Lys Gln
```

-continued

```
                50                  55                  60
Asp Pro Tyr Ile Ala Ser Met Glu His His Thr Asp Trp Val Asn Asp
65                  70                  75                  80

Ile Val Leu Cys Cys Asn Gly Lys Thr Leu Ile Ser Ala Ser Ser Asp
                85                  90                  95

Thr Thr Val Lys Val Trp Asn Ala His Lys Gly Phe Cys Met Ser Thr
            100                 105                 110

Leu Arg Thr His Lys Asp Tyr Val Lys Ala Leu Ala Tyr Ala Lys Asp
            115                 120                 125

Lys Glu Leu Val Ala Ser Ala Gly Leu Asp Arg Gln Ile Phe Leu Trp
        130                 135                 140

Asp Val Asn Thr Leu Thr Ala Leu Thr Ala Ser Asn Asn Thr Val Thr
145                 150                 155                 160

Thr Ser Ser Leu Ser Gly Asn Lys Asp Ser Ile Tyr Ser Leu Ala Met
                165                 170                 175

Asn Gln Leu Gly Thr Ile Ile Val Ser Gly Ser Thr Glu Lys Val Leu
            180                 185                 190

Arg Val Trp Asp Pro Arg Thr Cys Ala Lys Leu Met Lys Leu Lys Gly
        195                 200                 205

His Thr Asp Asn Val Lys Ala Leu Leu Leu Asn Arg Asp Gly Thr Gln
    210                 215                 220

Cys Leu Ser Gly Ser Ser Asp Gly Thr Ile Arg Leu Trp Ser Leu Gly
225                 230                 235                 240

Gln Gln Arg Cys Ile Ala Thr Tyr Arg Val His Asp Glu Gly Val Trp
                245                 250                 255

Ala Leu Gln Val Asn Asp Ala Phe Thr His Val Tyr Ser Gly Gly Arg
            260                 265                 270

Asp Arg Lys Ile Tyr Cys Thr Asp Leu Arg Asn Pro Asp Ile Arg Val
        275                 280                 285

Leu Ile Cys Glu Glu Lys Ala Pro Val Leu Lys Met Glu Leu Asp Arg
    290                 295                 300

Ser Ala Asp Pro Pro Ala Ile Trp Val Ala Thr Thr Lys Ser Thr
305                 310                 315                 320

Val Asn Lys Trp Thr Leu Lys Gly Ile His Asn Phe Arg Ala Ser Gly
                325                 330                 335

Asp Tyr Asp Asn Asp Cys Thr Asn Pro Ile Thr Pro Leu Cys Thr Gln
            340                 345                 350

Pro Asp Gln Val Ile Lys Gly Gly Ala Ser Ile Ile Gln Cys His Ile
        355                 360                 365

Leu Asn Asp Lys Arg His Ile Leu Thr Lys Asp Thr Asn Asn Val
370                 375                 380

Ala Tyr Trp Asp Val Leu Lys Ala Cys Lys Val Glu Asp Leu Gly Lys
385                 390                 395                 400

Val Asp Phe Glu Asp Glu Ile Lys Lys Arg Phe Lys Met Val Tyr Val
            405                 410                 415

Pro Asn Trp Phe Ser Val Asp Leu Lys Thr Gly Met Leu Thr Ile Thr
        420                 425                 430

Leu Asp Glu Ser Asp Cys Phe Ala Ala Trp Val Ser Ala Lys Asp Ala
    435                 440                 445

Gly Phe Ser Ser Pro Asp Gly Ser Asp Pro Lys Leu Asn Leu Gly Gly
    450                 455                 460

Leu Leu Leu Gln Ala Leu Leu Glu Tyr Trp Pro Arg Thr His Val Asn
465                 470                 475                 480
```

```
Pro Met Asp Glu Glu Glu Asn Glu Val Asn His Val Asn Gly Glu Gln
            485                 490                 495

Glu Asn Arg Val Gln Lys Gly Asn Gly Tyr Phe Gln Val Pro Pro His
            500                 505                 510

Thr Pro Val Ile Phe Gly Glu Ala Gly Gly Arg Thr Leu Phe Arg Leu
            515                 520                 525

Leu Cys Arg Asp Ser Gly Gly Glu Thr Glu Ser Met Leu Leu Asn Glu
            530                 535                 540

Thr Val Pro Gln Trp Val Ile Asp Ile Thr Val Asp Lys Asn Met Pro
545                 550                 555                 560

Lys Phe Asn Lys Ile Pro Phe Tyr Leu Gln Pro His Ala Ser Ser Gly
            565                 570                 575

Ala Lys Thr Leu Lys Lys Asp Arg Leu Ser Ala Ser Asp Met Leu Gln
            580                 585                 590

Val Arg Lys Val Met Glu His Val Tyr Glu Lys Ile Ile Asn Leu Asp
            595                 600                 605

Asn Glu Ser Gln Thr Thr Ser Ser Asn Asn Gly Lys Pro Gly Glu
            610                 615                 620

Gln Glu Lys Glu Glu Asp Ile Ala Val Leu Ala Glu Glu Lys Ile Glu
625                 630                 635                 640

Leu Leu Cys Gln Asp Gln Val Leu Asp Pro Asn Met Asp Leu Arg Thr
            645                 650                 655

Val Lys His Phe Ile Trp Lys Ser Gly Gly Asp Leu Thr Leu His Tyr
            660                 665                 670

Arg Gln Lys Ser
            675

<210> SEQ ID NO 5
<211> LENGTH: 21
<212> TYPE: DNA
<213> ORGANISM: Homo sapiens

<400> SEQUENCE: 5
tcggcaatac ttgctatctt a                                      21

<210> SEQ ID NO 6
<211> LENGTH: 21
<212> TYPE: DNA
<213> ORGANISM: Homo sapiens

<400> SEQUENCE: 6
ttggcaagtt atgaattgat a                                      21

<210> SEQ ID NO 7
<211> LENGTH: 19
<212> TYPE: DNA
<213> ORGANISM: Homo sapiens

<400> SEQUENCE: 7
acagttcgct tctacacaa                                         19

<210> SEQ ID NO 8
<211> LENGTH: 21
<212> TYPE: DNA
<213> ORGANISM: Homo sapiens

<400> SEQUENCE: 8
ccggtcgaga ctctatcata a                                      21
```

-continued

```
<210> SEQ ID NO 9
<211> LENGTH: 21
<212> TYPE: DNA
<213> ORGANISM: Homo sapiens

<400> SEQUENCE: 9
cacaagcaag atccatatat a                                              21

<210> SEQ ID NO 10
<211> LENGTH: 19
<212> TYPE: DNA
<213> ORGANISM: Homo sapiens

<400> SEQUENCE: 10
caagcaagat ccatatata                                                 19

<210> SEQ ID NO 11
<211> LENGTH: 18
<212> TYPE: DNA
<213> ORGANISM: Homo sapiens

<400> SEQUENCE: 11
ggaccgagat tatctttc                                                  18
```

METHODS TO IDENTIFY USP1 DEUBIQUITINATING ENZYME COMPLEX INHIBITORS

RELATED APPLICATIONS

This application is a continuation of U.S. Ser. No. 11/820,674, filed Jun. 20, 2007, which claims the benefit of U.S. provisional application Ser. No. 60/815,483, filed Jun. 20, 2006, the entire disclosures of both of which are incorporated herein by reference.

GOVERNMENT SUPPORT

This invention was made with government support under grants DK43889 and HL52725 from the National Institutes of Health. The U.S. Government has certain rights in the invention.

TECHNICAL FIELD

The invention generally relates to deubiquitinating enzymes. More particularly the invention relates to compositions and methods for inhibition of USP1, a deubiquitinase whose inhibition increases the resistance of eukaryotic cells to the damaging effects of ionizing radiation and DNA-damaging chemicals.

BACKGROUND

The need for radioprotective agents in protecting against the harmful effects of exposure to environmental radiation and cancer radiation therapy is well recognized. At present there are few agents available for protection of human tissues from the damaging effects of ionizing radiation, occurring either as a side effect of the treatment of various cancers, or through intentional or accidental exposure from other sources. Amifostine is the only drug currently approved by the federal Food and Drug Administration for the protection of normal tissue from the disruptive effects of cancer chemotherapy and radiation. An active metabolite of the drug is taken up by cells, where it scavenges the damaging free oxygen radicals caused by exposure to IR, UV or cancer chemotherapy. Other antioxidants have been used, but they all have very limited effectiveness. Polyamino acid compounds in various fauns have been claimed as radioprotective agents in several patents, including U.S. Pat. Nos. 7,041,994, 6,114,394, 5,434,145, 5,354,782, and 5,217,964. Antiinflammatory drugs have also been used, but their effect is limited primarily to blocking the cascade of chemical reactions induced by cellular damage, rather than preventing or correcting the cellular damage that triggers the process.

Exposure to radiation increases the rate of damage to DNA in the cell nucleus. Sufficient DNA damage results in excessively prolonged, defective or arrested DNA transcription, leading to cell death. One approach to this problem therefore involves compositions and methods to preserve DNA transcription activity in the cell. Moreover, an agent with this property could also be used in cancer treatment to selectively protect normal cells from the damaging effects that radiation and antineoplastic agents have on all cells.

Ubiquitin is a small protein consisting of 76 amino acids that is important in the regulation of protein function in the cell. Ubiquitination and deubiquitination are enzymatically mediated processes by which ubiquitin is covalently bound to or unbound from a target protein. These processes have been implicated in the regulation of the cell cycle, apoptosis, the marking of transmembrane proteins such as receptors for removal, regulation of DNA transcription and repair, and other important functions. Proteins are targeted for degradation by the proteasome in the cell by being "tagged" with three or more ubiquitin molecules (polyubiquitination). Ubiquitin molecules are cleaved from a protein by deubiquitinating enzymes, which are cysteine proteases that operate through an active site thiol. The binding of a single ubiquitin molecule (monoubiquitination) does not generally target the monoubiquitinated protein for degradation. Rather, it may trigger activities such as DNA repair and gene silencing, among other functions. (Huang and D'Andrea, Mol. Cell Biol. 7:323-34 (2006)). Deubiquitination allows the ubiquitin to be recycled and restores the function of the deubiquitinated protein. There are approximately 95 different deubiquitinating enzymes in human cells (Huang et al., Nature Cell Biol. 8(4):339-47 (2006)). Among them, Ubiquitin Specific Protease 1 (USP1) has been found to regulate the repair of DNA damage induced by DNA crosslinking agents, which include agents such as mitomycin C (MMC), cisplatin, dipoxybutane (DEB), ionizing radiation (IR) and ultraviolet radiation (UV). USP1 has been shown to deubiquitinate monoubiquitinated FANCD2 (FANCD2-Ub), a protein that in monoubiquitinated form mediates DNA repair from the damage induced by the aforementioned agents. (Nijman et al., Molecular Cell 17:331-39 (2005)). USP1 also has been shown to deubiquitinate monoubiquitinated PCNA (PCNA-Ub), a protein that in monoubiquitinated form activates DNA translesion synthesis (TLS), a polymerase-mediated bypass of DNA lesions. (Huang, et al., Nature Cell Biol. 8(4):339-47 ((2006)).

SUMMARY OF THE INVENTION

The invention provides compositions and methods for inhibiting the activity of USP1, causing an increase in the level of PCNA-Ub or FANCD2-Ub in the cell. With increased level of PCNA-Ub, FANCD2-Ub, or both, DNA repair activity in the cell nucleus is increased, which increases the viability of a cell exposed to genotoxic agents such as ionizing radiation, ultraviolet light, and antineoplastic agents.

It is an object of the invention to provide inhibitors of USP1 deubiquitinase activity. In one embodiment, the inhibitor is an siRNA which is sufficiently complementary to a USP1 gene sequence to direct RNA interference against the expression of a USP1 gene when administered to a cell. In another embodiment the inhibitor is an siRNA which is sufficiently complementary to a UAF1 gene sequence to direct RNA interference against the expression of the UAF1 gene when administered to a cell. In another embodiment, the inhibitor is a combination of a USP1 siRNA and a UAF1 siRNA. In yet another embodiment, the inhibitor is a combination of a USP1 siRNA or a UAF1 siRNA and amifostine, ubiquitin aldehyde, β-Lapachone, Biomol AP401, and RK-682.

It is also an object of the invention to provide a method for protecting a subject from radiation damage. In one embodiment, the method comprises administering an effective amount of an inhibitor of USP1 deubiquitinase activity to the subject.

Another object of the invention to provide a method for increasing the level of DNA repair activity in a cell. In one embodiment, the method comprises contacting the cell with an effective amount of an inhibitor of USP1 deubiquitinase activity.

Yet another object of the invention to provide a method for determining the level of DNA repair activity in a cell. In one embodiment, the method comprises measuring the level of USP1 deubiquitinase activity in the cell and comparing it to the level of USP1 deubiquitinase activity in a panel of biomarkers. The biomarkers can be a series of populations of recombinant cells, with each population having a different average level of USP1 deubiquitinase activity.

Still another object of the invention is to provide a method of treating cancer in a subject. The method comprises administering to the subject an inhibitor of USP1 deubiquitinase activity. In certain embodiments, both an inhibitor of USP1 and either an antineoplastic agent or radiotherapy are also administered to the subject.

Still another object of the invention is to provide a method of treating a disease resulting from bone marrow failure, which in turn results from DNA damage. In one embodiment, the method comprises administering to a subject having or suspected of having the disease an effective amount of an inhibitor of USP1 deubiquitinase activity. In one embodiment, the disease is aplastic anemia caused by chemotherapy-induced bone marrow failure, radiation-induced bone marrow failure, or a congenital disease.

A further object of the invention is to provide a method of enhancing cancer therapy in a subject who is receiving an antineoplasitic agent. In one embodiment, the method comprises administering a cytoprotective amount of an inhibitor of USP1 deubiquitinase activity and increasing the dose of antineoplastic agent administered to the patient. In various embodiments, the antineoplastic agent is either a small molecule chemotherapy drug, an antibody of antibody fragment, or radiotherapy.

Yet another object of the invention is to provide a method of enhancing cancer therapy in a subject who is receiving an antineoplasitic agent. In one embodiment, the method comprises administering a cytoprotective amount of an inhibitor of USP1 deubiquitinase activity and administering an additional antineoplastic agent to the patient. In various embodiments, the additional antineoplastic agent is either a small molecule chemotherapy drug, an antibody or antibody fragment, or radiotherapy.

Another object of the invention is to provide a method for protecting a subject from radiation damage. In one embodiment, an effective amount of an inhibitor of USP1 deubiquitinase activity is administered to the subject prior to radiation exposure. In another embodiment an effective amount of an inhibitor of USP1 deubiquitinase activity is administered to the subject after radiation exposure. In various embodiments, the source of radiation exposure UV light, X-rays, gamma rays, a particle beam, cosmic rays, radiation from a nuclear reactor, radiation from an explosive device, radioactive fallout from a nuclear accident or explosion, or radiation exposure from space travel Still another object of the invention is to provide a method for treating a subject who has been exposed to radiation. In one embodiment, the method comprises administering an effective amount of an inhibitor of USP1 deubiquitinase activity to the subject. In different embodiments the source of the radiation can be UV light, X-rays, gamma rays, a particle beam, cosmic rays, radiation from a nuclear reactor, radiation from an explosive device, radioactive fallout from a nuclear accident or explosion, or radiation exposure from space travel. In certain embodiments, another agent, such as another radioprotective agent, an antioxidant, an immune regulator, or an antiinflammatory agent, is administered to the subject.

A further object of the invention is to provide a method for identifying inhibitors of USP1 deubiquitinase activity. In one embodiment, a cell is exposed to a test compound, and the amount of deubiquitination of monoubiquitinated PCNA is measured. A test compound which increases the amount of monoubiquitinated PCNA in the cell is identified as an inhibitor of USP1 deubiquitinase activity. In one embodiment, the cell is a cancer cell. In another embodiment, the cell expresses USP1 from an exogenous construct. In yet another embodiment, the cell expresses UAF1 from an exogenous construct. In a further embodiment, the cell expresses PCNA from an expression construct. In some embodiments the test compound is an siRNA.

Another object of the invention to provide a method for identifying inhibitors of USP1 deubiquitinase activity. In one embodiment, an isolated USP1 polypeptide is exposed to a test compound, and the amount of deubiquitination of an isolated monoubiquitinated PCNA polypeptide is measured. A test compound which increases the amount of monoubiquitinated PCNA in the cell is identified as an inhibitor of USP1 deubiquitinase activity. In another embodiment, an isolated heterodimeric molecular complex comprising USP1 and UAF1 is exposed to a test compound, and the amount of deubiquitination of an isolated monoubiquitinated PCNA polypeptide is measured. A test compound which increases the amount of monoubiquitinated PCNA in the cell is identified as an inhibitor of USP1 deubiquitinase activity.

A further object of the invention to provide a method for identifying inhibitors of USP1 deubiquitinase activity. In one embodiment, a cell is exposed to a test compound, and the amount of deubiquitination of monoubiquitinated FANCD2 is measured. A test compound which increases the amount of monoubiquitinated FANCD2 in the cell is identified as an inhibitor of USP1 deubiquitinase activity. In one embodiment, the cell is a cancer cell. In another embodiment, the cell expresses USP1 from an exogenous construct. In yet another embodiment, the cell expresses UAF1 from an expression construct. In a further embodiment, the cell expresses FANCD2 from an exogenous construct. In some embodiments the test compound is an siRNA.

Another object of the invention to provide a method for identifying inhibitors of USP1 deubiquitinase activity. In one embodiment, an isolated USP1 polypeptide is exposed to a test compound, and the amount of deubiquitination of an isolated monoubiquitinated FANCD2 polypeptide is measured. A test compound which increases the amount of monoubiquitinated FANCD2 in the cell is identified as an inhibitor of USP1 deubiquitinase activity. In another embodiment, an isolated heterodimeric molecular complex comprising USP1 and UAF1 is exposed to a test compound, and the amount of deubiquitination of an isolated monoubiquitinated FANCD2 polypeptide is measured. A test compound which increases the amount of monoubiquitinated FANCD2 in the cell is identified as an inhibitor of USP1 deubiquitinase activity.

Another object of the invention is to provide a method for identifying a cytoprotective agent. In one embodiment, a cell is contacted with an inhibitor of USP1 deubiquitinase activity and exposed to a genotoxic agent. Cell survival is then determined, and if cell survival is increased in the presence of the inhibitor of USP1 deubiquitinase activity, then the inhibitor is identified as a cytoprotective agent. In different embodiments, the inhibitor can be UV light, ionizing radiation, or an antineoplastic agent.

A further object of the invention to provide a method for identifying inhibitors of USP1 deubiquitinase activity. In one embodiment, an isolated USP1 polypeptide is exposed to a test compound, and the amount of deubiquitination of an isolated monoubiquitinated PCNA polypeptide is measured. A test compound which increases the amount of monoubiquitinated PCNA in the cell is identified as an inhibitor of USP1 deubiquitinase activity. In another embodiment, an isolated heterodimeric molecular complex comprising USP1 and UAF1 is exposed to a test compound, and the amount of deubiquitination of an isolated monoubiquitinated PCNA polypeptide is measured. A test compound which increases the amount of monoubiquitinated PCNA in the cell is identified as an inhibitor of USP1 deubiquitinase activity.

Another object of the invention is to provide a method for identifying a cytoprotective agent. In one embodiment, a cell is contacted with an inhibitor of USP1 deubiquitinase activity and exposed to a genotoxic agent. Cell survival is then determined, and if cell survival is increased in the presence of the inhibitor of USP1 deubiquitinase activity, then the inhibitor is identified as a cytoprotective agent. In different embodiments, the inhibitor can be UV light, ionizing radiation, or an antineoplastic agent.

Yet another object of the invention is to provide compositions that can be used to identify inhibitors of USP1 deubiquitinase activity. One embodiment is a composition comprising an isolated USP1 polypeptide, or a fragment thereof (e.g., a USP1 polypeptide at least 80% identical to the sequence of SEQ ID NO: 3, preferably at least 90% identical, and more preferably at least 95% identical to the sequence of SEQ ID NO: 3) possessing deubiquitinase activity, and an isolated PCNA polypeptide. Another embodiment is a composition comprising an isolated USP1 polypeptide, or a fragment thereof possessing deubiquitinase activity, and an isolated UAF1 polypeptide comprising the sequence of SEQ ID NO: 4 or a sequence at least 80%, 90%, or at least 95% identical thereto. In some embodiments, the fragment of USP1 with deubiquitinase activity is represented by amino acids 17-785 of SEQ ID NO:3.

A still further object of the invention is to provide cells and organisms with disrupted expression of USP1. One embodiment is a transgenic knockout mouse whose expression of USP1 has been disabled. In certain embodiments, the cells of the knockout mouse have increased levels of monoubiquitinated PCNA, or increased levels of monoubiquitinated FANCD2. In some embodiments, the knockout mouse has increased resistance to the damaging effects of antineoplastic agents, including small molecule chemotherapy drugs or radiation therapy. One embodiment is a cell comprising an siRNA which reduces the expression of USP1 in the cell. In certain embodiments, the siRNA increases DNA repair in the cell, which can be, for example, translesion DNA synthesis. In some embodiments siRNA increases the mutation frequency in the cell. In some embodiments, the comprises siRNA which reduces the expression of USP1, and the resistance of the cell to an effect of a genotoxic agent such as UV light, ionizing radiation, or an antineoplastic agent is increased.

Another object of the invention is to provide a method of making a transgenic mouse in which USP1 deubiquitinase activity has been inhibited. In one embodiment, the mouse is made by introducing a USP1 targeting vector into a mouse embryonic stem cell; introducing the mouse embryonic stem cell into a mouse blastocyst; transplanting the mouse blastocyst into a pseudopregnant mouse; allowing the transplanted mouse blastocyst to develop to term; identifying a transgenic mouse whose genome comprises a disruption of the endogenous USP1 gene in at least one allele; and breeding the transgenic mouse so identified to obtain a transgenic mouse whose genome comprises a homozygous disruption of the endogenous USP1 gene. In some embodiments, the disruption of the endogenous USP1 gene results in the transgenic mouse exhibiting an altered phenotype. In various embodiments, the mouse exhibits an altered phenotype such as increased cellular level of monoubiquitinated PCNA, increased cellular level of monoubiquitinated FANCD2, increased cell survival in the presence of Mitomycin C, reduced chromosomal breakage in the presence of Mitomycin C, increased mutation frequency after exposure to UV light, increased DNA replication after exposure to UV light, increased rate of translesion synthesis DNA repair, or increased skin tumorigenicity after exposure to UV light.

Still another object of the invention is to provide compositions for determining the level of DNA repair activity in a cell. In one embodiment, the composition comprises a recombinant cell that stably expresses an siRNA directed against USP1. In another embodiment, the composition comprises a recombinant cell that stably expresses an siRNA against UAF1. Yet another embodiment is a plurality of populations of recombinant cells, each population having a different average level of USP1 deubiquitinase activity.

Another object of the invention is to provide antibodies to a UAF1 polypeptide. One embodiment is a polyclonal antibody prepared against a fragment of human UAF1 consisting of amino acids 400-677 of SEQ ID NO:4.

The invention also provides a method for identifying an inhibitor of USP1 deubiquitinase by contacting USP1 with a test compound in the presence of moniubiquitinated PCNA, monoubiquitinated FANCD2, or ubiquitin-7-amido-4-methylcoumarin (Ub-AMC), and measuring the deubiquitination of PCNA, FANCD2, or Ub-AMC, wherein a decrease in the deubiquitination of PCNA, FANCD2, or Ub-AMC in the presence of the test compound relative to the absence of the test compound identifies the test compound as an inhibitor of USP1 deubiquitinase. This method can include the step of measuring the deubiquitination of PCNA, FANCD2 or Ub-AMC in the absence of the test compound.

USP1 used in the foregoing method can be in the form of a heterodimeric complex with UAF1. Either or both of USP1 and UAF1 can be expressed in a cell, preferably a recombinant cell, but the cell can also be a cancer cell. Similarly, PCNA, FANCD2, and/or Ub-AMC can be expressed in a recombinant cell alone, or in combination with USP1 and UAF1.

The invention also provides a method for identifying an inhibitor of USP1 deubiquitinase by measuring the deubiquitinase activity of USP1 in the presence and absence of a test compound, wherein a decrease in deubiquitinase activity in the presence of the test compound relative to the absence of the test compound identifies the compound as an inhibitor of USP1 deubiquitinase. The step of measuring deubiquitinase activity of USP1 can include measuring the deubiquitination of a substrate such as Ub-AMC, or monoubiquitinated PCNA or FANCD2.

USP1 used in the foregoing method can be expressed in a cell, such as a cancer cell or a recombinant cell, and is preferably present as a heterdimeric complex with UAF1.

The invention also provides a method for identifying an inhibitor of USP1 deubiquitinase, comprising contacting a composition comprising USP1 and UAF1 with a test compound in the presence of Ub-AMC; and measuring the deubiquitination of uUb-AMC, wherein a decrease in the deubiquitination of Ub-AMC in the presence of the test compound relative to the absence of the test compound identifies the test compound as an inhibitor of USP1 ubiquitinase. Either or both of USP1 and UAF1 can be expressed in a cell such as a cancer cell or recombinant cell.

The foregoing method can be adapted for use as a high throughput screening method. In particular, it is preferred that glycine residues at amino acid positions 670 and 671 of USP1 having the amino acid sequence of SEQ ID NO: 3 are substituted with alanine residues.

The invention also provides a method of identifying a compound as a compound useful for the treatment of genotoxin exposure, comprising measuring USP1 deubiquitinase activity in the presence and absence of a test agent; and determining whether USP1 deubiquitinase activity is decreased in the presence of the test agent, wherein if said activity is decreased in the presence of the test agent, the test agent is scored as a compound useful for the treatment of genotoxin exposure.

The invention also provides a method of identifying a compound as a compound useful for the treatment of cancer, comprising measuring USP1 deubiquitinase activity in the presence and absence of a test agent; and determining whether USP1 deubiquitinase activity is decreased in the presence of the test agent, wherein if said activity is decreased in the presence of the test agent, the test agent is scored as a compound useful for the treatment of cancer.

The invention still further provides a method of identifying a cytoprotective agent, comprising: contacting a cell with a candidate inhibitor of USP1 deubiquitinase; and exposing the cell to a genotoxic agent, and measuring cell survival, wherein if cell survival is increased, the candidate inhibitor is identified as a cytoprotective agent. The genotoxic agent in the foregoing method can be selected from the group consisting of UV light, ionizing radiation, and an antineoplastic agent.

The invention also provides a method of diagnosing cancer or an increased susceptibility to cancer in an individual comprising: measuring the level of USP1 and UAF1 in a cell from the individual, wherein an increase in the level of USP1 and UAF1 in the cell relative to a control is indicative of said individual having cancer or an increased susceptibility to cancer. The control used in the foregoing method can be a cell from an individual known to not have cancer or an increased susceptibility to cancer, or can be a cell from the test individual from tissue that is known to be normal, or not susceptible to cancer.

The foregoing method can also include the step of measuring the level of FANCD2 in said cell, wherein a decrease in the level of FANCD2 in said cell is indicative of the individual having cancer or an increased susceptibility to cancer.

The invention also provides a method of diagnosing cancer or an increased susceptibility to cancer in an individual comprising: measuring the binding of UAF1 to USP1 in a sample from said individual, wherein an increase in the binding of UAF1 to USP1 in said cell relative to a control is indicative of said individual having cancer or an increased susceptibility to cancer.

BRIEF DESCRIPTION OF THE DRAWINGS

FIG. 7A demonstrates the effect of USP1 and UAF1 knockdown using siRNA and its effect on the ubiquitination state of PCNA and FANCD2. Both USP1 and UAF1 knockdown increase the level of both monoubiquitinated PCNA and monoubiquitinated FANCD2. A Western blot is presented using an anti-PCNA antibody (top panel), an anti-FANCD2 antibody (middle panel) and a C-terminal specific anti-USP1 antibody (bottom panel). The effect of UV irradiation is indicated. In FIG. 7B, a Western blot shows the effects of UV irradiation and the proteasome inhibitor MG132 on the ubiquitination state of PCNA (upper panel, anti-PCNA antibody), and on the autocatalysis of USP1 (lower panel, N-terminal specific USP1 antibody).

FIG. 14A is a schematic representation of the experimental design to optimize concentrations of assay components.

DETAILED DESCRIPTION

Definitions

Figure 1A:
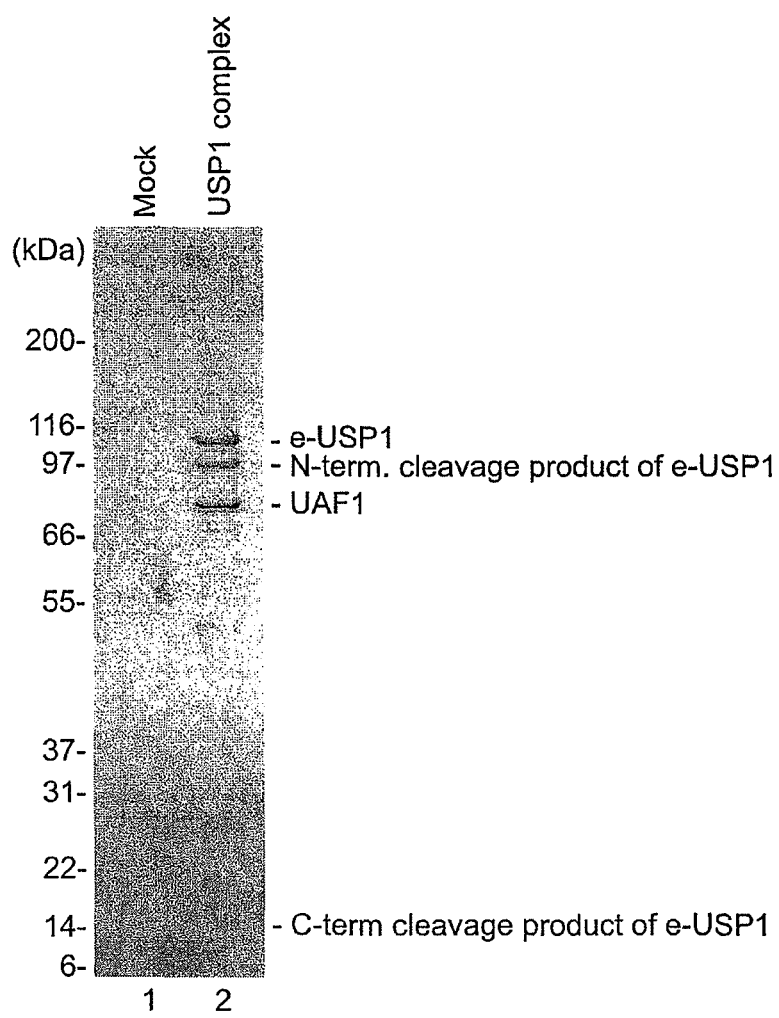
FIG. 1 shows purification of a native USP1 complex containing UAF1. A) The USP1 complex was purified from HeLa nuclear extract and stained by Coomassie blue stain. The polypeptides identified by mass spectrometry are indicated. B) Western blot analysis of the USP1 complex using anti-USP1 (top) or anti-UAF1 (bottom) antibodies. C) Endogenous USP1 interacts with UAF1. Flag-HA-tagged UAF1 was expressed in HeLa cells and immunoprecipitated by anti-Flag antibodies. The immunoprecipitate was analyzed by immunoblotting using anti-USP1 antibodies (top) and anti-UAF1 antibodies (bottom). D) The majority of cellular USP1 is in complex with UAF1. Flag-HA-tagged UAF1 was expressed in HeLa cells and immunoprecipitated by anti-Flag antibodies. The immunoprecipitates were analyzed by immunoblotting using the indicated antibodies. FT, flow through from the immunoprecipitation. IP, immunoprecipitate.

Ubiquitin is a 76 amino acid protein that binds covalently to other proteins, targeting them for degradation or regulating their function. The amino acid sequence of the human form of ubiquitin is given by: mqifvktltg ktitleveps dtienvkaki qdkegippdq qrlifagkql edgrtlsdyn iqkestlhlv lrlrgg (SEQ ID NO:1). Ubiquitin is a protein substrate which can be covalently attached to other proteins by a ubiquitin transferase enzyme, and likewise is a product released from a ubiquitinated protein by a deubiquitinating enzyme (DUB).

Proliferating cell nuclear antigen (PCNA) is a DNA replication sliding clamp protein that can form part of a DNA polymerase complex. Upon monoubiquitination, PCNA can interact with any of several different DNA polymerases to form a complex which carries out either DNA replication or DNA repair, particularly translesion DNA synthesis. (Huang & D'Andrea, Nature Reviews/Mol. Cell Biol. 7:323-34 (2006)). The amino acid sequence of the human form of PCNA is given by:

```
                                                                    (SEQ ID NO: 2)
  1 mfearlvqgs ilkkvlealk dlineacwdi sssgvnlqsm dsshvslvql tlrsegfdty 61 rcdrnlamgv nltsmskilk cagnediitl raednadtla lvfeapnqek vsdyemklmd 121 ldveqlgipe qeyscvvkmp sgefaricrd lshigdavvi scakdgvkfs asgelgngni 181 klsqtsnvdk eeeavtiemn epvqltfalr ylnfftkatp lsstvtlsms advplvveyk 241 iadmghlkyy lapkiedeeg s
```

Ubiquitin-specific protease 1 (USP1) is a cysteine protease with deubiquitinase activity. USP1 cleaves ubiquitin from monoubiquitinated and polyubiquitinated protein substrates, including PCNA and FANCD2. (Huang et al., Nature Cell Biol. 8(4):339-47 (2006), hereby incorporated by reference in its entirety). The amino acid sequence for the human form of USP1 is given by:

```
                                                                    (SEQ ID NO: 3)
  1 mpgvipsesn glsrgspskk nrlslkffqk ketkraldft dsqeneekas eyraseidqv 61 vpaaqsspin cekrenllpf vglnnlgntc ylnsilqvly fcpgfksgvk hlfniisrkk
```

```
-continued
121 ealkdeanqk dkgnckedsl asyelicslq sliisveqlq asfllnpeky tdelatqprr 181 llntlrelnp myegylqhda qevlqcilgn iqetcqllkk eevknvaelp tkveeiphpk 241 eemnginsie mdsmrhsedf keklpkgngk rksdtefgnm kkkvklskeh qsleenqrqt 301 rskrkatsdt lesppkiipk yisenesprp sqkksrvkin wlksatkqps ilskfcslgk 361 ittnqgvkgq skenecdpee dlgkcesdnt tngcglespg ntvtpvnvne vkpinkgeeq 421 igfelveklf qgqlvlrtrc leceslterr edfqdisvpv qedelskvee sseispepkt 481 emktlrwais qfasverivg edkyfcench hyteaersll fdkmpeviti hlkcfaasgl 541 efdcygggls kintplltpl klsleewstk ptndsyglfa vvmhsgitis sghytasvkv 601 tdlnsleldk gnfvvdqmce igkpeplnee eargvvenyn deevsirvgg ntqpskvlnk 661 knveaigllg gqkskadyel ynkasnpdkv astafaenrn setsdttgth esdrnkessd 721 qtginisgfe nkisyvvqsl keyegkwllf ddsevkvtee kdflnslsps tsptstpyll 781 fykkl
```

UAF1 is a WD repeat endosomal protein that is shown herein to form a heterodimeric complex with USP1, and thereby enhances the deubiquitinase activity of USP1. This protein has been previously shown to play a role in the downregulation of the T lymphocyte receptor. (Park et al., Immunity 17:221-33 (2002)). The amino acid sequence for human UAF1 is given by:

(SEQ ID NO: 4)
```
  1 maahhrqnta grrkvqvsyv irdevekynr ngvnalqldp alnrlftagr dsiiriwsvn 61 qhkqdpyias mehhtdwvnd ivlccngktl isassdttvk vwnahkgfcm stlrthkdyv 121 kalayakdke lvasagldrq iflwdvntlt altasnntvt tsslsgnkds iyslamnqlg 181 tiivsgstek vlrvwdprtc aklmklkght dnvkalllnr dgtqclsgss dgtirlwslg 241 qqrciatyrv hdegvwalqv ndafthvysg grdrkiyctd lrnpdirvli ceekapvlkm 301 eldrsadppp aiwvattkst vnkwtlkgih nfrasgdydn dctnpitplc tqpdqvikgg 361 asiiqchiln dkrhiltkdt nnnvaywdvl kackvedlgk vdfedeikkr fkmvyvpnwf 421 svdlktgmlt itldesdcfa awvsakdagf sspdgsdpkl nlgglllqal leywprthvn 481 pmdeeenevn hvngeqenrv qkgngyfqvp phtpvifgea ggrtlfrllc rdsggetesm 541 llnetvpqwv iditvdknmp kfnkipfylq phassgaktl kkdrlsasdm lqvrkvmehv 601 yekiinldne sqttsssnne kpgeqekeed iavlaeekie llcqdqvldp nmdlrtvkhf 661 iwksggdltl hyrqkst
```

As used herein a "conservative amino acid substitution" is one in which an amino acid residue is replaced with an amino acid residue having a side chain with similar biochemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Each protein described herein can be used in its native form, i.e., having the natural amino acid sequence as described herein or as published elsewhere, or it may be altered by using one or more conservative amino acid substitutions.

Short interfering RNA (siRNA) is a double-stranded RNA molecule that is generally 17 to 25 base pairs in length, one of whose strands contains a sequence (antisense sequence) that is complementary to a segment of a target messenger RNA. siRNA associates with an RNA-induced silencing complex in the cell, which then binds to a complementary region of a target messenger RNA and inactivates it.

Short interfering hairpin RNA ("shRNA") is a ribonucleic acid containing sense and antisense sequences from a target gene connected by a loop; it can be expressed in mammalian cells from a vector. Transcribed shRNA is transported from the nucleus into the cytoplasm, where it is processed, where it can decrease the expression of a gene with complementary sequences by RNA interference (RNAi).

As used herein, RNA interference ("RNAi") refers to a selective intracellular degradation of RNA by means of an RNA-induced silencing complex (RISC). RNAi occurs in cells naturally to remove foreign RNAs (e.g., viral RNAs). RNAi proceeds via fragments cleaved from free double-stranded RNA molecules (such as viral RNA) which direct the degradative mechanism to other similar RNA sequences. Introduction of the double-stranded RNA into a cell triggers the degradation of the double-stranded RNA into shorter siRNA strands. These siRNAs then associate with RNA-induced silencing complexes, leading to the unwinding of the siRNAs into single strands, which then associate with complementary regions of messenger RNA and prevent the expression of the corresponding proteins. The use of synthetic siRNA to "direct RNA interference (RNAi) against expression" of a target gene such as a USP1 gene or a UAF1 gene refers to the reduction of the expression of the target gene by entry of the synthetic siRNA into the natural RNAi mechanism at the same point as natural siRNA created from double-stranded RNA, e.g., viral RNA, would enter that mechanism. That is, synthetic siRNA associate with the RISC, unwind, and then associate with complementary mRNA regions of target transcripts, which are then degraded.

An "antioxidant" is a chemical compound or substance that can counteract the damaging effects of oxygen or free radicals in tissues. Examples of antioxidants include amifostine, vitamins A, C and E, 4-hydroxy-2,2,6,6-tetramethylpiperidinyloxy (TEMPOL), and oligomeric proanthocyanidins.

An "immune regulator" is a drug that has the ability to either suppress or stimulate an immune response in a cell. Examples include corticosteroids, GM-CSF, G-CSF, M-CSF, TNFalpha, TNFbeta, interferon alpha, interferon gamma, and any of IL1 through IL13.

An "anti-inflammatory agent" is a compound that suppresses an inflammatory response in an organism.

As used herein, a "heterodimeric molecular complex" is a dimer consisting of two different molecular subunits. The subunits can be polypeptides, and can associate by covalent or non-covalent interactions.

As used herein, "DNA repair" refers to a process by which damage to DNA strands in cells is repaired through any of several known DNA repair mechanism, including base excision repair, nucleotide excision repair, transcription-coupled repair, mismatch repair, translesion synthesis, and homologous recombination (an example of repair of double-stranded DNA breaks). DNA damage can occur through oxidation, alkylation, or hydrolysis of bases, or mismatch of bases during DNA replication.

As used herein, "translesion DNA synthesis" is a form of DNA repair in which specialized, damage-tolerant DNA polymerases (such as Pol eta) bypass DNA lesions that would normally stall replication of a DNA strand, allowing for later repair of the bypassed lesion. These DNA lesions can occur upon cellular exposure to ionizing radiation, ultraviolet light, or DNA-disrupting chemical agents.

As used herein, a "transgenic knockout mouse" is a genetically altered mouse in which a target gene has been replaced with a disrupted form of the gene that persists in subsequent generations of the genetically altered mouse. The gene knockout is generated by selectively disabling a specific target gene in embryonic stem cells. The mouse may have an altered phenotype, such as increased cellular level of monoubiquitinated PCNA, increased cellular level of monoubiquitinated FANCD2, increased cell survival in the presence of Mitomycin C, reduced chromosomal breakage in the presence of Mitomycin C, increased mutation frequency after exposure to UV light, increased DNA replication after exposure to UV light, increased rate of translesion synthesis DNA repair, or increased skin tumorigenicity after exposure to UV light.

As used herein, a "conditional knockout mouse" refers to tissue-specific gene targeting in a transgenic mouse. A gene of interest is knocked out in a particular organ or cell type of interest.

As used herein, the term "deubiquitinase activity of USP1" refers to the action of USP1 to remove ubiquitin. Deubiquitinase activity can be measured by a number of assays including assays that measure the deubiquitination of FANCD2 or PCNA, natural targets of USP1 deubiquitination. Alternatively, the deubiquitinase activity of USP1 can be determined by measuring the deubiquitination of a test molecule such as ubiquitin-7-amido-4-methylcoumarin (Ub-Amc), which produces a fluorescently detectable signal upon the cleavage of ubiquitin. A USP1 polypeptide is deemed to have deubiquitinase activity where the level of deubiquitinated FANCD2, PCNA, or Ub-AMC in the presence of USP1 is at least 10% greater than the level of deubiquitinated FANCD2, PCNA, or Ub-AMC from a similar sample (e.g., sample from the same tissue, or a separate aliquot of a cellular sample) in the absence of USP1. Alternatively a USP1 polypeptide is deemed to have deubiquitinase activity where the level of ubiquitinated FANCD2, PCNA, or Ub-AMC is decreased by at least 10% in the presence of USP1 relative to the absence of USP1. An increase or decrease in USP1 activity in response to an agent as used herein refers to any increase or decrease in the production of a deubiquitinated substrate (i.e., deubiquitinated ubiquitin-7-amido-4-methylcoumarin) in the presence of the agent relative to in the absence of the agent, such as a 0.5% increase or decrease, a 1% increase or decrease, 2%, 3-5%, 5-10%, 10-20%, 20-40%, 40-80%, 90%, or 100% or more increase or decrease in the production of a deubiquitinated substrate.

A "genotoxic agent" or "genotoxin" refers to any chemical compound or treatment method that induces DNA damage when applied to a cell. Such agents can be chemical or radioactive. A genotoxic agent is one for which a primary biological activity of the chemical (or a metabolite) is alteration of the information encoded in the DNA. Genotoxic agents can vary in their mechanism of action, and can include: alkylating agents such as ethylmethane sulfonate (EMS), nitrosoguanine and vinyl chloride; bulky addition products such as benzo(a)pyrene and aflatoxin B1; reactive oxygen species such as superoxide, hydroxyl radical; base analogs such as 5-bromouracil; intercalating agents such as acridine orange and ethidium bromide. A variety of chemical compounds, also described as "chemotherapeutic agents," function to induce DNA damage. Chemotherapeutic agents contemplated to be of use include, e.g., adriamycin, 5-fluorouracil (5FU), etoposide (VP-16), camptothecin, actinomycin-D, mitomycin C, cisplatin (CDDP) and even hydrogen peroxide. "Genotoxic agents" also include radiation and waves that induce DNA damage such as γ-irradiation, X-rays, UV-irradiation, microwaves, electronic emissions, and the like. In addition, certain chemicals, sometimes called indirect genotoxic agents, can be converted into genotoxic agents by normal metabolic enzymes. As used herein, genotoxic agents refer to both direct and indirect genotoxic agents. Genotoxic agents cause mutations in DNA, and can cause cancer. The term "genotoxic agents" also encompasses the use of a combination of one or more DNA damaging agents, whether radiation-based or actual compounds.

Because of the wide diversity of genotoxic agents, exposure to genotoxic agents comes in many different forms. Mechanism of exposure to chemical genotoxic agents may include direct contact, or inhalation by the subject. In the case of radiation, exposure may, arise from proximity to a source of ionizing radiation. The nature of exposure to these genotoxic agents can also vary. Exposure can be deliberate, as is the case with chemotherapy and radiotherapy, but may also be accidental. Examples of accidental exposure may include occupational chemical exposure in a laboratory, factory or farm, or occupational exposure to ionizing radiation in a nuclear power plant, clinic, laboratory, or by frequent airplane travel.

"DNA damage", as used herein, refers to chemical and/or physical modification of the DNA in a cell, including methylation, alkylation double-stranded breaks, cross-linking, thymidine dimers caused by ultraviolet light, and oxidative lesions formed by oxygen radical binding to DNA bases.

As used herein, a "cytoprotective agent" refers to an agent that can increase, or prolong the survival time of a cell or population of cells exposed to a genotoxic agent. A "cytoprotective agent" will increase the survival time of a cell or population of cells by at least 5%, 10%, 20%, 30%, 40%, 50%, 60%, 70%, 80%, 90%, or 100% or more relative to a cell or cell population exposed to a genotoxic agent in the absence of a cytoprotective agent.

Description

The inventors have discovered that inhibition of USP1 deubiquitinase results in increased levels of monoubiquitinated PCNA in eukaryotic cells, leading to enhanced DNA repair activity in the cell nucleus. USP1 is a protease (deubiquitinase) that normally deubiquitinates the monoubiquitinated form of PCNA (PCNA-Ub). Inhibition of USP1 deubiquitinase activity results in increased cellular levels of PCNA-Ub. This improves cell survival by increasing translesion DNA synthesis activity in the cell nucleus. Thus, inhibitors of USP1, through increased DNA translesion synthesis, are radioprotective and chemoprotective to cells.

The inventors have also discovered that the UAF1 protein (WD repeat endosomal protein) is a heterodimeric partner of USP1. It is involved in the DNA damage response in deubiquitinating activity, and in cellular resistance to DNA damage. Since the filing of provisional application No. 60/815,483, to which this application claims priority, the nomenclature has changed and UAF1 is now referred to as USP1 Accessory Factor 1 (UAF1). UAF1 knockdown results in decreased expression of USP1 protein, suggesting that UAF1 is a stabilizing dimeric partner of endogenous USP1. UAF1 knockdown also results in cellular resistance to ionizing radiation (IR) and Mitomycin C (MMC).

The invention also provides a composition consisting of a fragment of USP1 having deubiquitinase activity, PCNA, and an inhibitor of the USP1 fragment or of UAF1 that result in increased levels of ubiquitinated PCNA. One result of increased levels of ubiquitinated PCNA is an increased level of DNA transcription in the cell. One way in which DNA transcription is increased is through increased translesion DNA synthesis.

Design and Selection of siRNA Inhibitors of USP1 Deubiquitinase Activity

Inhibition of USP1 activity may be accomplished, for example, by generating an siRNA that is sufficiently complementary to the mRNA sequence of USP1 or UAF1 to direct RNA interference (RNAi) against the expression of the USP1 gene or the UAF1 gene.

Design of a candidate siRNA can be accomplished, for example, in the following manner: (1) The first "AA" dimer is detected at approximately 75-100 bases distal to the start codon "ATG" of the gene encoding USP1 or UAF1; (2) the next 19 nucleotides are then identified; (3) the percentage of G/C content of the AA-$N_{19}$ 21-base sequence is then determined. The sequence is suitable if the G/C percentage is between 30% and 70%; if the appropriate G/C percentage is not present, the search is repeated distal to the next "AA" dimer; (4) once a suitable candidate sequence is found, a BLAST search is conducted using an Expressed Sequence Tag library to ensure that the sequence will not target a gene other than the one of interest.

A candidate anti-USP1 or anti-UAF1 siRNA can be evaluated for its ability to down-regulate USP1 or UAF1 gene expression. For example, a candidate siRNA can be contacted with a cell that expresses the USP1 or UAF1 gene. The level of USP1 or UAF1 gene expression prior to and following contact with the candidate siRNA can be compared. The level of USP1 or UAF1 RNA or protein in the cell can be determined by any method desired. For example, the level of USP1 RNA can be determined by Northern blot analysis, reverse transcription coupled with polymerase chain reaction (RT-PCR), or RNAse protection assay. The level of protein an be determined by, for example, Western blot analysis. If it is determined that the amount of RNA or protein expressed from the USP1 or UAF1 gene is lower following contact with the siRNA, then it can be concluded that the siRNA down-regulates or inhibits USP1 or UAF1 gene expression.

The siRNA can be tested, for example, in a recombinant cell. The gene encoding USP1 or UAF1 can be fused to a reporter gene on a plasmid and transfected into a cell. Subsequently, a plasmid with the candidate siRNA (directed either to USP1 or UAF1) can transfect the cell. The efficacy of the siRNA agent can be evaluated by monitoring expression of the reporter gene. The reporter gene can be monitored in vivo, such as by fluorescence, luminescence or in situ hybridization. Exemplary reporter genes include but are not limited to green fluorescent protein and luciferase. Expression of the reporter gene can also be monitored by Northern blot, RT-PCR, RNAse-protection assay, or Western blot analysis as described above. An effective siRNA would reveal a measurable reduction in the fluorescence or luminescence of the transfected cells.

Efficacy of an anti-USP1 or UAF1 siRNA agent can be tested in a mammalian cell line. For example, cell lines useful for testing efficacy of an anti-USP1 or UAF1 siRNA include the HeLa and 293T cell lines. Efficacy can also be tested in an animal model, including a transgenic knockout mouse model described below. Efficacy can be evaluated by measuring the levels of ubiquitinated PCNA. The efficacy of a USP1 or UAF1 inhibitor to increase DNA repair activity and hence increase the resistance of a cell to DNA-damaging agents can also be evaluated by measuring cell survival in response to such an agent. Examples of DNA-damaging agents include ultraviolet light, ionizing radiation, antineoplastic drugs, and DNA-damaging chemicals. Examples of such antineoplastic agents include 1,3-bis(2-chloroethyl)-1-nitrosourea (BCNU), busulfan, carboplatin, carmustine, chlorambucil, cisplatin, cyclophosphamide, dacarbazine, daunorubicin, doxorubicin, epirubicin, etoposide, idarubicin, ifosfamide, irinotecan, lomustine, mechlorethamine, melphalan, mitomycin C, mitoxantrone, oxaliplatin, temozolomide, and topotecan.

One control which can be used to test the efficacy and specificity of an siRNA is to assay for a decrease in expression of an off-target gene by, for example, determining its RNA or protein expression. Preferably an siRNA for either USP1 or UAF1 is specific as indicated by greater inhibition of target gene expression than of off-target gene expression. For example, the level of off-target inhibition can be only 1%, 5%, 10%, 20%, 30%, or 50% of the level of target inhibition. Preferably, the level of off-target inhibition is less than 10% of target inhibition; more preferably off-target inhibition is less than 1% of target inhibition. Another control which can be used to test the specificity of an siRNA is to assay for a decrease in expression of the target gene using a "nonfunctional" siRNA, such as LacZ siRNA, which has no homology to any known human gene, or an siRNA whose sequence is nonsensical. In this case, it is preferred that an siRNA for either USP1 or UAF1 is specific as indicated by greater inhibition of target gene by target siRNA than by nonfunctional siRNA. For example, the level of inhibition by nonfunctional siRNA can be only 1%, 5%, 10%, 20%, 30%, or 50% of the level of inhibition by target siRNA. Preferably, the level of inhibition by nonfunctional siRNA is less than 10% of the inhibition by target siRNA; more preferably inhibition by non-functional siRNA is less than 1% of inhibition by target siRNA. The efficacy of target siRNA inhibition can be determined as the percentage decrease in target gene expression, e.g., determined as either mRNA or protein, in the presence of the target siRNA compared to target gene expression in the absence of the target siRNA, or compared to target gene expression in the presence of a nonfunctional siRNA. Preferably, the level of expression of target gene in the presence of target siRNA is between 0 and 80% of the control measured in the absence of siRNA. More preferably, the level of expression of target gene in the presence of target siRNA is between 0 and 50% of the control or between 0 and 20% of the control.

Assays include time course experiments to monitor stability and duration of silencing effect by an siRNA in dividing versus nondividing cells. The dosage may have to be adjusted in vivo. Furthermore, the frequency of administration of an siRNA may have to be adjusted to maintain the silencing effect.

A candidate siRNA can also be evaluated for cross-species reactivity. For example, cell lines derived from different species (e.g., mouse vs. human) or in biological samples (e.g., serum or tissue extracts) isolated from different species can be transfected with a target siRNA and a candidate siRNA. The efficacy of the siRNA can be determined for the cell from the different species.

Examples of siRNA directed to human USP1 are:

```
5'-TCGGCAATACTTGCTATCTTA-3'    (SEQ ID NO: 5)

5'-TTGGCAAGTTATGAATTGATA-3'    (SEQ ID NO: 6)
```

One example of an shRNA directed to human USP1 is:

```
5'-ACAGTTCGCTTCTACACAA-3'      (SEQ ID NO: 7)
```

Suitable siRNA directed to human UAF1 is given by:

```
5'-CCGGTCGAGACTCTATCATAA-3'    (SEQ ID NO: 8)

5'-CACAAGCAAGATCCATATATA-3'    (SEQ ID NO: 9)
```

An example of an shRNA directed to human UAF1 having the sequence:

```
5'-CAAGCAAGATCCATATATA-3'      (SEQ ID NO: 10)
``` siRNA Knockdown of USP1 Results in Increased Mutation Frequency

A supF mutation assay has demonstrated that inhibition of USP1 prolongs error-prone DNA repair, and increases mutation frequency. An siRNA knockdown experiment was conducted in conjunction with a supF shuttle vector in mammalian cells. siRNA knockdown of polymerase eta has been previously been shown to increase the mutation frequency in UV-irradiated supF plasmids (see Choi et al., The role of DNA polymerase eta in UV mutational spectra. DNA Repair 4:211-220 (2005), incorporated herein by reference). In this case, siRNA knockdown of USP1 approximately doubled the mutation frequency in both UV-irradiated and non-irradiated supF plasmids.

Identification of Other Agents that Inhibit USP1 or UAF1

Whether in an in vitro or in vivo system, the invention encompasses methods by which to screen compositions which can inhibit the action of USP1 or UAF1, as well as compositions which enhance DNA damage repair pathways other than translesion DNA synthesis. Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or Myco-Search (NC), or are readily producible by methods well known in the art. Additionally, natural and synthetically produced libraries and compounds are readily modified through conventional chemical, physical, and biochemical means.

Useful compounds may be found within numerous chemical classes, though typically they are organic compounds, including small organic compounds. Small organic compounds have a molecular weight of more than 50 yet less than about 2,500 Daltons, preferably less than about 750, more preferably less than about 350 Daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g., for the amino group, acylation or alkylation, and for the carboxyl group, esterification or amidification, or the like.

Candidate modulators which may be screened according to the methods of the invention include receptors, enzymes, ligands, regulatory factors, and structural proteins. Candidate modulators also include nuclear proteins, cytoplasmic proteins, mitochondrial proteins, secreted proteins, plasmalemma-associated proteins, serum proteins, viral antigens, bacterial antigens, protozoan antigens and parasitic antigens. Candidate modulators additionally comprise proteins, lipoproteins, glycoproteins, phosphoproteins and nucleic acids (e.g., RNAs such as ribozymes or antisense nucleic acids). Proteins or polypeptides which can be screened using the methods of the present invention include hormones, growth factors, neurotransmitters, enzymes, clotting factors, apolipoproteins, receptors, drugs, oncogenes, tumor antigens, tumor suppressors, structural proteins, viral antigens, parasitic antigens, bacterial antigens and antibodies (see below).

Candidate modulators which may be screened according to the invention also include substances for which a test cell or organism might be deficient or that might be clinically effective in higher-than-normal concentration as well as those that are designed to eliminate the translation of unwanted proteins. Nucleic acids of use according to the invention not only may encode the candidate modulators described above, but may eliminate or encode products which eliminate deleterious proteins. Such nucleic acid sequences are antisense RNA and ribozymes, as well as DNA expression constructs that encode them. Note that antisense RNA molecules, ribozymes or genes encoding them may be administered to a test cell or organism by a method of nucleic acid delivery that is known in the art, as described herein. Inactivating nucleic acid sequences may encode a ribozyme or antisense RNA specific for the target mRNA. Ribozymes of the hammerhead class are the smallest known, and lend themselves both to in vitro production and delivery to cells (summarized by Sullivan, (1994) *J. Invest. Dermatol.*, 103: 85S-98S; Usman et al., (1996), *Curr. Opin. Struct. Biol.*, 6: 527-533).

One example of a USP1 inhibitor is ubiquitin aldehyde. In this case, the inhibitor is thought to act by forming a tight complex with the USP1 enzyme, as described in Hershko et al. (Ubiquitin-aldehyde: a general inhibitor of ubiquitin-recycling processes. Proc Natl Acad Sci 1987 April; 84(7): 1829-33), which is incorporated herein by reference. An embodiment comprises the use of combination treatment that includes a known USP1 inhibitor such as ubiquitin aldehyde with another USP1 inhibitor, such as siRNA directed to either USP1 or UAF1, or an antibody directed against USP1 or UAF1.

The invention provides a method of identifying inhibitors of USP1 and/or UAF1 activity in a cell or cell-free system, wherein the method includes testing for the deubiquitination activity of USP1. USP1 deubiquitinating activity can be assayed according to several methods, and it in a preferred embodiment is determined by measuring the deubiquitination of the natural targets of USP1, namely PCNA and FANCD2, or other ubiquitinated targets such as Ub-Amc. Following contacting USP1 (and optionally. UAF1) with a candidate agent in the presence of a ubiquitinated target, samples can be, for example, analyzed by Western analysis using an antibody that specifically binds to the target, wherein the amount of target of a given size (i.e., a size corresponding to a ubiquitinated form vs. an deubiquitinated form) is indicative of the ability of the test agent to being an inhibitor of USP1 deubiquitinase activity. More specifically, a decrease in the amount of deubiquitinated target (i.e., FANCD2, PCNA, or Ub-Amc) is indicative of the compound being an inhibitor of USP1 activity. Assays to determine the deubiquitinase activity of USP1 can be performed in a cell based assay, for example, in which USP1 (and optionally UAF1) are recombinantly expressed in a cell (such as *E. coli*, or SF9 cells) along with the target, or in a cell free assay in which, for example, USP1 (or a USP1/UAF1 complex) is contacted in vitro with a candidate inhibitor in the presence of a ubiquitinated target.

In one embodiment, an assay to identify an inhibitor of USP1 deubiquitination activity includes the steps of contacting a preparation comprising USP1 and UAF1 with a candidate inhibitor in the presence of a ubiquitinated target, preferably Ub-Amc. Cleavage of ubiquitin from Ub-Amc releases the fluorogenic AMC group which can be detected at a flouorescence emission of 460 nm ($\lambda_{ex}$=380 nm). In a further embodiment, the method for identifying an inhibitor of USP1 deubiquitinase activity can be adapted to a high throughput screen to assay more than 1,000, preferably more than 10,000 and still more preferably more than 100,000 reaction sets in duplicate. To perform high throughput screening, it is preferred to conduct the assay using a combination of USP1 and UAF1. As described herein, the invention is based in part on the discovery that UAF1 functions to increase the catalytic activity of USP1. Thus, in the context of high throughput screening, a more robust signal can be generated by assaying for USP1 activity in the presence of UAF1. In addition, variant or mutant forms of USP1 can be used that possess a greater level of activity relative to wild type USP1. For example, mutation of the two glycine residues at amino acid positions 670 and 671 to alanine residues is shown herein to assist in the production and purification of USP1. Optimized methods and reaction conditions are described below in the Examples.

Candidate deubiquitinase inhibitors identified in the screening assays (including high throughput screens) described herein, and be further screened to validate their utility as a USP1/UAF1 inhibitor. It is expected that hits from the primary screen (i.e., high throughput screen) will be typically in the range of 0.5% or more. These positive hits can then be further tested as follows. First the samples can be re-tested to confirm inhibition using the same or similar Ub-Amc assay utilized in the primary screening assay. Following confirmation of inhibitory activity, the compounds can be tested over a range of concentrations to determine dose dependency of inhibition and $IC_{50}$ calculation. Hits that are confirmed via this secondary screening steps can then be tested further for specificity towards USP1/UAF1. Other deubiquitinating enzymes can be tested for inhibition by the candidate using the Ub-AMC activity assay. For example, deubiquitinating enzymes such as USP7, USP2, Isopeptidase T, and Ubiquitin C-terminal hydrolase 1 (UCH-L1) can be tested to confirm that the deubiquitinating inhibitory activity of the candidate is specific for USP1/UAF1. Other deubiquitinating enzymes are known in the art and can also be used to confirm the USP1/UAF1 specificity of the candidate inhibitor. Following confirmation of specificity, a candidate inhibitor can be tested further in a cell based assay to examine USP1 inhibition in vivo using levels of FANCD2-Ub and PCNA-Ub as biomarkers for inhibition. For cell based assays, cells will be treated with the candidate compound(s) and levels of monoubiquitinated FANCD2 and PCNA will be tested both with or without DNA damage. Expected readout of USP1 inhibition will be high level of endogenous monoubiquitinated FANCD2 and PCNA without the DNA damage and this will be persistent long after DNA damage as well. These cell based assays can be performed using methods known in the art and described herein in further detail below. Briefly, for this assay HeLa and HEK293T cells can be treated with a candidate compound and grown in Dulbecco's modified Eagle's medium supplemented with 15% heat-inactivated fetal calf serum in a humidified 5% $CO_2$ incubator at 37° C. Damage can be induced by UV irradiation using Stratalinker (Stratagene) and/or treatment with Mitomycin C (MMC, Sigma). After cell lysis, levels of monoubiquitinated FANCD2 and PCNA in whole cell lysate can be tested by immunoblotting with anti-FANCD2 antibody (FI-17) (Santa Cruz Biotechnology) and anti-PCNA antibody. Protection from Chromosome aberrations will also be tested in UV/MMC damaged cells treated with potential USP1 inhibitors using standard chromosome breakage assay (Yang et al., 2001, Blood 98:3435-40).

In addition to the foregoing, candidate USP1/UAF1 inhibitors can be screened to elucidate their mechanism of action. Potential inhibitors of USP1/UAF1 complex can inhibit the deubiquitinating activity by a number of different mechanisms. Crystal structures of USP7 and USP2 showed that ubiquitin binds to the enzyme via hydrogen bonding interactions with water molecules present in some specific pockets in enzyme. Therefore, inhibition may occur due to binding of the inhibitor in these water-binding pockets far away from the enzyme active sites. Also, UAF1 binding enhances USP1 enzyme activity by several folds suggesting a probable conformational change in USP1 after UAF1 binding may lead to an efficient conformation for catalysis. Inhibitor may also bind to such an allosteric site and may prevent the catalytically efficient conformational switch. These mechanisms of action can be tested by using a small substrate Gly-Gly-AMC (Boston Biochem, MA) instead of large ubiquitin conjugated AMC. If the candidate compound is active site inhibitor, then USP1 will fail to cleave Gly-Gly-AMC, but if the small inhibitor binds to a site away from the active site, then the USP1 enzyme will be fully active with Gly-Gly-AMC but not with Ub-AMC. Also, standard enzyme assays known in the art can be carried out to determine competitive or non-competitive nature of inhibition.

The compositions and methods of this invention may be used in conjunction with other compounds to test their efficacy in increasing cellular levels of monoubiquitinated PCNA. A USP1 inhibitor is identified if the rate or amount of deubiquitination is reduced in the presence of the test compound. An inhibitor of UAF1 can be identified if the presence of the putative UAF1 inhibitor results in a reduced rate or amount of deubiquitination of PCNA. The ability of a test compound to protect a cell against the DNA damaging effects of ultraviolet light, ionizing radiation or a DNA disrupting chemical compound can further be tested by treating a population of cells with the compound, exposing them to the DNA damaging agent, and measuring the level of cell survival at different levels of exposure to the agent. A putative USP1 inhibitor may then be added to a suitable mixture of USP1 and PCNA.

A recombinant cell can be developed that expresses siRNA directed against the gene encoding USP1 or UAF1. Recombinant cells having different levels of USP1 deubiquitinase activity can be generated. A panel of biomarkers associated with recombinant cells having different levels of deubiquitinase activity can be developed, allowing for the determination of the sensitivity of a cell to radiation or DNA-damaging chemical agents, or to mutation frequency.

Diagnostic Methods

In addition to providing methods for the identification of inhibitors of USP1 deubiquitinase activity, the present invention provides methods for diagnosing a patient as having cancer, an increased susceptibility to cancer, or an increased radiation sensitivity. As described herein, USP1 is a deubiquitinating enzyme that negatively controls the cellular levels of the DNA damage response proteins FANCD2-ub and PCNA-ub, key proteins in the Fanconi anemia Pathway and the Trans lesion synthesis pathway, respectively. Increased activity of USP1/UAF1 results in greater numbers of deubiquitinated FANCD2 and PCNA molecules, resulting in decreased DNA repair. These DNA repair pathways are important cellular determinants of cellular sensitivity to ionizing radiation as well as the body's ability to repair mutations that potentially give rise to cancer. Accordingly, the activity of USP1 and/or UAF1, and/or the extent of interaction between USP1 and UAF1 can be diagnostic for a patient's cancer status, susceptibility to cancer, or sensitivity to ionizing radiation (or resistance, or lack thereof, to radiation)

In one embodiment, the invention provides a method for diagnosing cancer in an individual or determining an individual's susceptibility to cancer, or determining the individual's radiation sensitivity (or level of radiation resistance), whereby the level of USP1/UAF1 activity and/or amount of USP1/UAF1 in a cell is determined, wherein a greater level of activity and/or increased levels of USP1/UAF1 protein is indicative of cancer in an individual, increased cancer susceptibility, and/or increased radiation sensitivity.

USP1/UAF1 activity can be measured by any of the assays described herein. For example, activity can be measured by measuring the level of deubiquitinated target protein in response to USP1/UAF1 (that is, for example, the conversion of Ub-Amc to AMC). USP1/UAF1 levels can be measured by any one of several methods known in the art. For example, antibodies that specifically bind to USP1 or UAF1 can be used to determine the levels of USP1 or UAF1 protein present in a cell or patient sample. Alternatively, molecular methods such as PCR, QPCR, Southern analysis, and Northern analysis can be used to determine the levels of nucleic acid encoding USP1 or UAF1, indicative of the levels of USP1 or UAF1 present in a cell or patient sample. Immunohistochemical and other antibody-based assays, as well as methods for nucleic acid analysis are well known in the art. A patient is diagnosed as having cancer, having increased suscepability to cancer, or having increased radiation sensitivity if the level of USP1/UAF1 protein (and/or nucleic acid) is increased by at least 10% relative to control, preferably decreased by 10-100%, preferably 20-200%, 30-100%, 40-100%, 50-80%, at least 20%, 30%, 50%, 70% 90% or 100% or more.

In addition, the invention provides methods for diagnosing cancer in an individual or determining an individual's increased cancer susceptibility or radiation sensitivity by measuring the interaction between USP1 and UAF1, wherein an increased level of interaction (e.g., binding) between USP1 and UAF1 is indicative of the individual having cancer, increased cancer susceptibility, or increased radiation sensitivity. The interaction between USP1 and UAF1 can be measured by numerous methods known to those of skill in the art. For example, each of USP1 and UAF1 can be bound by specific antibodies that are labeled with members of an interactive pair of labels, such as a FRET donor and acceptor, or a fluorophore and quencher, wherein there is a change in a detectable signal upon the interaction of USP1 with UAF1. Alternatively, or in addition, biophysical measurements can be made, such as surface plasmon resonance measurements or other measurements which utilize a change in the mass of either protein (e.g., USP1) in response to interaction with the other protein (e.g., UAF1). A patient is diagnosed as having cancer, having increased suscepability to cancer, or having increased radiation sensitivity, if the level of interaction between USP and UAF1 is increased by at least 10% relative to control, preferably decreased by 10-100%, preferably 20-200%, 30-100%, 40-100%, 50-80%, at least 20%, 30%, 50%, 70% 90% and at least 100% or more. level of USP1/UAF1 protein (and/or nucleic acid) is decreased by at least 10% relative to control, preferably decreased by 10-100%, preferably 20-200%, 30-100%, 40-100%, 50-80%, at least 20%, 30%, 50%, 70% 90% and increased by 100% or more.

Animal Models in which USP1 or UAF1 Activity is Inhibited

The invention includes a transgenic knockout mouse whose genome has been altered to result in downregulation or inhibition of the expression of the USP1 or UAF1 gene. Examples include a transgenic knockout mouse whose phenotype shows evidence of increased DNA transcription or repair, increased level of ubiquitinated PCNA, increased resistance to ultraviolet light, increased resistance to ionizing radiation, increased resistance to an antineoplastic agent, and increased mutation rate. The approach to producing a transgenic mouse model is as follows:

a. Introducing a USP1 targeting vector into a mouse embryonic stem cell;
b. Introducing the treated stem cell into a mouse blastocyst;

c. Transplanting the blastocyst into a pseudopregnant mouse;
d. Allowing the transplanted blastocyst to develop to term;
e. Verifying that the newborn mouse's genome has been altered so that the expression of USP1 has been suppressed;
f. Breeding the resulting transgenic mouse and verifying that this mouse line possesses an altered phenotype compared to a wild-type mouse.

A conditional murine knockout model of USP1 has been generated. The murine genomic clone for USP1 has been identified and isolated. The murine gene spans 100 kb, consists of 9 protein-encoding regions, and maps to chromosome 4. A USP1 targeting vector with a foxed exon 3 has been generated. Floxed exon 3 has been readily removed from the vector. Thus a conditional allele was created without affecting expression of the USP1 gene until the floxed exon is removed. The neomycin resistance cassette was removed, because it contains a strong eukaryotic promoter. The foxed targeting vector was transfected into embryonic stem cells. Two karyotypically normal embryonic stem cell clones, with proper targeting, were identified and injected into blastocysts. For one embryonic stem cell clone (#923, flp 31), seven high percentage chimeric mice were generated. For the other embryonic stem cell clone (#923, flp 20), five high percentage chimeric mice were generated. Breeding pairs of mice that are heterozygous for the USP1 mutant allele, USP1(+/−), were established, as well as colonies containing USP1(−/−) mice. These mice can be systematically crossed with Cre-expressing mice, and the effects of USP1 knockout in different tissues can be ascertained. From this model, it is possible to determine whether USP1 knockdown results in the predicted increase in baseline translesion DNA synthesis, based on increased PCNA-Ub/Pol eta complexes.

The murine model provides a platform to study the role of USP1 in vivo. The mice may be tested for total body Ultraviolet radiation, ionizing radiation and antineoplastic drug sensitivity (such as MMC), as well as mutation frequency, compared to wild-type and heterozygote USP1 control mice. The mice may exhibit an altered phenotype selected from the group consisting of increased cellular level of monoubiquitinated PCNA, increased cellular level of monoubiquitinated FANCD2, increased cell survival in the presence of Mitomycin C, reduced chromosomal breakage in the presence of Mitomycin C, increased mutation frequency after exposure to UV light, increased DNA replication after exposure to UV light, increased rate of translesion synthesis DNA repair, and increased skin tumorigenicity after exposure to UV light. These assay methods have been described in Yang et al. (Targeted disruption of the murine Fanconi anemia gene, Fancg/Xrcc9, Blood, 1 Dec. 2001; 98(12): 3435-40), which is incorporated herein by reference. Mutation frequency may be determined with the SUP-F assay by methods previously described for Xpg-deficient mice, such as Shiomi et al. (Disruption of Xpg increases spontaneous mutation frequency, particularly A:T to C:G transversion, Mutat Res. 2001 Dec 19; 487(3-4): 127-35), which is incorporated herein by reference. The cells of these mice may also be evaluated by Western blot for expression of USP1 and PCNA-Ub levels. Wild-type and heterozygote cells may be used as controls. A knockout mouse whose expression of USP1 is substantially (about 90% or greater) disrupted, if exposed to 32 J/m$^2$ of UV-B daily for one year, is expected to exhibit about 100-fold more skin tumors, after a latency period of at least 25 weeks, than a wild type mouse.

One composition of this invention comprises isolated USP1 and PCNA polypeptides. The polypeptides are present at a PCNA:USP1 molar ratio in the range of from 0.1:1 to about 1,000,000:1 or higher. UAF1 may also be added to the composition, as the inventors have discovered that the UAF1 protein is a heterodimeric partner of USP1, enhancing its deubiquitinating activity. Preferably, the molar ratio of USP1 to UAF1 is about 1:1, but it can be in the range from 1:100 to about 100:1. The combination of USP1 and PCNA, with or without UAF1, results in decreased levels of PCNA. Adding a USP1 inhibitor to this composition results in increased levels of ubiquitinated PCNA ("PCNA-Ub").

This invention also encompasses a cellular composition comprising USP1 and PCNA with or without UAF1, to which is added either a USP1 inhibitor or UAF1 inhibitor, resulting in increased levels of PCNA-Ub. This composition further results in increased DNA transcription in the cell. One way in which DNA transcription is increased is through increased DNA translesion synthesis. One way in which USP1 or UAF1 may be inhibited is through the use of siRNA directed to the USP1 gene or the UAF1 gene, or both. Any of these compositions are thus capable of increasing cellular resistance to DNA-damaging agents, which may include ultraviolet radiation ("UV"), ionizing radiation ("IR"), chemotherapeutic agents or other chemical agents.

Treatment and Prevention of DNA Damage

The utility of the compositions of the present invention may be demonstrated as radioprotective agents both in vitro and in vivo. The compositions of this invention are useful in treating conditions in which the level of cellular DNA repair activity is impaired. This invention can be used as a method of increasing the level of DNA transcription activity in a cell by administering an effective amount of an inhibitor of USP1 or UAF1. The increased DNA transcription activity can occur, for example, through increased DNA translesion synthesis. One method of increasing DNA translesion synthesis is to introduce an siRNA that reduces the expression of the gene for USP1 or UAF1.

USP1 inhibitors and UAF1 inhibitors are therefore useful for subjects who are at risk of being exposed to, or have been exposed to radiation. Treating a subject with a USP1 inhibitor or UAF1 inhibitor will be useful for situations in which he or she may be exposed to UV light, X-rays, gamma rays, a particle beam, cosmic rays; radiation from industrial, research or medical equipment, a nuclear reactor, or from an explosive device, radioactive fallout from a nuclear accident or explosion, and radiation exposure from mines mineral refineries, industrial plants or space travel.

The compositions can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. Examples of USP1/UAF1 inhibitory compounds that may be administered according to the methods of the invention include β-Lapachone, Biomol AP401, and RK-682. The compounds of the invention, while effective themselves, may be formulated and administered in the form of their pharmaceutically acceptable acid addition salts for purposes of stability, convenience of crystallization, increased solubility and the like. The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

Treatment of Neoplastic and Other Diseases

The administration of the compositions of present invention may be for either prevention or treatment purposes. Administering an effective amount of USP1 inhibitor or UAF1 inhibitor provides a cytoprotective effect from an antineoplastic treatment. The methods and compositions used herein may be used alone or in conjunction with additional therapies known to those skilled in the art in the prevention or treatment of radiation therapy or cancer chemotherapy-induced cellular damage. Alternatively, the methods and compositions described herein may be used as adjunct therapy. By way of example, the USP1 or UAF1 inhibitor may be administered alone or in conjunction with other antineoplastic agents, anti-inflammatory agents or antioxidant agents, other cell-protective agents or other drugs or nutrients. The administration of the present invention may also be used to increase the range of dosage, the duration or the frequency of dosing of an antineoplastic agent.

Examples of neoplastic diseases for which this invention may be administered in conjunction with an antineoplastic agent include leukemias such as, but not limited to, acute lymphoblastic, acute myelogenous, chronic lymphocytic, acute myeloblastic and chronic myelocytic; carcinomas, such as, but not limited to, those of the cervix, esophagus, stomach, pancreas, breast, ovaries, small intestines, colon and lungs; sarcomas, such as, but not limited to, osteosarcoma, lipoma, liposarcoma, hemangioma and hemangiosarcoma; melanomas, including amelanotic and melanotic; and mixed types of neoplasias such as, but not limited to carcinosarcoma, lymphoid tissue type, folicullar reticulum, cell sarcoma, Hodgkin's disease and non-Hodgkin's lymphoma.

There are large numbers of antineoplastic agents available in commercial use, in clinical evaluation and in pre-clinical development, which could be selected for treatment of angiogenesis by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplalstic agents, such as metallomatrix proteases inhibitors (MMP), such as MMP-13 inhibitors including batiastat, marimastat. Agouron Pharmaceuticals AG-3340, and Roche R0-32-3555, or alpha, beta, inhibitors may be used.

A first family of antineoplastic agents which may be used in combination with a selective cyclooxygenase-2 inhibitor consists of antimetabolite-type antineoplastic agents. Suitable antimetabolite antineoplastic agents may be selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku F0-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

A second family of antineoplastic agents which may be used in combination with a selective cyclooxygenase-2 inhibitor consists of alkylating-type antineoplastic agents. Suitable alkylating-type antineoplastic agents may be selected from the group consisting of Shionogi 254-S, aldophosphamide analogues, altretamine, anaxirone, Boehringer Mannheim BBR-2207, bestrabucil, budotitane, Wakunaga CA-102, carboplatin, carmustine Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic. Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with a selective cyclooxygenase-2 inhibitor consists of antibiotic-type antineoplastic agents. Suitable antibiotic-type antineoplastic agents may be selected from the group consisting of Taiho 4181-A, aclarubicin, actinomycin D, actinoplanone, Erbamont ADR.sup.456, aeroplysinin derivative, Ajinomoto AN-201-II. Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b. Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin. siwenmycin, Surmitomo SM-5887, Snow Brand SN-706, Snow Brand SN-07, sorangicin-A, sparsomycin. SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A. Upjohn U-73975, Kyowa Hakko UCN-10028A, Fujisawa WF-3405, Yoshitomi Y-2S024 and zorubicin.

A fourth family of antineoplastic agents which may be used in combination with the selective cyclooxygenase-2 inhibitor consists of a miscellaneous family of antineoplastic agents selected from the group consisting of alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston AIO, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-1OO, Warner-Lambert CI-921, Warner-Lambert CI-937. Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didernin-B, dihaematoporphirin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross H0-221, homoharringtonine, hydroxyurea, BTG ICRF-187, ilmofosine, isoglutamine, isotretinoin. Otsuka JI-36, Ramot K-477, Otsuak K-76COONa, Kureha Chemical K-AM, MECT Corp KI-8110, American Cyanamid L-623, leukoregulin, Ionidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112. oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglurnide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, kyowa Hakko UCN-O1, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

The compositions of this invention may also be used in combination with agents such as other radioprotective agents, antioxidants, immune regulators, and anti-inflammatory agents. Examples of other radioprotective agents, i.e., those which act by a mechanism different from inhibition of USP1 deubiquitinase activity, which may be used in the combination therapy of this invention are AD-5, adchnon, amifostine analogues, detox, dimesna, I-102, MN-159, N-acylated-dehydroalanines, TGF-Genentech, tiprotimod, amifostine, WR-1511327, FUT-187, ketoprofen transdermal, nabumetone, and superoxide dismutase.

It is further envisioned that a USP1 inhibitor or UAF1 inhibitor may be used in cancer therapies that include the use of antibodies, antibody fragments or recombinant proteins, as well as any combination of such agents with other antineoplastic compounds, and radiation therapy.

The efficacy of cancer treatment involving administration of an inhibitor of USP1 deubiquitinase activity can be assessed in a number of different ways. The average size or range of sizes of solid tumors can be measured using standard anatomical or histochemical techniques. At a chosen time after administration of an inhibitor, or combination therapy including an inhibitor, the tumor size is determined. An effective inhibitor causes tumor size to shrink to about 80% to about 0% of the starting size or the size of control tumors not treated with the inhibitor. Preferably, an effective inhibitor causes tumor size to shrink to less than 50% of the starting size or control size.

Dosing, Administration, and Formulation

The method of the invention involves administering an effective amount of a compound which is an inhibitor of USP1 deubiquitinase activity. While an effective dosage can be routinely determined for a given deubiquitinase inhibitor compound, a typical dosage for a human is in the range of 0.001 to 100 mg/kg/day, preferably 0.01 to 10 mg/kg/day or 0.1 to 1 mg/kg/day.

Typically a USP1 deubiquitinase inhibitor compound is administered together with one or more formulation ingredients, such as one or more pharmaceutically acceptable carriers. Pharmaceutically acceptable carriers include pharmaceutical diluents, excipients, and buffers, suitably selected with respect to the intended form of administration, and consistent with conventional pharmaceutical practices. For example, solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof. Pharmaceutically acceptable carriers can be aqueous or non-aqueous solvents. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media.

The compounds for use in the method of the invention can be formulated for administration by any suitable route, such as for oral, parenteral, or topical; for example, transdermal, transmucosal (e.g., sublingual, lingual, buccal), vaginal, nasal and rectal, subcutaneous, intramuscular, intradermal, intraarterial, intravenous, and inhalation administration may be used.

Suitable compositions and dosage forms include tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays, dry powders, and aerosolized formulations.

Oral administration of the USP1 deubiquitinase inhibitor is preferred. Suitable oral dosage forms include, for example, tablets, capsules, and caplets prepared by conventional means with pharmaceutically acceptable excipients such as binding agents (e.g., polyvinylpyrrolidone or hydroxypropylmethylcellulose); fillers (e.g., lactose, microcrystalline cellulose or calcium phosphate); lubricants (e.g., magnesium stearate, talc or silica); disintegrants (e.g., sodium starch glycolate); or wetting agents (e.g., sodium lauryl sulfate). Tablets can be coated, e.g., to provide for ease of swallowing or to provide a delayed release of active, using suitable methods. Liquid preparations for oral administration can be in the form of solutions, syrups, or suspensions. Liquid preparations (e.g., solutions, suspensions, and syrups) are also suitable for oral administration and can be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Pharmaceutically acceptable salts of a compound to be administered can be prepared from pharmaceutically acceptable non-toxic acids including inorganic acids, organic acids, solvates, hydrates, or clathrates thereof. Examples of such inorganic acids are hydrochloric, hydrobromic, hydroiodic, nitric, sulfuric, and phosphoric acids. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

USP1 deubiquitinase inhibitor compounds can be prepared in the form of their hydrates, such as hemihydrate, monohydrate, dihydrate, trihydrate, tetrahydrate and the like and as solvates. They can also be prepared in the form of an ester prodrug which is cleaved in the body to release the active compound.

In some embodiments, an amount of another suitable therapeutic, for example a small molecule chemotherapeutic drug, a radioprotective agent, or an antioxidant, is combined with the administration of one or more USP1 deubiquitinase inhibitors. In certain embodiments, a USP1 deubiquitinase inhibitor and another suitable therapeutic are each administered in an effective amount, i.e., each in an amount which would be therapeutically effective if administered alone. Effective amounts of co-therapeutic drugs, such as chemotherapeutics, radioprotectants, and antioxidants, are well known in the art. In other embodiments, a USP1 deubiquitinase inhibitor and a suitable co-therapeutic are each administered in an amount which alone does not provide a therapeutic effect (a sub-therapeutic dose). In yet another embodiment, the USP1 deubiquitinase inhibitor can be administered in a therapeutically effective amount, while the suitable co-therapeutic is administered in a sub-therapeutic dose. In still another embodiment, the USP1 deubiquitinase inhibitor can be administered in a sub-therapeutic dose, while the suitable *** therapeutic is administered in a therapeutically effective amount. In general, the ratio of the USP1 deubiquitinase inhibitor to the co-therapeutic, in terms of the therapeutically effective dose of each drug given alone, can be, for example, in the range of about 1:1000, 1:100, 1:50, 1:10, 1:1, 10:1, 50:1, 100:1, or 1000:1 on a weight basis. It is understood that the method of coadministration of a first amount of a USP1 deubiquitinase inhibitor and a second amount of a suitable co-therapeutic can result in an enhanced or synergistic therapeutic effect, wherein the combined effect is greater than the additive effect that would result from separate administration of the first amount of the USP1 deubiquitinase inhibitor and the second amount of the suitable co-therapeutic. A synergistic effect can be, for example, an increase of 3-fold, 10-fold, 100-fold or greater therapeutic effect than the sum of the therapeutic effects expected from administering each agent separately. Where synergistic effects are encountered, the dosage of each individual drag in the combination can be varied so as to achieve the desired effect.

EXAMPLES

Example 1

Identification of USP1 Interacting Protein UAF1

The following experiments describe the purification of the USP1 enzyme with associated proteins from human HeLa cells. A native multisubunit protein complex was isolated containing stoichiometric amounts of an 80 kDa protein, which was named USP1 Associated Factor 1 (UAF1). UAF1 is a WD40 repeat containing protein, which regulates both the stability and the activity of USP1.

Cell Lines, Antibodies and Plasmids

HeLa and HEK293T cells were grown in DMEM (Invitrogen) supplemented with 10% FBS. Stable HeLa cells expressing a UAF1 knock down plasmid were generated using the pSUPER.retro (Clontech) vector harboring the following UAF1 target sequence: 5'-CAAGCAAGATC-CATATATA-3' (SEQ ID NO: 10). Antibodies used were as follows: anti-USP1 antibody (Nijman, S. M., Huang, T. T., Dirac, A. M., Brummelkamp, T. R., Kerkhoven, R. M., D'Andrea, A. D., and Bernards, R. (2005a). The deubiquitinating enzyme USP1 regulates the Fanconi anemia pathway. Mol Cell 17, 331-339); anti-FANCD2 (sc-20022; Santa Cruz Biotechnology, Inc.); anti-PCNA (sc-56; Santa Cruz Biotechnology, Inc.); anti-gamma-Tubulin (CP06; Calbiochem); anti-c-Myc (sc-40; Santa Cruz Biotechnology, Inc.); anti-HA (mouse monoclonal antibody clone 12CA5); anti-UAF1 rabbit polyclonal antibodies were raised by immunizing a rabbit with an N-terminal His-tagged fusion protein containing amino acids 400-677 of UAF1 according to standard immunology methods (Harlow, E., and Lane, D. (1988). Antibodies: a laboratory manual (Cold Spring Harbor, N.Y., Cold Spring Harbor Laboratory)).

Flag-HA-tagged USP1, UAF1 and FANCD2 were expressed using the pOZ-N plasmid (Nakatani, Y., and Ogryzko, V. (2003). Immunoaffinity purification of mammalian protein complexes. Methods Enzymol 370, 430-444). Flag-tagged UAF1 deletion constructs were expressed using the pcDNA3.1 plasmid (Invitrogen). UAF1-ΔWD2, UAF1-ΔWD2-4, UAF1-Δ507-546, UAF1-4546-585, UAF1-Δ635-677 carry deletions of aa xxx and xxx 507-546, 546-585, 635-677, respectively. shRNA mediated knockdown of the UAF1 gene was achieved by expressing the target sequences GGACCGAGATTATCTTTC (SEQ ID NO: 11) (#1) and CAAGCAAGATCCATATATA (SEQ ID NO: 10) (#2) in the pSuper.retro vector (Clontech).

Mass Spectrometric Analysis

Proteins were reduced with DTT, cysteine residues were derivatized with iodoacetamide and the proteins were separated by SDS-PAGE. Proteins from Coomassie-stained gel bands were in-gel digested with trypsin (Shevchenko, A., Wilm, M., Vorm, O., and Maim, M. (1996). Mass spectrometric sequencing of proteins silver-stained polyacrylamide gels. Anal Chem 68, 850-858). The generated peptide mixtures were subjected to LC-MS/MS using a hybrid linear ion trap/FT-ICR mass spectrometer (LTQ FT, Thermo Electron) essentially as described previously (Haas, W., Faherty, B. K., Gerber, S. A., Elias, J. E., Beausoleil, S. A., Bakalarski, C. E., Li, X., Villen, J., and Gygi, S. P. (2006). Optimization and use of peptide mass measurement accuracy in shotgun proteomics. Mol Cell Proteomics 5, 1326-1337). MS/MS spectra were assigned by searching them with the SEQUEST algorithm (Eng, J. K., McCormack, A. L., and Yates, J. R., 3rd (1994). An approach to correlate tandem mass spectral data of peptides with amino acid sequences in a protein database. J Am Soc Mass Spectrom 5, 976-989) against the human International Protein Index sequence database.

Protein Purification

The USP1 complex was purified from nuclear extracts prepared from HeLa cells expressing N-terminal Flag- and HA-epitope tagged USP1 as described (Nakatani and Ogryzko, 2003). N-terminal Flag- and HA-epitope tagged UAF1 and FANCD2 proteins were purified by the same method, although more stringent washes including 0.5M KCl were applied during the purification procedures to obtain proteins purified to homogeneity. Monoubiquitinated FANCD2 protein was purified from cells treated with 2 mM hydroxyurea for 24 h.

Transient transfection of 293T cells for IP experiments was performed using Fugene 6 (Roche) according to manufacturer's instructions.

Proteins purified from Sf9 cells were expressed using either the pFastBac-HTa vector (Invitrogen) containing an N-terminal His tag (for USP1) or the pFastBac-1 vector (Invitrogen) with an engineered C-terminal Strep II tag (for UAF1). For USP1 and USP1/UAF1 complex purification, cell pellets were re-suspended in lysis buffer (50 mM Tris-HCl, pH 8.0, 150 mM NaCl, 10 mM BME, 10 mM imidazole, 10% glycerol and 0.2% Triton X-100) and sonicated to lyse. Lysates were centrifuged and the supernatants were incubated with Ni-NTA agarose resin (Qiagen) for 1 hour. The resin was washed extensively and the proteins eluted in elution buffer (50 mM Tris-HCl, pH 8.0, 100 mM NaCl, 10 mM BME, 10% glycerol and 250 mM imidazole). Eluted protein was bound to a 5 mL HiTrap Q-FF cartridge (GE Biosciences), washed with washing buffer (50 mM Tris-HCl, pH 8.0, 100 mM KCl, 5 mM DTT, 0.1 mM EDTA and 10% glycerol) and eluted in the same buffer containing 500 mM KCl. For UAF1 purification, cells were re-suspended in lysis buffer (50 mM Tris-HCl, pH 8.0, 150 mM NaCl, 2 mM DTT, 10% glycerol), centrifuged, and the clarified lysate was incubated for 1 hour with the Strep-Tactin resin (Novagen). Following incubation, the resin was washed extensively and the protein eluted in the same buffer containing 2.5 mM desthiobiotin.

In Vitro Enzymatic Assays

Transcription/translation in rabbit reticulocyte was performed according to manufactures recommendations with the exception that the reactions were performed at 30° C. (Promega). In vitro enzymatic assays in the presence of 5 µM Ubiquitin-VS (Ubiquitin-Vinyl Sulfone; U-202; Boston Biochem) were performed 30° C. In vitro enzymatic assays using Ubiquitin-AMC (Ubiquitin-7-amido-4-methylcoumarin; U-550; Boston Biochem) were performed in 50-100 µl reaction buffer (20 mM HEPES-KOH pH 7.8, 20 mM NaCl, 0.1 mg/ml Ovalbumin (A7641; Sigma), 0.5 mM EDTA and 10 mM DTT) at 37° C. Fluorescence was monitored in a FluoStar Galaxy Fluorometer (BMG Labtech Inc.). In vitro deubiquitination reactions of Ub-FANCD2 were performed in 10 µl reaction buffer (90 mM Tris-HCl pH 8.0, 50 mM NaCl, 0.03% NP-40, 4 mg/ml BSA and 2 mM DTT) for 2 h at 30° C.

Northern Blot Analysis

Northern blot analysis was performed as described using the 394nt PstI-EcoRV fragment of the USP1 cDNA (Cohn, M. A., Kramerov, D., Hulgaard, E. F., and Lukanidin, E. M. (1997). The differentiation antigen Ly-6E.1 is expressed in mouse metastatic tumor cell lines. FEBS Lett 403, 181-185).

Purification of the Native USP1/UAF1 Complex

To further explore the mechanism of USP1-mediated deubiquitination of Ub-FANCD2, the USP1 enzyme was purified with associated proteins as a native protein complex from HeLa cells. A HeLa cell line stably expressing a Flag- and HA-epitope tagged fusion protein of USP1 (e-USP1) was generated by retroviral transduction. The exogenous e-USP1 protein was expressed at levels comparable to the endogenous protein and also underwent autocleavage, a feature previously reported for the USP1 protein (Huang et al., 2006; Nijman et al., 2005). Taken together, our results demonstrate that the epitope tagged USP1 protein is functional (data not shown).

Nuclear extract was prepared from HeLa cells, and the native USP1 complex was purified by a two step immunoaffinity purification scheme (Nakatani and Ogryzko, 2003). SDS-PAGE analysis of the purified complex demonstrated the presence of multiple polypeptides (FIG. 1A, lane 2). No polypeptides were observed in a mock purification from untransduced HeLa cells, indicating that all polypeptides copurifying with e-USP1 were bona fide subunits of the USP1 complex (FIG. 1A, lane 1). Mass spectrometric analysis of the polypeptides identified full length USP1, the N-terminal cleavage product of USP1, and the C-terminal cleavage product of USP1. A fourth major polypeptide, with a molecular weight of 80 kDa, was identified as the previously studied p80 protein (Park, J., Lee, B. S., Choi, J. K., Means, R. E., Choe, J., and Jung, J. U. (2002). Herpesviral protein targets a cellular WD repeat endosomal protein to downregulate T lymphocyte receptor expression. Immunity 17, 221-233). We now refer to this protein as UAF1 (USP1 Associated Factor 1). UAF1 contains 677 amino acids and harbors 7 or 8 potential WD40-repeats in the N-terminal half and a predicted coiled coil structure in the C-terminal half. Tertiary structure prediction using the Phyre software, available on the world wide web at sbg.bio.ic.ac.uk/~phyre, suggests the presence of a complete propeller structure comprised by the WD40 repeats. The intensities of Coomassie blue stained USP1 and UAF1 proteins in the SDS-PAGE were nearly identical, suggesting stoichiometric amounts of the two proteins in the complex and a possible functional relationship.

Figure 1B:
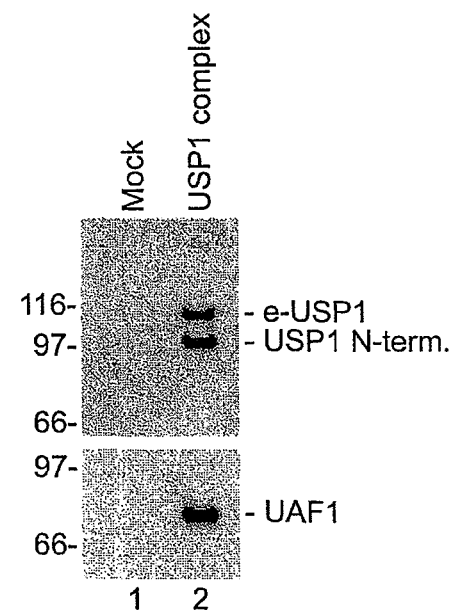

The protein subunits in the USP1 complex were analyzed by immunoblotting, using antibodies to the USP1 protein (Nijman et al., 2005) and newly generated antibodies against the UAF1 protein. The results confirmed the presence of full length USP1, N-terminal USP1, and UAF1 in the USP1 complex, in good correlation with the Coomassie blue stain of the complex (FIG. 1B).

Figure 1C:
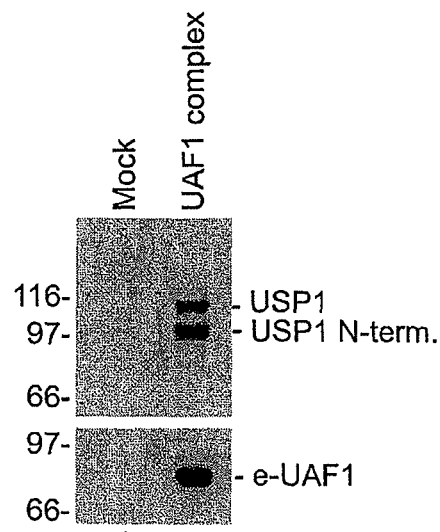
Figure 1D:
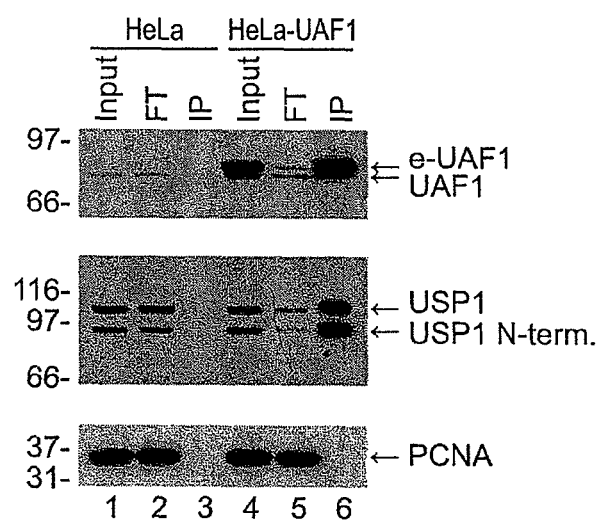

Flag-HA-tagged UAF1 were expressed in HeLa cells and the protein was immunoprecipitated with associated proteins. Immunoblotting of the immunoprecipitate revealed the presence of endogenous USP1 as well as its cleavage product, confirming the presence of a native USP1/UAF1 complex (FIG. 1C). Since both full length and the N-terminal cleavage products of USP1 were detected in the UAF1 immunoprecipitate, we concluded that both forms can interact with UAF1. Together with the presence of the C-terminal cleavage productlin the USP1 complex (FIG. 1A), the data suggest that a ternary complex of the two cleavage products of USP1 and the UAF1 protein exists after USP1 is autocleaved. The majority of USP1 protein in the HeLa cells was observed to exist as a protein complex with UAF1 (FIG. 1D), further underscoring the importance of the USP1/UAF1 complex.

UAF1 Stabilizes USP1 In Vivo and In Vitro

Figures 2A, 2B:
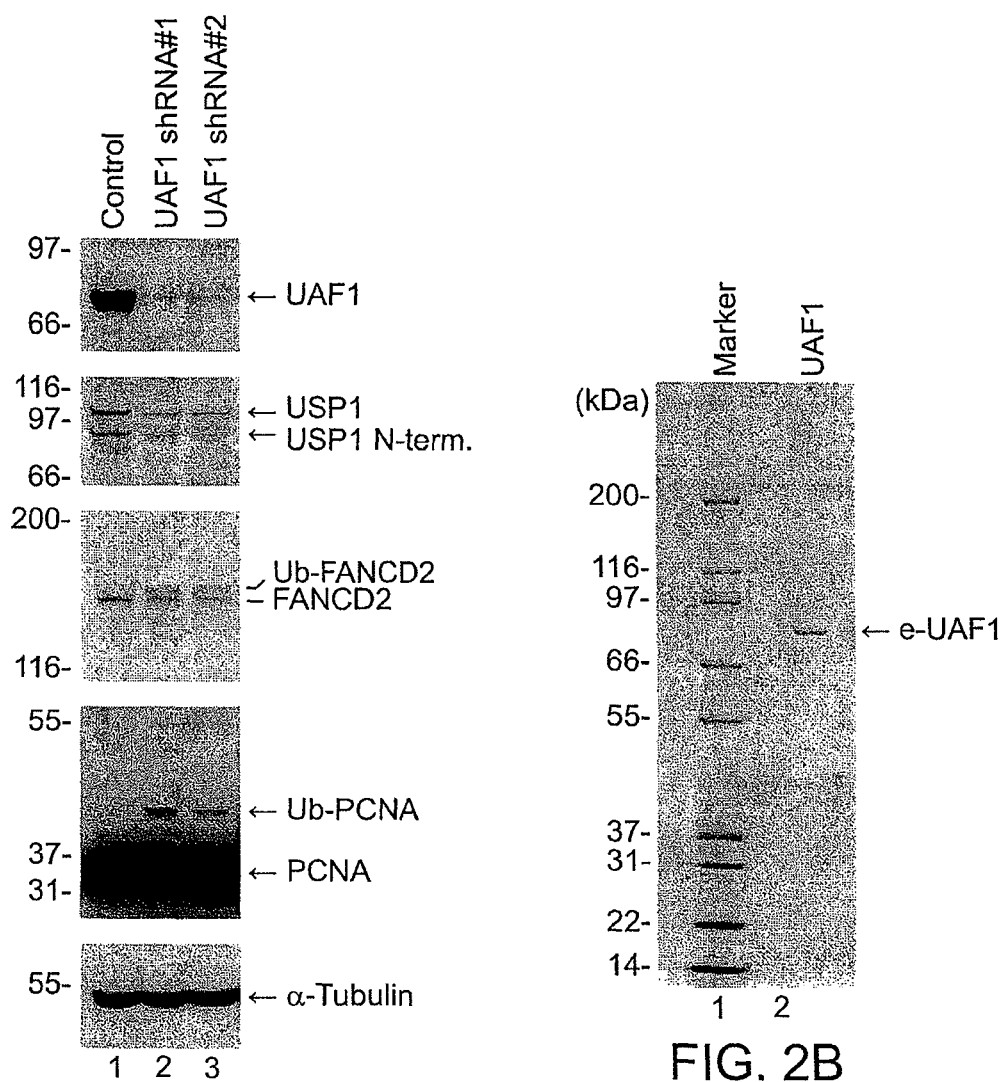
FIG. 2 demonstrates that UAF1 stabilizes USP1 in vivo and in vitro. A) HeLa cells were stably expressing shRNA plasmid constructs targeting UAF1 or a control shRNA plasmid. Protein lysates were prepared and the samples were analyzed by immunoblotting using the indicated antibodies. B) Coomassie blue stain of Flag-HA-tagged UAF1 protein purified from HeLa cells. C) c-Myc-tagged USP1 was synthesized in rabbit reticulocyte either in the absence or presence of UAF1 protein. Translation was inhibited by the addition of cyclohexamide after 1 h, and the reactions were continued for the indicated times. The reactions were analyzed by immunoblotting using the anti-c-Myc (top) or anti-UAF1 antibodies (bottom). D) c-Myc-tagged USP1 was synthesized as in C. Cyclohexamide was added after 1 h and Ubiquitin-Vinyl Sulfone after another 2 h. The reactions were then allowed to continue for 2 h before they were terminated and analyzed by immunoblotting using the same antibodies as in C. E) Both

Since the majority of USP1 is complexed with UAF1 in vivo, the biological significance of the USP1/UAF1 complex was investigated. First, the levels of UAF1 protein were reduced in vivo by transducing HeLa cells with a shRNA expression vector targeting the UAF1 mRNA transcript. Cells depleted of UAF1 protein exhibited a reduced level of USP1 protein (FIG. 2A). We noticed a marked decrease of full length USP1 and an almost complete disappearance of the N-terminal USP1 cleavage product. Decreased USP1 levels were accompanied by an increased level of monoubiquitinated FANCD2 protein, consistent with previous studies (Nijman et al., 2005a). Another USP1 substrate, monoubiquitinated PCNA, was also increased. Thus, in agreement with the purification data of USP1 and UAF1 from HeLa cells (FIG. 1) a decrease of both full length and N-terminal cleavage product of USP1 was observed. These data suggested that the interaction of UAF1 with USP1 is necessary for the stability of USP1 in vivo.

Figure 2C:
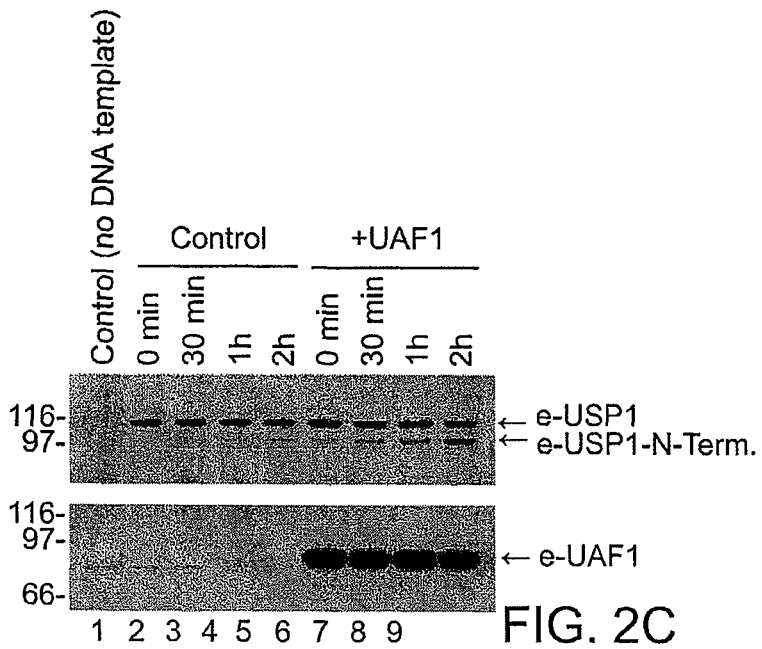

To further test this hypothesis, USP1 stability was assayed in the presence or absence of UAF1 in a rabbit reticulocyte lysate, which is known to be competent for proteasome-mediated protein degradation (Driscoll, J., and Goldberg, A. L. (1990). The proteasome (multicatalytic protease) is a component of the 1500-kDa proteolytic complex which degrades ubiquitin-conjugated proteins. J Biol Chem 265, 4789-4792). c-Myc tagged USP1 was efficiently synthesized by coupled transcription-translation in the lysate (FIG. 2C). UAF1 was purified to homogeneity from HeLa cells as a Flag-HA-epitope tagged fusion protein (FIG. 2B). Upon addition of UAF1 to the reticulocyte lysate, we observed a modest stabilization of full length USP1 (FIG. 2C, lanes 5 and 9) and a greater stabilization of the N-terminal USP1 cleavage product (FIG. 2C, lanes 5 and 9), consistent with the in vivo knockdown experiments (FIG. 2A). However, the possibility that augmented autocleavage also contributes to the accumulation of the USP1 N-terminal cleavage product was not excluded.

Figure 2D:
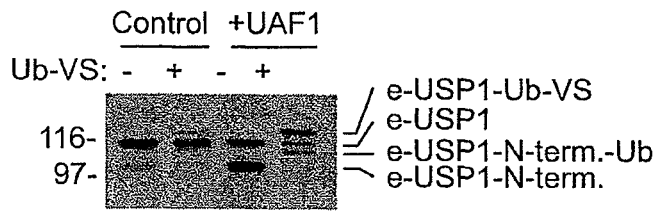
Figure 2E:
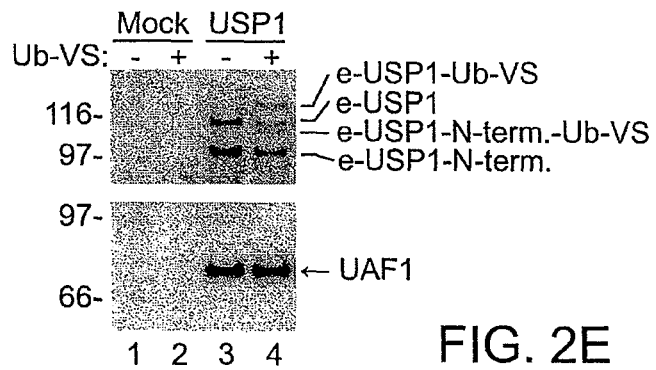

The greater stabilization of the N-terminal USP1 fragment compared to full length USP1 in vivo and in vitro by UAF1, as well as the strong increase of both monoubiquitinated FANCD2 and PCNA in vivo, suggested that the N-terminal cleavage product of USP1 may possess enzymatic deubiquitinating activity. To test this possibility, a modified deubiquitinating enzyme substrate, ubiquitin vinyl sulfone (Ub-VS) was used. Upon catalysis of Ub-VS a covalent bond is formed between the substrate and the active cysteine residue of the enzyme, leading to a mobility shift of 8 kDa of the active enzyme in SDS-PAGE. As hypothesized, there was a shift of both the full length USP1 and the N-terminal cleavage product in the presence of Ub-VS (FIG. 2D, lane 4). Like other cysteine proteases, USP1 contains a Histidine-box in addition to the catalytic Cysteine-box (Fujiwara, T., Saito, A., Suzuki, M., Shinomiya, H., Suzuki, T., Takahashi, E., Tanigami, A., Ichiyama, A., Chung, C. H., Nakamura, Y., and Tanaka, K. (1998). Identification and chromosomal assignment of USP1, a novel gene encoding a human ubiquitin-specific protease. Genomics 54, 155-158). Amino acid residues in both domains, along with an aspartate residue, constitute the catalytic triad. Thus, both Cys- and His-domains are required for enzymatic activity. Intriguingly, a part of the predicted Histidine-box in USP1 is located in the 14 kDa C-terminal cleavage product. It was speculated that the N- and C-termini cleavage products of USP1 are held together by UAF in a ternary complex, which remains catalytically competent. To further reinforce this hypothesis, a similar Ub-VS based enzymatic assay was performed, however now assessing the enzymatic activity of the native USP1 complex purified from HeLa cells. Again, a mobility shift of both full length and the N-terminal cleavage product of USP1 was observed, demonstrating enzymatic activity of both polypeptides (FIG. 2E).

UAF1 Serves as a Co-Factor and Activator of USP1

In the in vitro activity experiment using Ub-VS, it was observed that the percentage of active full length USP1 also increased upon addition of UAF1 (FIG. 2D, lanes 2 and 4). Therefore, it was hypothesized that the activation of the USP1 enzyme might result from a direct binding of UAF1 to newly synthesized USP1 in the in vitro reaction. Indeed, both full length and the N-terminal fragment of USP1 were co-purified by immunoprecipitation of UAF1 from the in vitro reactions (data not shown). Taken together, these data indicate that UAF1 not only interacts with and stabilizes USP1, but also stimulates its enzymatic activity.

Figure 3A:
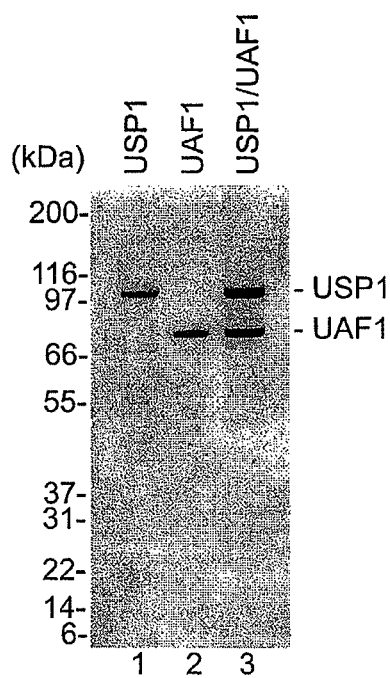
FIG. 3 shows that USP1 is activated by UAF1 in vitro. A) Coomassie blue stain of purified USP1 and UAF1 proteins, expressed either alone of simultaneously as a protein complex in Sf9 cells. B) The in vitro enzymatic activity of USP1, UAF1 or the USP1/UAF1 complex was assayed using Ub-AMC as a substrate. The concentration of each protein was 10 nM. C) Calculation of slopes of the curves in B. The activity of USP1 was arbitrarily set to a value of 1. Relative values for UAF1 and USP1/UAF1 were −0.25 and 36.25, respectively. The slightly negative value for UAF1 is a result of photo bleaching during the experiment. D) UAF1 activates USP1 instantly upon binding in vitro. The enzymatic activity of the USP1 enzyme was monitored as UAF1 was added to the reaction. The concentrations of both USP1 and UAF1 were 2 nM. E) Km and kcat values of the USP1 enzyme and the USP1/UAF1 complex were determined by measuring the substrate conversion at constant enzyme concentration (20 nM for USP1 and 2 nM for the USP1/UAF1 complex) and various substrate concentrations (final concentrations of Ub-AMC of 0.6 µM, 0.75 µM, 1 µM, 1.5 µM and 3 µM for USP1; and 0.42 µM, 0.525 µM, 0.7 µM, 1.05 µM, 2.1 µM and 2.1 µM for the USP1/UAF1 complex). Km and kcat values were calculated by plotting the obtained conversion values in a double-reciprocal Lineweaver-Burk plot. Standard deviation of Km and kcat were calculated from 5-6 independent repeats of the above measurements and are shown in brackets in the table.

In order to dissect the molecular mechanism of UAF1-mediated activation of USP1, the deubiquitinating reaction in vitro was reconstituted using purified components. USP1 or UAF1 proteins were expressed either separately or simultaneously in Sf9 insect cells. A variant of the USP1 protein was also expressed where the amino acids on positions 670-71 were changed from GG to AA, thereby eliminating the autocleavage site in the protein (Huang et al., 2006). Most of the following experiments, which were performed using this non-cleavable version of the USP1 protein, were also performed using the wild type USP1 protein, resulting in similar results (data not shown). As expected, co-expression of USP1 and UAF1 in Sf9 cells led to the formation of a stable heterodimer. The heterodimer and two monomeric proteins were purified to homogeneity (FIG. 3A).

Figure 3B:
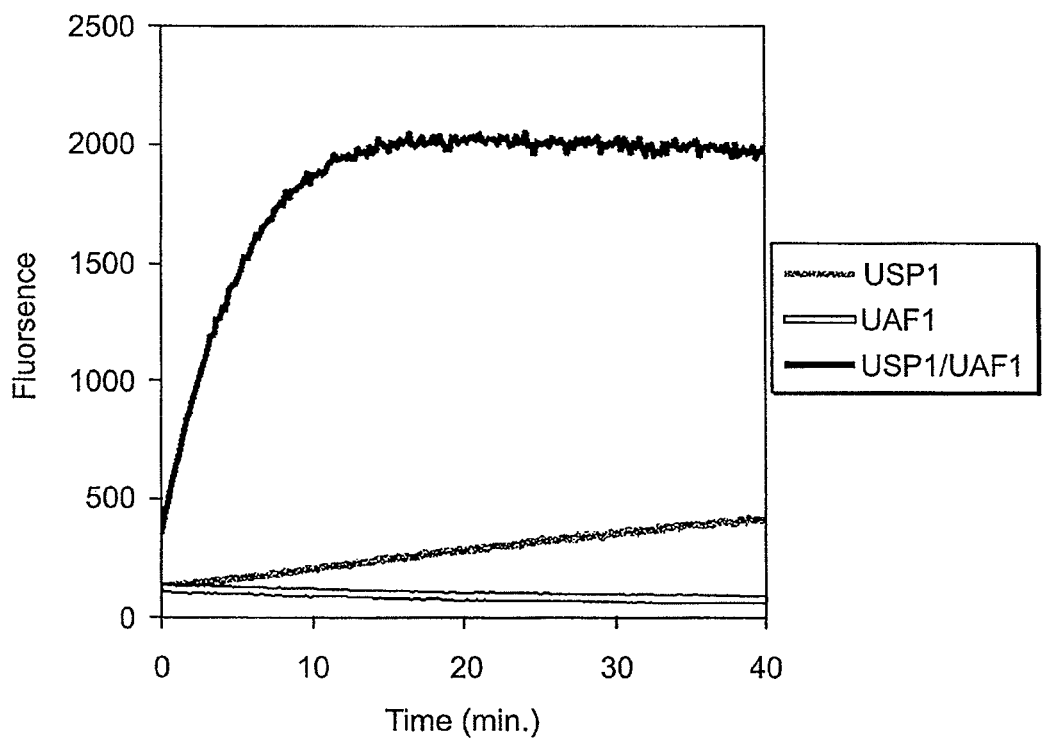
Figure 3C:
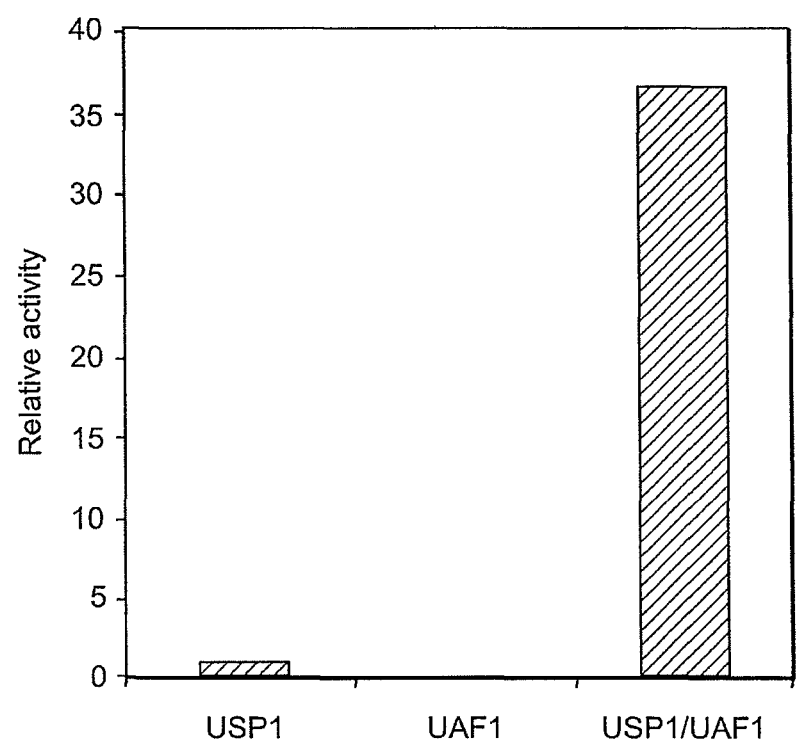

The enzymatic activity of the purified proteins was assayed using fluorogenic Ubiquitin-AMC as a substrate. UAF1 possessed no detectable deubiquitinating activity (FIG. 3B). Interestingly, USP1 displayed a very weak ability to cleave the substrate. The USP1/UAF1 complex, on the other hand, exhibited a strong increase in activity compared to USP1 alone. The activity of the USP1/UAF1 heterodimer was about 30-fold higher than the activity of USP1 alone (FIG. 3C). These data demonstrate that UAF1 stimulates the enzymatic activity of USP1 through the formation of an active protein heterodimer.

Figure 3D:
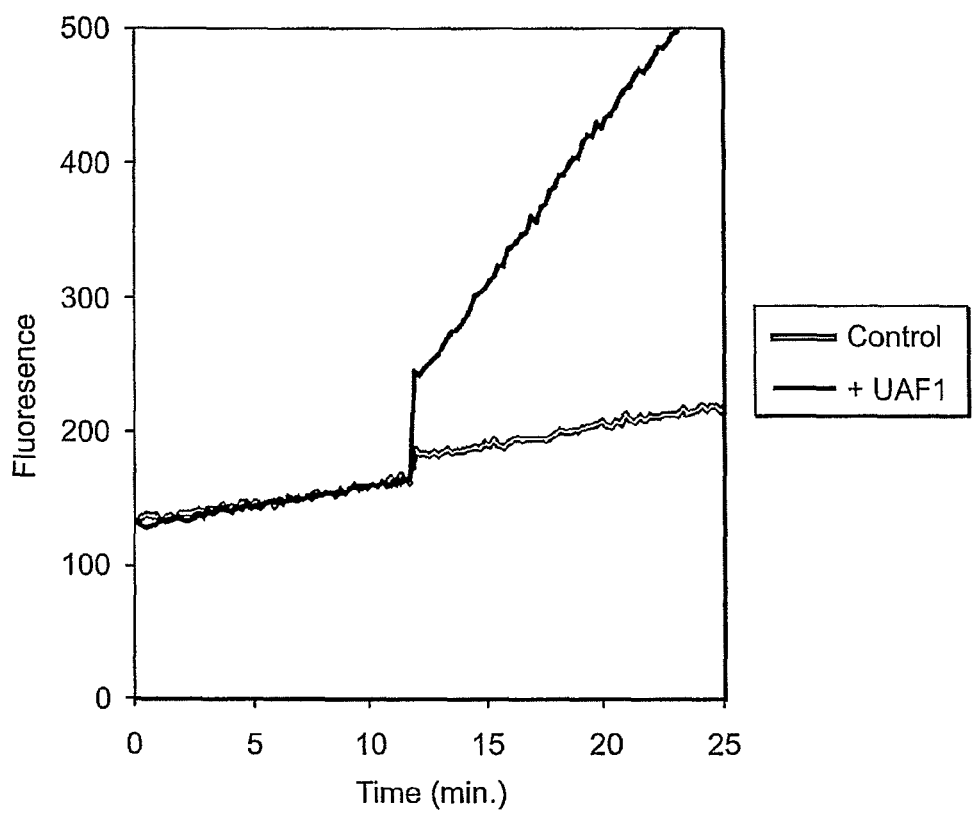

The above experiments were performed using a preformed USP1/UAF1 complex. To gain further insight into the dynamics of USP1/UAF1 complex formation and USP1 activation, the kinetics of UAF1 binding and activation of USP1 were investigated. An in vitro enzymatic reaction of USP1 was set up using Ubiquitin-AMC as a substrate. Ten minutes into the reaction, during the stable and low substrate-turnover, either buffer or purified UAF1 protein was added in an equimolar amount to USP1. Addition of UAF1 resulted in an instantaneous and robust increase of substrate turnover (FIG. 3D). The slope of the curve changed immediately to its new linear slope after the addition of UAF1, demonstrating that UAF1 has a very high affinity for the USP1 enzyme. Given the affinity between the two proteins, it was predicted that as USP1 is synthesized in the cell, it rapidly forms a complex with UAF1. If UAF1 is not available, the protein is destabilized and degraded. Such a scenario reveals UAF1 as the regulatory factor of USP1.

Figure 3E:
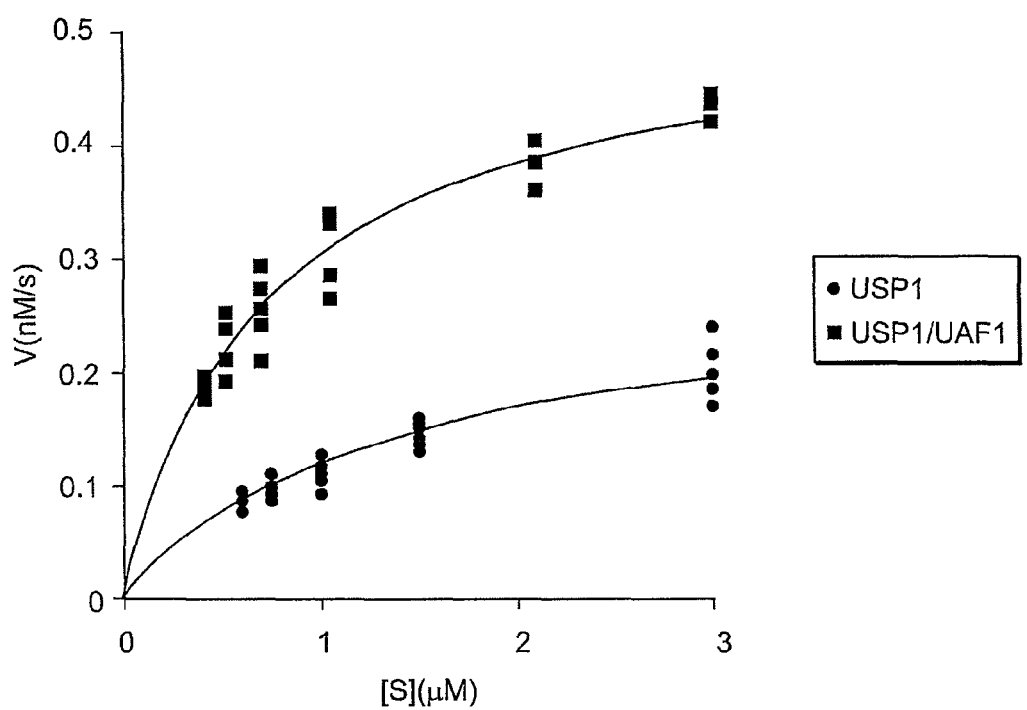

In order to better understand the enzymatic consequences of the complex-formation between UAF1 and USP1, the kinetic parameters of the USP1 enzyme alone and the UAF1/USP1 complex were determined. By assaying the substrate conversion at increasing substrate concentrations (FIG. 3E) it was determined that the affinity of USP1 for its Ubiquitin substrate is only modestly influenced by UAF1, decreasing the Km from 1.4 µM to 0.7 µM (FIG. 3F). In contrast, the catalytic turnover was robustly increased by UAF1, augmenting the kcat value 18-fold. As a result, the kcat/Km is 35-fold higher for the UAF1/USP1 complex compared to USP1 alone. Thus, UAF1 does not affect the recruitment of USP1 to its substrate but rather stimulates its ability to deubiquitinate the substrate. This mechanism of activation contrasts with that of another deubiquitinating enzyme, Uch37, which is involved in proteasome-mediated protein degradation. Uch37 is activated by the Adrm1 protein. However, the binding of Adrm1 to Uch37 did not increase the kcat value, but rather led to 6-fold decrease in Km, seemingly promoting recruitment of the enzyme to the substrate (Qiu, X. B., Ouyang, S. Y., Li, C. J., Miao, S., Wang, L., and Goldberg, A. L. (2006). hRpn13/ADRM1/GP110 is a novel proteasome subunit that binds the deubiquitinating enzyme, UCH37. Embo J 25, 5742-5753; Yao, T., Song, L., Xu, W., DeMartino, G. N., Florens, L., Swanson, S. K., Washburn, M. P., Conaway, R. C., Conaway, J. W., and Cohen, R. E. (2006). Proteasome recruitment and activation of the Uch37 deubiquitinating enzyme by Adrm1. Nat Cell Biol 8, 994-1002).

The WD40 Repeats of UAF1 are Required for the Interaction with USP1

Figure 4A:
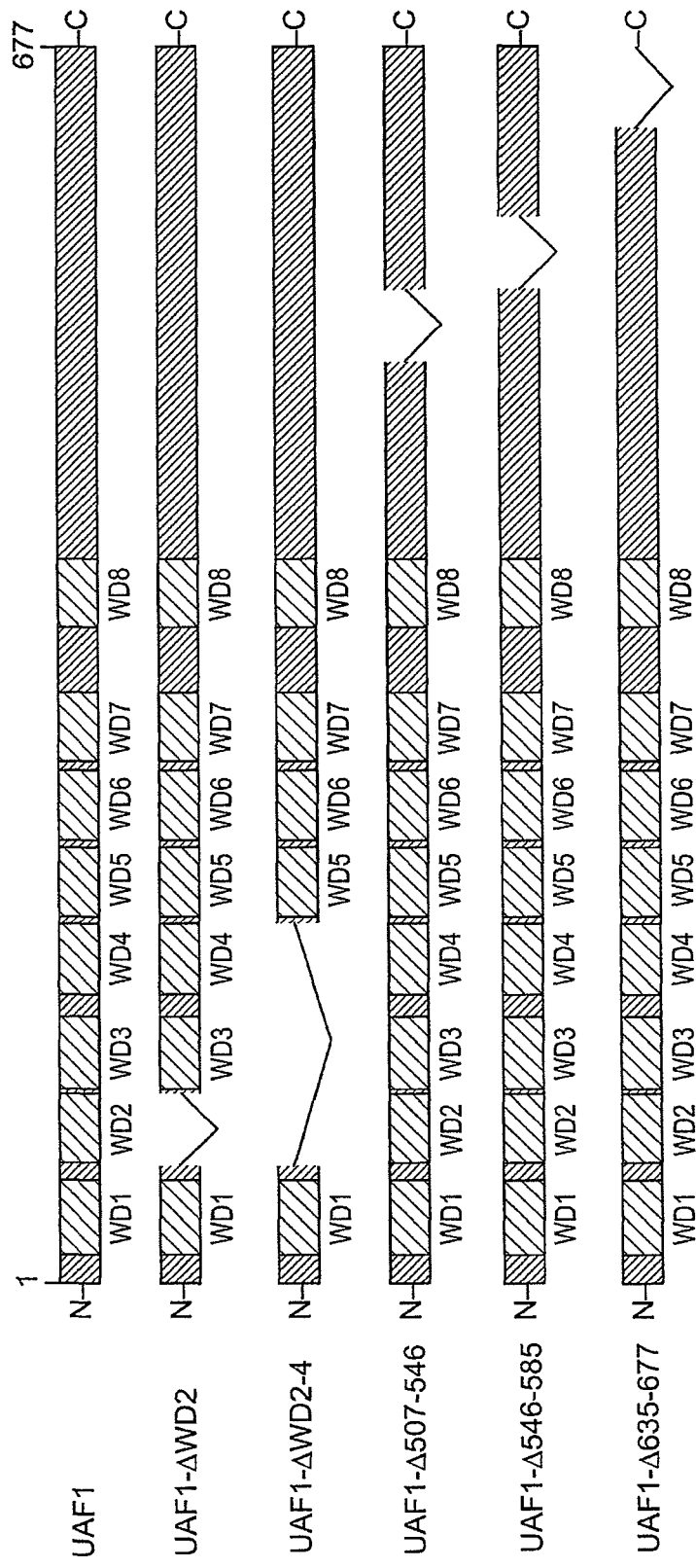
FIG. 4 shows that the WD40 repeats of UAF1 are essential for binding to and activation of USP1. A) Scheme of wild type UAF1 and deletion mutants thereof. B) Flag-tagged deletion mutants of UAF1 were transiently expressed in 293T cells. The Flag-tagged proteins were immunoprecipitated from cell lysates using anti-Flag antibodies. The immunoprecipitates were analyzed using the indicated antibodies. C) A mutant protein of UAF1 where the second WD40 repeat has been deleted (UAF1-ΔWD2) fails to activate USP1 enzymatic activity in vitro. Strep-tagged UAF1-ΔWD2 was expressed and purified from Sf9 insect cells. The enzymatic activity of the USP1 enzyme was monitored as UAF1 wild type or mutant proteins was added to the reaction. The concentrations of all proteins were 10 nM.
Figure 4B:
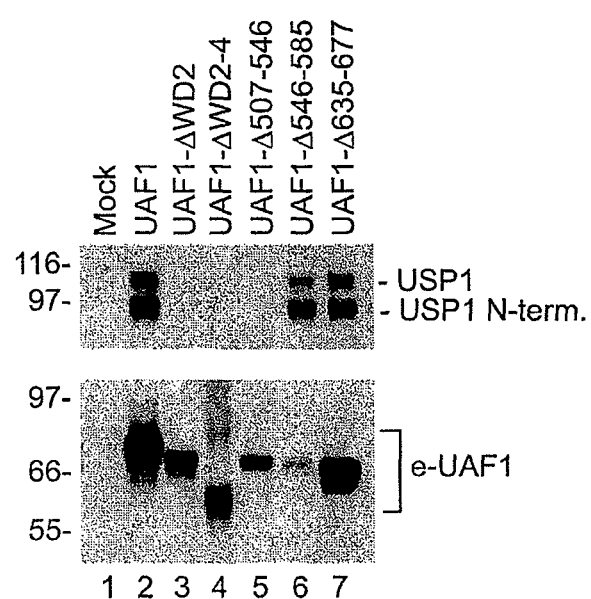

To better understand the nature of the UAF1 mediated activation of USP1, which domains of the UAF1 protein are responsible for the protein-protein interaction was examined. A series of deletion proteins of UAF1 were generated, where one or more of the WD40 repeats have been deleted (FIG. 4A). The proteins were expressed in 293T cells as Flag-tagged fusion proteins and their abilities to interact with endogenous USP1 was assayed by immunoblot analysis of anti-Flag immunoprecipitates. Deletion of WD40 repeats 2-4 completely abrogated the interaction with USP1 (FIG. 4B). Deletion of only WD40 repeat 2 was also sufficient to prevent any detectable interaction with USP1. Deletion of WD40 repeat 8 resulted in a protein, which could not be expressed in 293T cells, suggesting that the resulting protein is misfolded (data not shown). A deletion close to the eighth WD40 repeat also interfered with the protein's ability to interact with USP1, suggesting that border-regions outside the WD40 repeats also may be required for correct folding of the predicted propeller structure composed by the WD40 repeats. Only deletions in the proximal C-terminal part of the protein did not interfere with the USP1-interaction (FIG. 4B). It was concluded that the large region containing at least all 8 predicted WD40 repeats are required for correct folding of UAF1 and for its ability to form a complex with USP1.

Figure 4C:
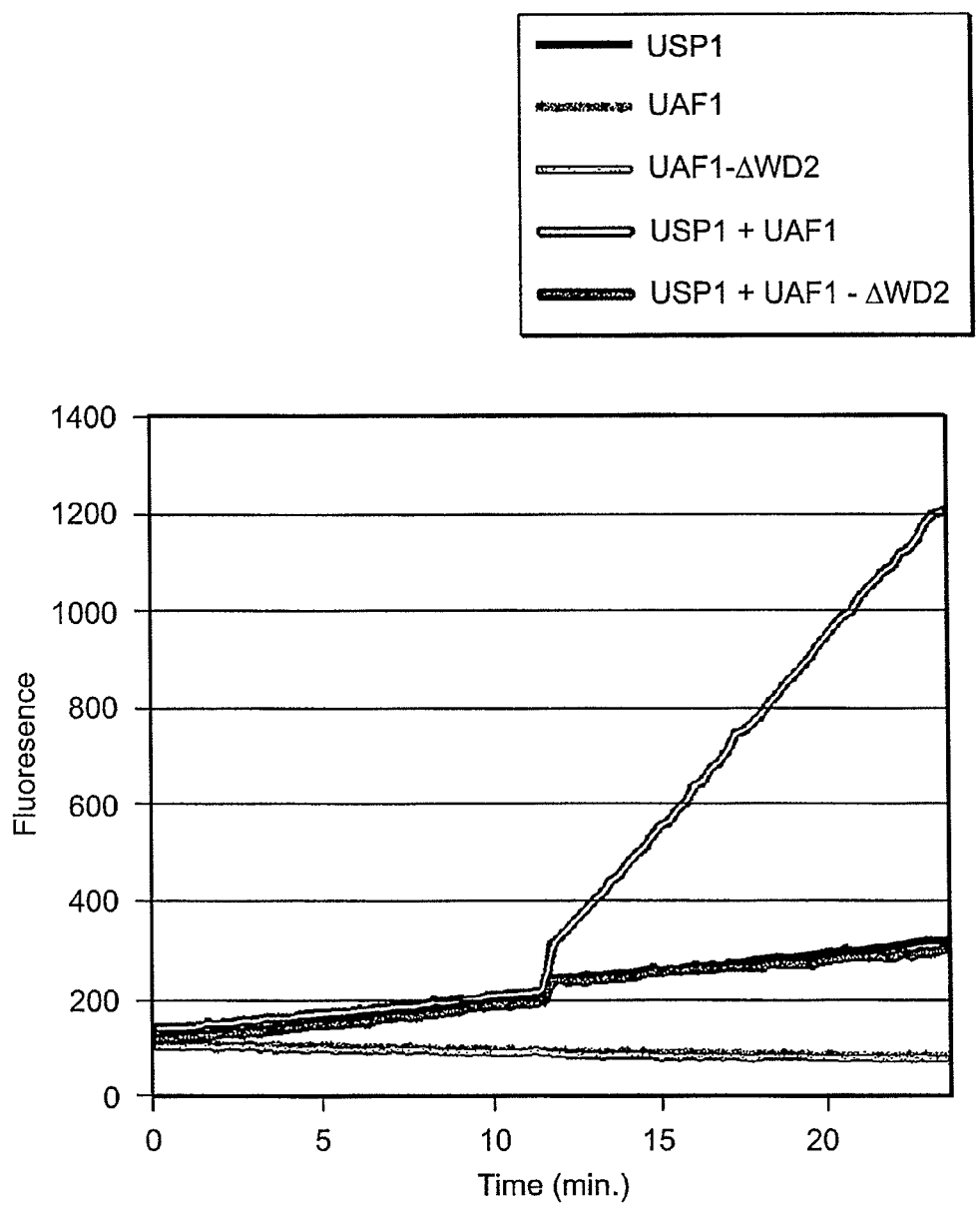

The importance of the WD40 repeats in the UAF1 protein for its ability to form a protein complex with USP1 in vivo suggested a direct correlation between the observed binding and the protein's ability to activate USP1. In order to test this, we expressed and purified one of the deletions mutants of UAF1, UAF1-ΔWD2, in Sf9 insect cells, and tested whether it could activate the USP1 enzyme in vitro. While wild type UAF1 was able to stimulate the enzymatic activity of USP1, the mutant UAF1 protein had no stimulating potential (FIG. 4C). Taken together, the data show that the WD40 repeats of UAF1 are essential for the protein's ability to form a complex with the USP1 deubiquitinating enzyme and to stimulate its enzymatic activity.

The UAF1/USP1 Complex Deubiquitinates Ub-FANCD2 in vitro

Figure 5A:
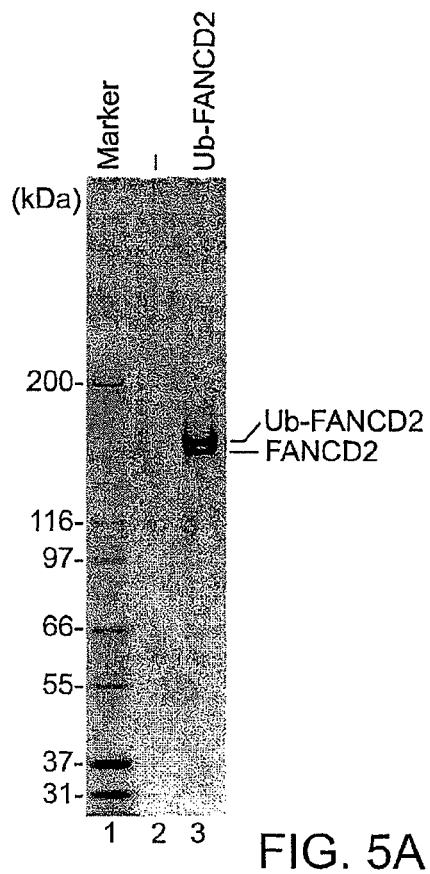
FIG. 5 shows that the USP1/UAF1 complex deubiquitinates monoubiquitinated FANCD2 protein in vitro. A) Silver stain of monoubiquitinated FANCD2 protein purified from HeLa cells. B) Recombinant USP1/UAF1 complex purified from Sf9 cells but not the USP1 protein alone can deubiquitinate Ub-FANCD2 in vitro. C) In vitro deubiquitination of Ub-FANCD2 by the USP1/UAF1 complex purified from Sf9 cells. The deubiquitination reactions were carried out for the times indicated. D) The native USP1 complex purified from HeLa cells can deubiquitinate Ub-FANCD2 protein in vitro.
Figure 5B:
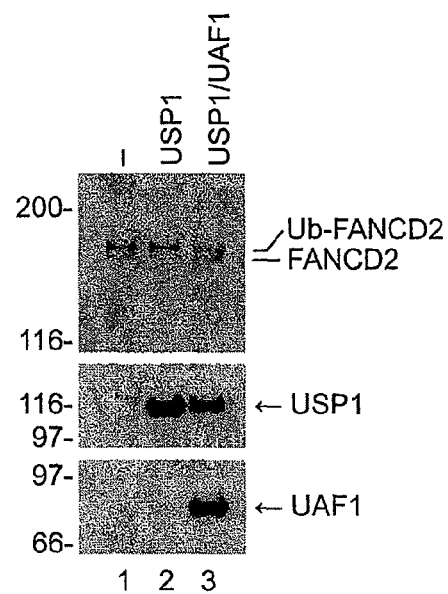
Figure 5C:
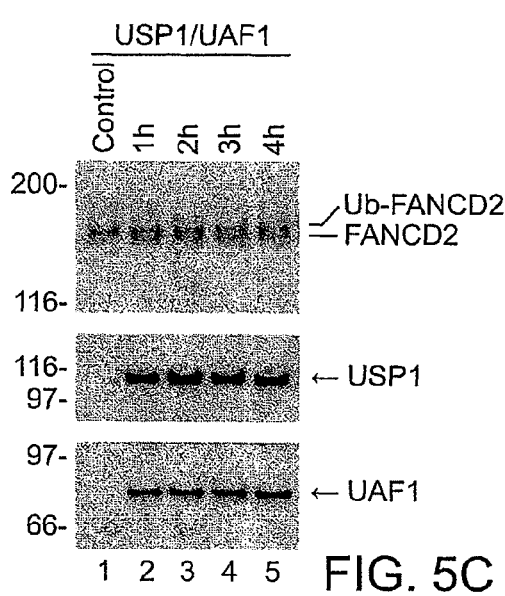

Deubiquitination of the Ub-FANCD2 protein has not been previously reconstituted in vitro. The finding that USP1 is activated by UAF1 prompted the testing of whether the UAF1/USP1 complex is capable of deubiquitinating this physiologic substrate. To generate the substrate, a Flag-HA-tagged FANCD2 protein was expressed in HeLa cells. After treating the cells with hydroxyurea for 24 h to activate monoubiquitination, the protein was purified to homogeneity (FIG. 5A). The purified Ub-FANCD2 protein was subjected to an in vitro deubiquitinating reaction, using either USP1 enzyme alone or the UAF1/USP1 complex, both purified from Sf9 cells. USP1 protein alone was unable to deubiquitinate Ub-FANCD2 (FIG. 5B, lane 2). In contrast, the UAF1/USP1 complex readily deubiquitinated the substrate (FIG. 5B, lane 3). In these in vitro reactions about half of the substrate was deubiquitinated (FIG. 5B, lane 3). Monitoring of the Ub-FANCD2 deubiquitination over time, indicated that the reaction reached equilibrium relatively fast (FIG. 3C). It is believed that the origin of the substrate, being ubiquitinated in vivo, allows for a non-homogenous substrate population, perhaps with variation in folding or posttranslational modifications. As a result, a fraction of the Ub-FANCD2 protein may not be a suitable substrate for deubiquitination.

Figure 5D:
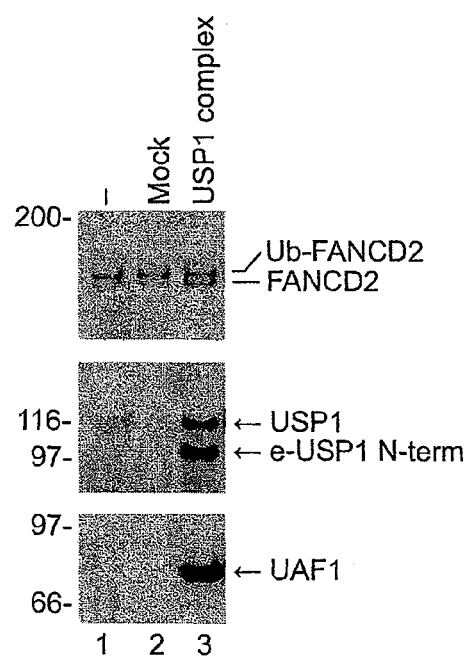

This is the first demonstration of in vitro deubiquitination of monoubiquitinated FANCD2 protein, and thus the first direct evidence that USP1 directly deubiquitinates this substrate. To further reinforce this finding, testing was performed to determine whether the native USP1 complex purified from HeLa cells was also able to deubiquitinate the Ub-FANCD2 substrate. Indeed, the USP1 complex could support this reaction (FIG. 5D, lane 3) whereas a mock purification contained no deubiquitinating activity (FIG. 5D, lane 2).

Taken together, the data demonstrate a role of UAF1 as an essential activator of the USP1 enzymatic activity towards the monoubiquitinated FANCD2 protein.

Transcription of the USP1 Gene is Suppressed in Response to UV Irradiation

Figure 6A:
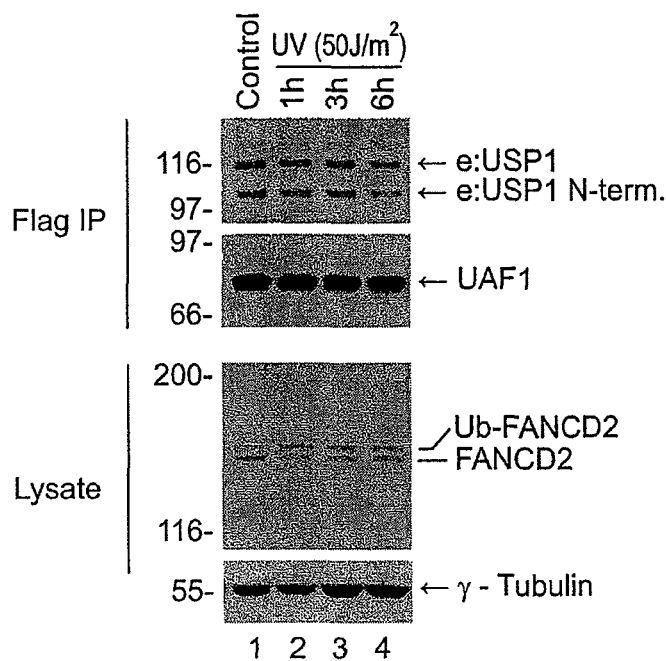
FIG. 6 shows that transcription of the USP1 gene is rapidly suppressed in response to genotoxic stress. A) HeLa cells expressing exogenous Flag-HA-USP1 were irradiated with 50 J/m$^2$ and samples were taken at the indicated times. Flag-HA-USP1 was immunoprecipitated using anti-Flag antibodies and the immunoprecipitates were analyzed by immunoblotting using the indicated antibodies with the exception of Flag-HA-USP1, which was detected using the mouse monoclonal 12CA5 antibody. B) HeLa cells were UV irradiated with 50 J/m$^2$ (UVC) and samples were taken at the indicated times. Protein samples were analyzed by immunoblotting using the indicated antibodies. C) 293T cells were UV irradiated with 100 J/m2 (UVC) and samples were taken at the indicated times. Total RNA was prepared an analyzed by Northern blot analysis using the indicated probes. D) Quantification of the USP1 and total RNA intensities from C. E) 293T cells were treated with 5 µg/ml Actinomycin D and samples were taken at the indicated times. Protein samples were analyzed by immunoblotting using the indicated antibodies.

The level of monoubiquitinated FANCD2 protein increases in response to various types of DNA damage in mammalian cells. This increase of Ub-FANCD2 results, at least in part, from a corresponding decrease in USP1 levels (Nijman et al., 2005). The finding that the USP1 enzyme is nearly inactive, unless it is a part of the UAF1/USP1 complex, prompted an investigation as to whether the complex dissociates after DNA damage. Dissociation would, in principle, lead to a loss of USP1 deubiquitinating activity. In order to test this, Flag-HA-tagged USP1 from HeLa cells was immunoprecipitated at various times after UV irradiation, and the inimunoprecipitate was analyzed for UAF1 protein levels by immunoblotting. The UAF1/USP1 complex was relatively stable after UV irradiation, and the levels of UAF1 were directly proportional to the levels of USP1 (FIG. 6A). Thus, the UAF1/USP1 complex does not dissociate in response to UV irradiation.

Figure 6B:
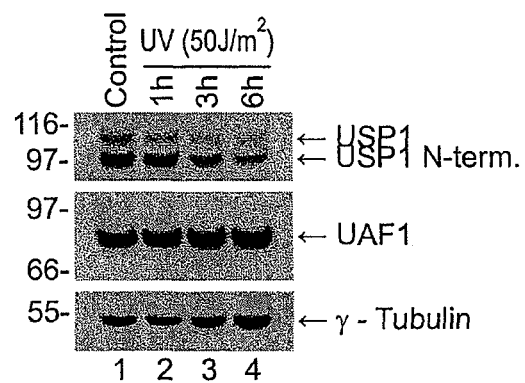
Figure 6D:
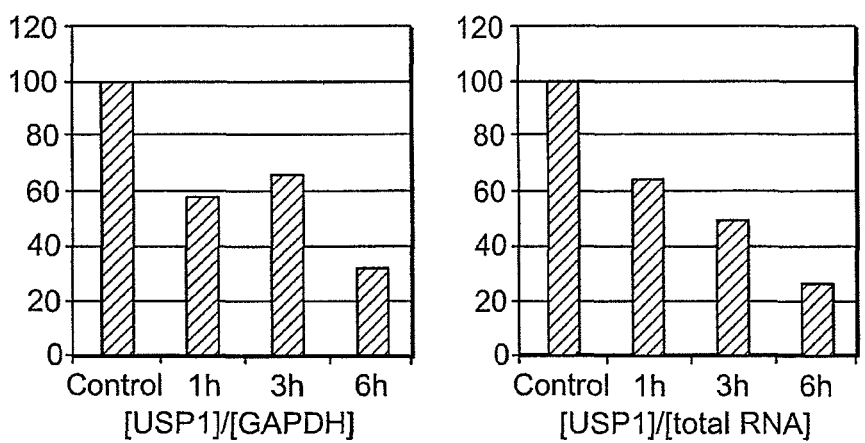
Figure 6C:
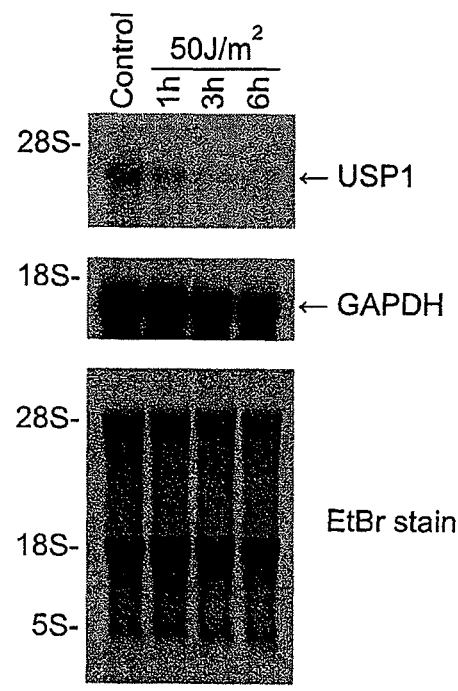
Figure 6E:
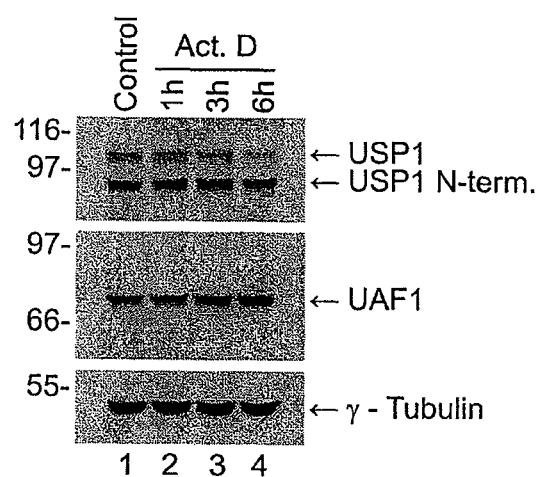

In the above experiments, it was observed that the exogenously expressed USP1 protein (FIG. 6A) was more stable after UV irradiation than endogenous USP1 protein (FIG. 6B). UAF1 protein levels were not affected by UV irradiation (FIG. 6A and FIG. 6B). It was speculated that one regulatory event that may reduce USP1 activity after DNA damage may be transcriptional down-regulation of the USP1 gene. To test this hypothesis, USP1 mRNA levels were measured in 293T cells after UV irradiation. A rapid decrease of the USP1 mRNA (FIG. 6C) was observed, with kinetics reflecting the decrease of USP1 protein (FIG. 6B). The abundance of USP1 transcript was nearly reduced by 50% only one hour after the UV irradiation (FIG. 6D). These data suggest that transcription of the USP1 gene is shut off in response to UV irradiation, allowing the cells to accumulate sufficient monoubiquitinated FANCD2 protein required for DNA repair. To test whether active mRNA degradation also play a role in addition to transcriptional regulation, transcription was inhibited by Actinomycin D, an effective inhibitor of RNA polymerase II, cells were irradiated with UV, or both treatments were combined. The USP1 mRNA decreased with similar kinetics in all three cases, indicating that shut down of transcription is the major mechanism underlying the decrease of USP1 mRNA (data not shown). The USP1 protein levels were also analyzed after blocking transcription by Actinomycin D. Again, blocking transcription resulted in a decrease of USP1 protein levels over time, while the level of UAF1 protein remained unchanged (FIG. 6E). Importantly, the level of full length USP1 decreased with kinetics similar to those in cells treated with UV irradiation (FIG. 6B).

General Mechanism of Deubiquitinating Enzyme Activation

It was recently reported that the Uch37 deubiquitinating enzyme, which is involved in proteasome-mediated protein degradation, is activated by the WD40 domain containing Adrm1 protein (Qiu et al., 2006; Yao et al., 2006). The mechanism of activation of Uch37 by Adrm1 is conceptually different than the mechanism of USP1 activation, in that the catalytic activity of Uch37 is unaltered by Adrm1, which instead serves to recruit the enzyme to the proteasome. USP1, on the contrary, is activated by UAF1 not through recruitment, but instead by a pronounced increase in catalytic turnover. Mutagenesis analysis of UAF1 indicates that the predicted propeller structure comprised by the WD40 repeats of UAF1 is responsible for the strong interaction with USP1. It is speculated that the binding of UAF1 to USP1 induces a conformational change of the enzyme resulting in a robust increase in enzymatic activity.

It is likely that other human deubiquitinating enzymes also are regulated by specific activating WD40 repeat proteins. Indeed, a systematic analysis of the existing literature on global protein-protein interaction studies from *Saccharomyces cerevisiae*, revealed that 11 out of 19 yeast deubiquitinating enzymes were found in protein complexes containing WD40 repeat proteins (Gavin, A. C., Aloy, P., Grandi, P., Krause, R., Boesche, M., Marzioch, M., Rau, C., Jensen, L. J., Bastuck, S., Dumpelfeld, B., et al. (2006). Proteome survey reveals modularity of the yeast cell machinery. Nature 440, 631-636; Gavin, A. C., Bosche, M., Krause, R., Grandi, P., Marzioch, M., Bauer, A., Schultz, J., Rick, J. M., Michon, A. M., Cruciat, C. M., et al. (2002). Functional organization of the yeast proteome by systematic analysis of protein complexes. Nature 415, 141-147; Ho, Y., Gruhler, A., Heilbut, A., Bader, G. D., Moore, L., Adams, S. L., Millar, A., Taylor, P., Bennett, K., Boutilier, K., et al. (2002). Systematic identification of protein complexes in *Saccharomyces cerevisiae* by mass spectrometry. Nature 415, 180-183; Ingvarsdottir, K., Krogan, N. J., Emre, N. C., Wyce, A., Thompson, N. J., Emili, A., Hughes, T. R., Greenblatt, J. F., and Berger, S. L. (2005). H2B ubiquitin protease Ubp8 and Sgf11 constitute a discrete functional module within the Saccharomyces cerevisiae SAGA complex. Mol Cell Biol 25, 1162-1172; Krogan, N. J., Cagney, G., Yu, H., Zhong, G., Guo, X., Ignatchenko, A., Li, J., Pu, S., Datta, N., Tikuisis, A. P., et al. (2006). Global landscape of protein complexes in the yeast *Saccharomyces cerevisiae*. Nature 440, 637-643; Lee, K. K., Florens, L., Swanson, S. K., Washburn, M. P., and Workman, J. L. (2005). The deubiquitylation activity of Ubp8 is dependent upon Sgf11 and its association with the SAGA complex. Mol Cell Biol 25, 1173-1182; Rumpf, S., and Jentsch, S. (2006). Functional division of substrate processing cofactors of the ubiquitin-selective Cdc48 chaperone. Mol Cell 21, 261-269). The exact implication on the enzymatic activity of these enzymes by the interacting WD40 repeat proteins still has to be determined. It will be interesting to determine whether the approximately 90 remaining human deubiquitinating enzymes are also regulated by WD40 repeat proteins.

Example 2

Production of a Polyclonal Antibody to UAF1

A polyclonal rabbit antibody was raised against a fragment of the UAF1 protein consisting of amino acids 400-677. A 6× His-UAF1(400-677) fusion protein was expressed in *E. coli* and purified over an NTA column. The purified protein was injected subcutaneously into a rabbit with Freund's complete adjuvant in the first injection and Freund's incomplete adjuvant for the following boost-injections.

Example 3

Effect of UAF1 siRNA Knockdown on Monoubiquitination of PCNA and FANCD2

Two siRNAs were identified that inhibit the expression of UAF1 in transiently transfected HeLa cells. The siRNAs had the antisense sequences CCGGTCGAGACTCTATCATAA (SEQ ID NO:8), and CACAAGCAAGATCCATATATA (SEQ ID NO:9). Immunoblots using the UAF1 antibody of Example 2 showed no UAF1 protein after siRNA knockdown. (Not shown).

As demonstrated in the experiment depicted in FIGS. 7A and 7B, UAF1 knockdown resulted in decreased expression of USP1 protein. This indicated that UAF1 acts as a stabilizing dimeric partner of endogenous USP1. Experiments were performed using HEK293 cells. The cells were treated with 20 nM UAF1 siRNA for 72 hours. Control experiments treated the cells with 20 nM siLacZ siRNA. The proteasome inhibitor MG132 was added at 10 µM for 2 hours during UV treatment to trap the autocleavage product of USP1 so as to determine the autocatalytic activity of USP1 in the presence and absence of UAF1. The LacZ siRNA and antibodies are described in Huang, et al., Nature Cell Biol. 8(4):339-47 ((2006).

Example 4

Co-Expression of UAF1 and USP1

UAF1 knockdown resulted in cellular resistance to IR and MMC. Coexpression of UAF1 and USP1 enhanced the autocleavage of USP1 thus activating its protease activity. HEK293 cells were transfected using either pcDNA3 (empty vector), pcDNA-Myc-USP1 wt, or pcDNA4-his-XpressTAG-UAF1 constructs. The UV dose was 60 J/m$^2$ for 3 hours, and the indicated cells were exposed to 10 µM MG132 for an additional 3 hours.

Example 5

Stable Knockdown of UAF1 Using shRNA

HeLa and 293T cells were transfected with a vector expressing shRNA directed to UAF1 (pSuper-UAF1.7). The pSuper (Clonetech) retroviral vector was used to clone the UAF1 target sequence. The resulting plasmid, pSuper-UAF1.7 was transfected into a retroviral packaging cell line. The culture supernatant containing the retroviruses was used to transduce the HeLa and 293T cells. Cells with the plasmid integrated were selected by puromycin selection. An immunoblot was performed using the UAF1 antibody of Example 2. An antibody to a housekeeping gene, alpha tubulin, showed no change in expression. However, the results demonstrated stable knockdown of UAF1 expression in both cell types.

Figure 9:
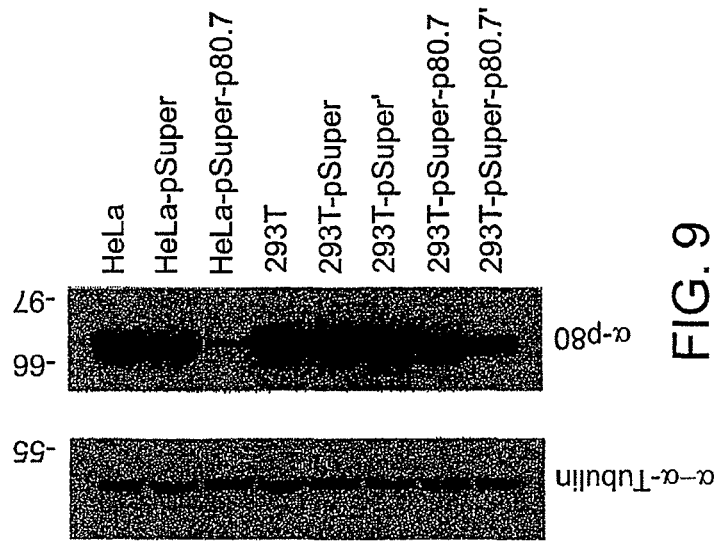
FIG. 9 shows a Western blot that demonstrates the effect on UAF1 expression (anti-UAF1 antibody, upper panel) of transfection of HeLa and 293T cell lines with shRNA directed to UAF1. A tubulin control is shown (anti-alpha tubulin antibody, lower panel).
Figure 8:
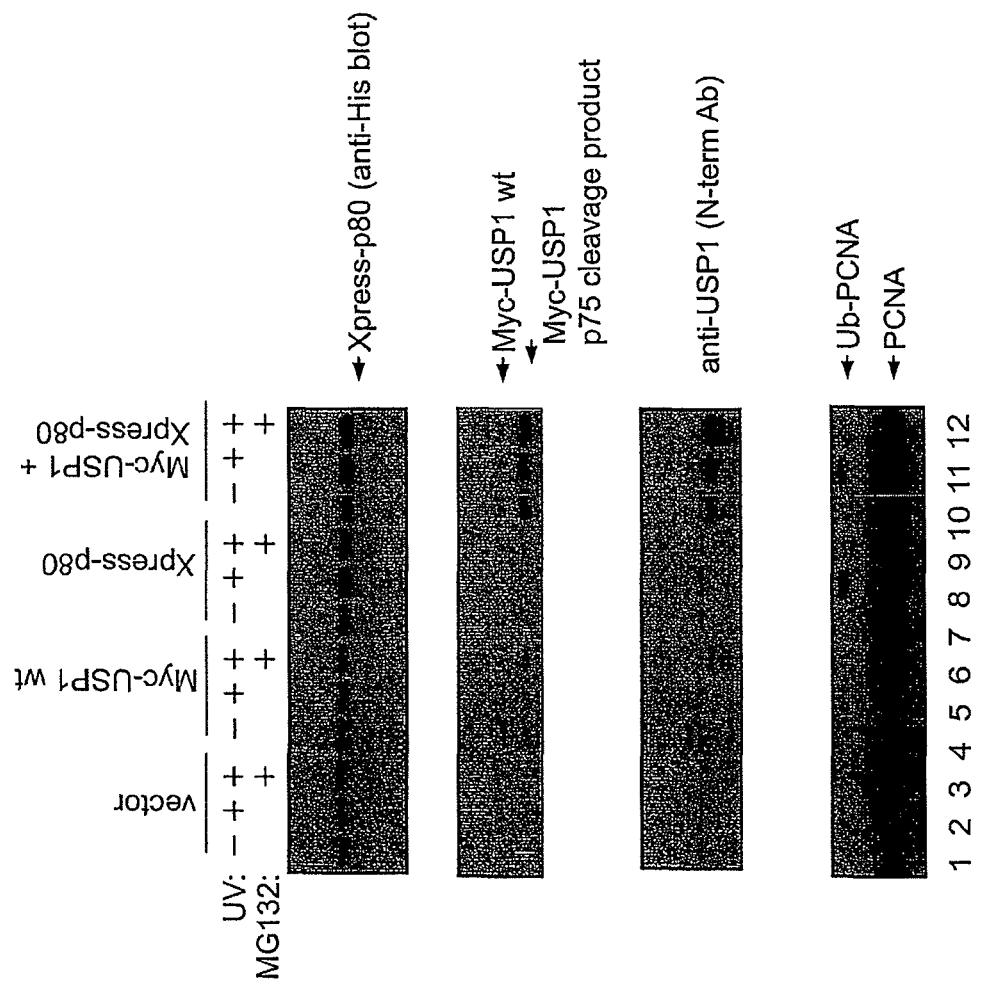
FIG. 8 shows the effects of co-expression of UAF1 and USP1. A Western blot is presented, showing UAF1 expression (top panel), USP1 expression (second panel from top), USP1 autocleavage product (third panel from top), and PCNA ubiquitination state (bottom panel).

(See FIG. 9). Vector controls (HeLa-pSuper and 293T-pSuper) showed no change in UAF1 expression.

Example 6

Effect on Cell Survival to Mitomycin C of shRNA Knockdown of UAF1 in HeLa Cells

Figure 10:
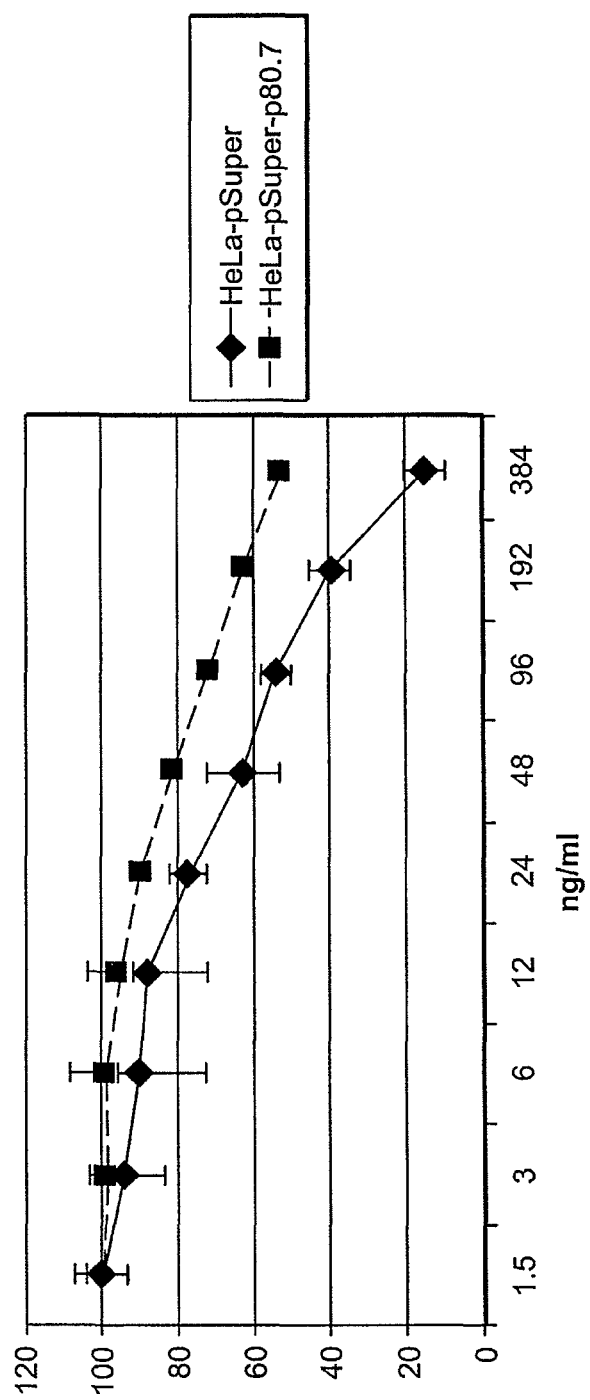
FIG. 10 depicts the percent survival of HeLa cells exposed to the indicated concentrations mitomycin C (MMC) with (HeLa-pSuper-UAF1.7) and without (HeLa-pSuper, vector control) transfection with shRNA directed to UAF1.

HeLa cells transfected with a vector producing shRNA directed to UAF1 (see Example 5) were exposed to increasing concentrations of mitomycin C (MMC). Cells were plated in 96-well cell culture plates. MMC was added after 24 h, and treatment continued for 3 days. Survival was assessed by the CellTiter Glo assay (Promega). Control cells (HeLa-pSuper) were transfected with vector alone without shRNA. The results are shown in FIG. 10. The UAF1 shRNA significantly enhanced the survivability of the cells after exposure to MMC.

Example 7

Effect on Cell Survival to Cisplatin of siRNA Knockdown of USP1

Figure 11:
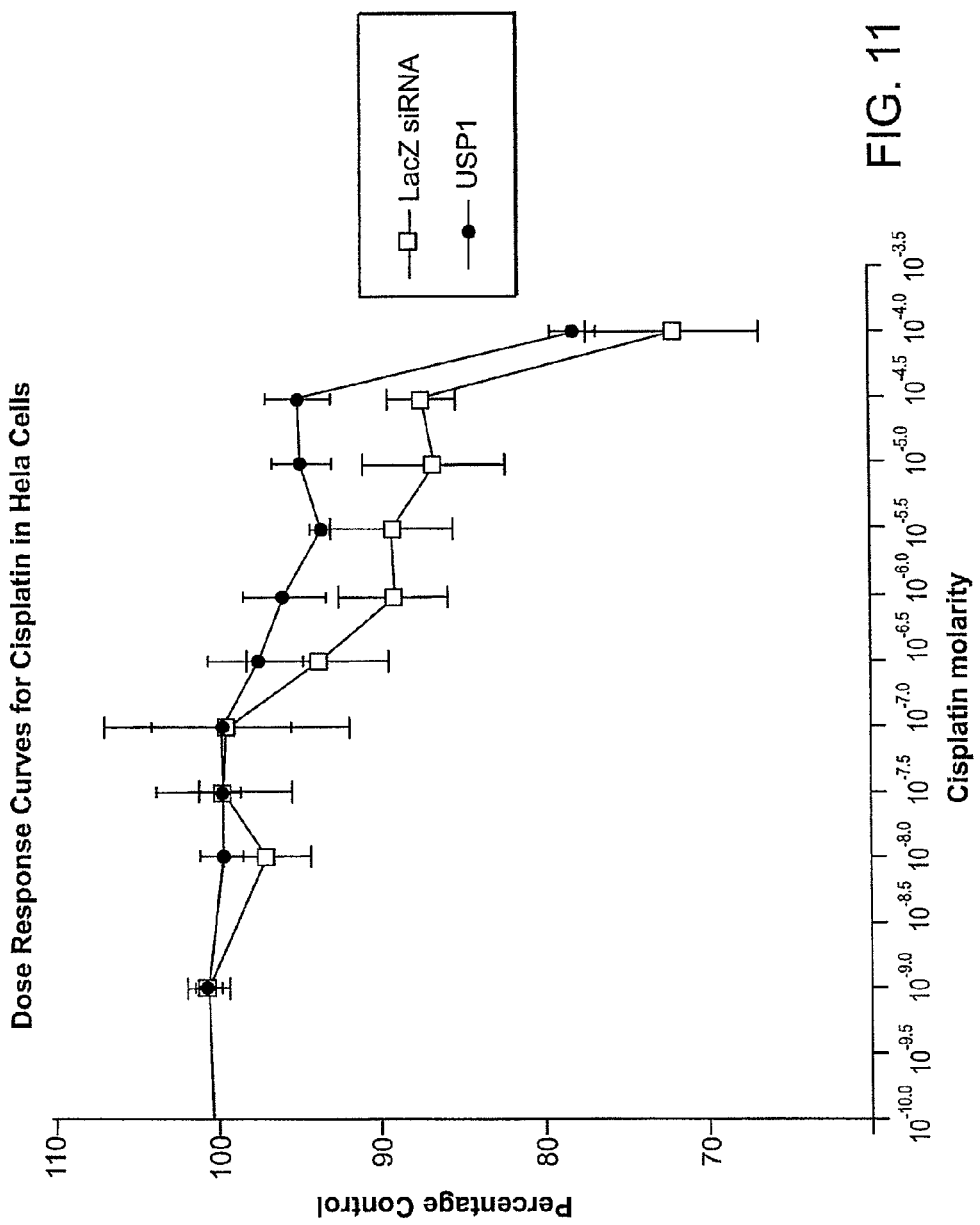
FIG. 11 shows the percent survival of HeLa cells treated with siRNA directed to USP1 (or a LacZ siRNA control) as a function of the indicated concentrations of cisplatin.

HeLa cells were treated with 20 nM siRNA directed to USP1 for 72 hours. LacZ siRNA was used as a control. As shown in FIG. 11, knockdown of USP1 improved survivability to cisplatin. siRNA treatment against USP1 mRNA resulted in greater than 90% knockdown.

Example 8

Effect on Cell Survival to Gamma Radiation of siRNA Knockdown of UAF1

Figure 12:
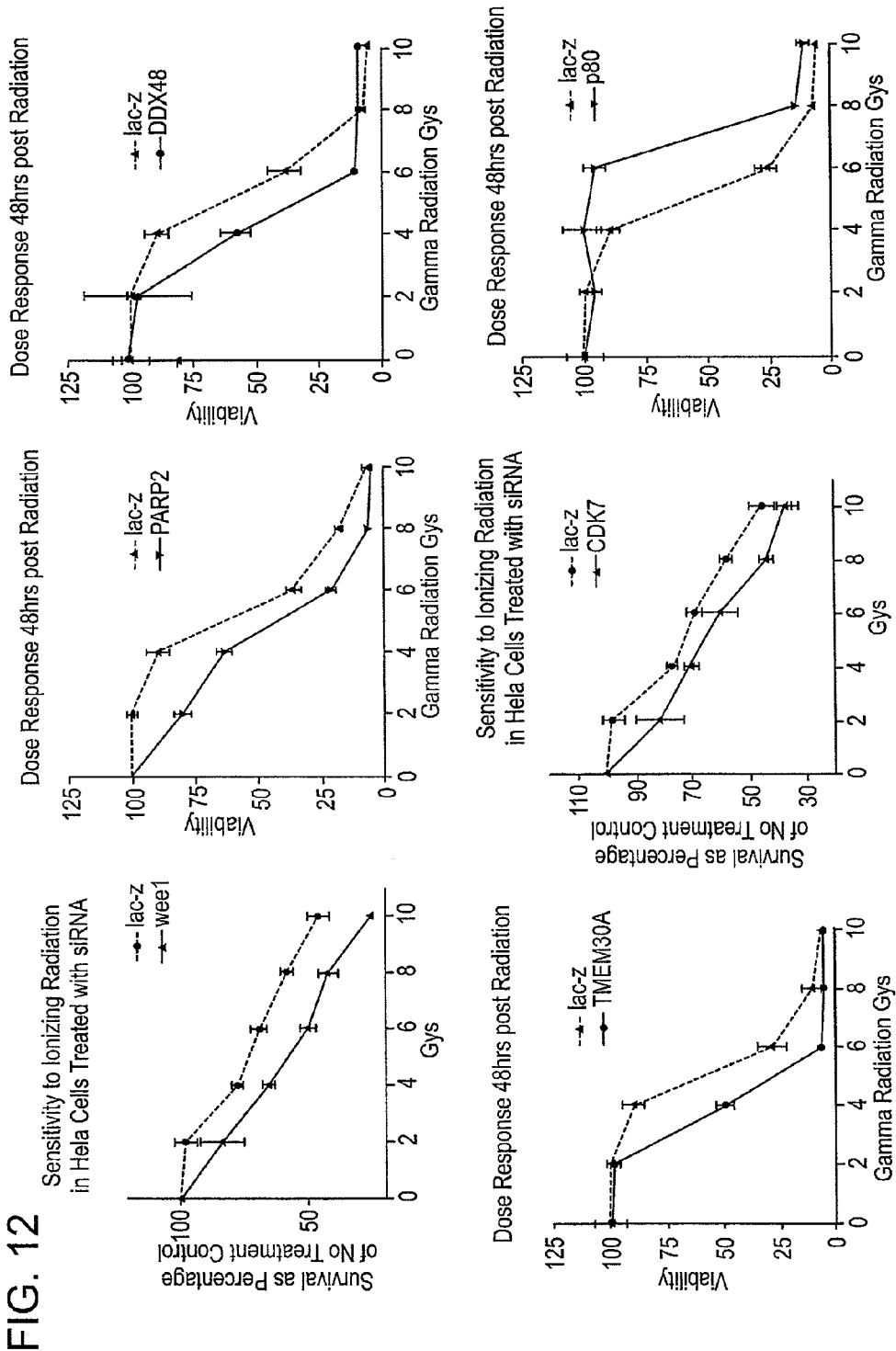
FIG. 12 shows the percent cell survival of HeLa cells at 48 hours following exposure to the indicated doses of gamma radiation. The cells were treated with siRNA directed to either lacZ (control) or the indicated proteins (wee1, PARP2, DDX48, TMEM30A, CDK7, and UAF1). Only UAF1 siRNA enhanced cell survival compared to control.

HeLa cells were treated with siRNA directed to UAF1, wee1, PARP2, DDX48, TMEM30A, CDK7, or lacZ. The siRNA sequences were obtained from Qiagen DNA repair library set 2.0. The concentration used was 20 nanomolar, and the incubation period was 72 hours. HeLa cells were seeded in 96-well plates and irradiated with the indicated doses of γ-rays using a Gammacell 40 apparatus. As shown in FIG. 12, only the siRNA directed to UAF1 increased cell survival to gamma radiation.

Example 9

Use of USP1 Inhibitor to Increase Sensitivity of Ovarian Tumors to Anti-Neoplastic Agents in an Animal Model Human HRAS oncogene is introduced into immortalized human ovarian surface epithelial cells, which form subcutaneous tumors after injection into immunocompromised mice. (Liu et al., (2004) *Cancer Research* 64, 1655-1663). This model is used to test the efficacy of USP1 inhibitors in sensitizing ovarian tumors to anti-neoplastic agents. Six mice are used per group. To test the efficacy of cisplatin, alone or in combination with the USP1 inhibitor alstemaullone, the following groups are used:
  Group 1: treated with control vehicle
  Group 2: treated with cisplatin, 4 mg/kg;
  Group 3: treated with USP1 siRNA (SEQ ID NO:5), 50 µg in 1 ml RNase-free PBS, injected into the tail vein
  Group 4: treated with cisplatin, 4 mg/kg, and USP1 siRNA (SEQ ID NO:5), 50 µg in 1 ml RNase-free PBS. Repeat the cycle after two days.

All treatments are started a week after tumor inoculation. Mice are treated for 10 cycles in total, and sacrificed for tumor nodule counting two weeks (on day 50) after discontinuation of drug treatment. Upon sacrifice, antitumor activity in each group is evaluated by counting the number of tumor nodules in the peritoneal cavity, measuring the diameter of the tumors, measuring the volume of the ascites, and qualitatively observing the color of the peritoneal wall as an indication of the degree of tumor-induced vascularization. Toxicity is evaluated by qualitative observation of the general appearance and behavior of the mice prior to sacrifice and by measuring their body weight at various intervals during the course of the treatments.

Example 10

Screening for Inhibitors of USP1/UAF1 Deubiquitinase Activity

As described above, knockdown of USP1 activity, by siRNA knockdown of USP1 protein levels, results in increased FANCD2-Ub and PCNA-Ub levels and increased DNA repair activity in the cell. This increase in DNA repair activity results in elevated cellular resistance to Ionizing Radiation. Recent data also showed that USP1 remains associated with a binding partner Ubiquitin Associated Factor 1(UAF1, Example 1). Together, USP1/UAF1 protein complex serves as an excellent target for high throughput screening to identify small molecule inhibitors as radioprotective agents. A baculovirus mediated SF9 insect cell expression method has been developed for both USP1 and UAF1. The expressed proteins are purified by affinity, ion exchange and gel filtration chromatography. Briefly, a baculovirus for USP1 and UAF1 was generated using the Bac-to-Bac baculovirus expression system (Invitrogen, CA). Full length USP1 contains an auto cleavage site at residue 670 -671, where cleavage occurs at GG after a Ubiquitin like motif (Huang, T. T., and D'Andrea, A. D. (2006). HAUSP hunting the FOX(O). *Nat Cell Biol* 8, 1043-1045). In order to purify the intact full length protein, two Glycine residues were mutated to Alanines using site directed mutagenesis (Stratagene). This modified full length USP1 clone was PCR amplified and subcloned into pFastBac-HT vectors (Invitrogen, CA) with N-terminal His tag. USP1 Associated Factor 1 (UAF1) was also cloned into pFastBac vector, but without the N-terminal His tag. The clones were PCR verified and transformed into DH10Bac cells for blue-white colony selection. Bacmid DNA from the re-confirmed colony was extracted and presence of correct USP1 or UAF1 clones were confirmed by PCR amplification. The bacmid DNA were then transfected into SF9 cells using the Cellfectin reagent (Invitrogen, CA). P1 virus sets were collected following manufacturer's protocol and used to amplify P2 and P3 virus respectively. SF9 cells are co-infected with USP1 and UAF1 viruses to co-express these two proteins. A series of virus titer was used to optimize the expression level of USP1 and UAF1. Best expression of USP1 and UAF1 was observed with the virus titers of 1 µl in 2000 µl and 4000 µl of SF9 culture respectively. Expression level of these proteins at various time points after infection was also tested to determine optimum time of expression. Best expression was achieved at 60 hours after infection. Finally, SF9 suspension culture was infected at cell density 1.8 million/ml and grown at 28° C. on orbital shaker for 60 hours. After expression, cells are harvested at 500 g for 7 minutes, washed with 1× PBS, centrifuged again and stored at −80° C. for purification.

Figure 13:
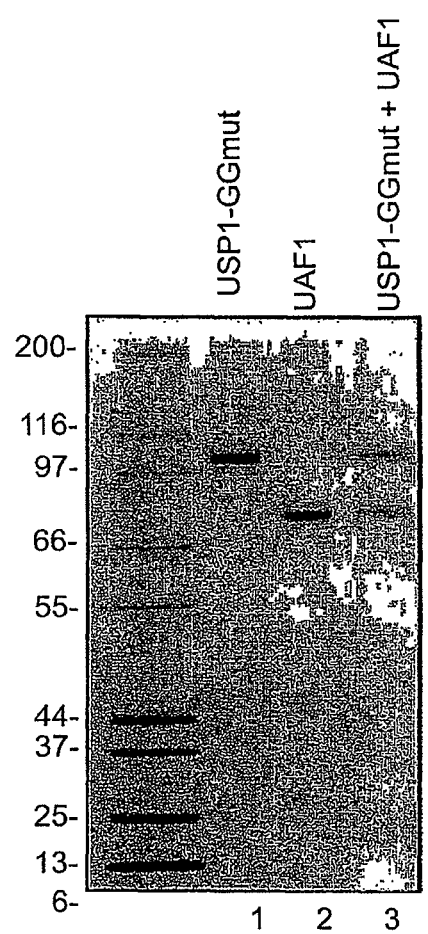
FIG. 13 represent the purification of USP1, UAF1 and USP1/UAF1 complex from SF9 cells co-infected with respective baculoviruses.

USP1 and UAF1 complex was initially purified by Ni-NTA affinity purification. SF9 cells were resuspended in a pre-chilled lysis buffer containing 50 mM Tris pH 8.0, 200 mM NaCl, 10 mM Imidazole, 10 mM β-mercaptoethanol, 10% glycerol and 0.2% Triton X. After sonication, the cell lysate was centrifuged at 20000 r.p.m. for 45 minutes at 4° C. Ni-NTA resin equilibrated in the lysis buffer and added to the soluble supernatant from the whole cell lysate. 2-3 ml of resin is added to per 2 liter of SF9 culture. The resin was incubated with mixing for 1 hour at 4° C. and Spin down resin at 500×g for 5 min. After carefully removing the supernatant, the Ni_NTA resin was re-suspend in lysis buffer to wash out any unbound proteins. After spinning down the resin again, it was resuspended in wash bufferl containing 50 mM Tris pH 8.0, 150 mM NaCl, 20 mM Imidazole, 10 mM β-mercaptoethanol, 10% glycerol and 1% Triton X. After spinning down the resin again, it was washed by wash buffers containing 50 mM Tris pH 8.0, 1000 mM NaCl, 20 mM Imidazole, 10 mM β-mercaptoethanol, 10% glycerol two times followed by a final wash with the buffer containing 50 mM Tris pH 8.0, 100 mM NaCl, 20 mM Imidazole, 10 mM β-mercaptoethanol, 10% glycerol. The bound USP1/UAF1 complex was eluted slowly from the column by elution buffer containing 50 mM Tris pH 8.0, 100 mM NaCl, 250 mM Imidazole, 10 mM β-mercaptoethanol and 10% glycerol. At this stage, eluted USP1/UAF1 complex was further purified by ion exchange chromatography using Q-sepharose column. The purified protein complex was further purified by gel filtration using S-200 column. Final buffer to be used in gel filtration column contained 50 mM Tris pH 8.0, 100 Mm KCl, 5 mM DTT and 0.1 mM EDTA. After final purification, quality of the protein was checked by SDS-PAGE and coomassie blue staining (FIG. 13). Finally USP1/UAF1 concentration was measured by Bradford assay (BioRad, CA). 11 mg of protein complex were purified from 2 liter SF9 culture at a final concentration of 0.77 mg/ml. FIG. 13 represent the purification of USP1, UAF1 and USP1/UAF1 complex from SF9 cells co-infected with respective baculoviruses.

In order to develop a highly sensitive assay with easy readout for high throughput detection, the fluorogenic compound Ubiquitin-7-amido-4-methylcoumarin (Ub-AMC, Boston Biochem) was used as a substrate for USP1/UAF1 enzyme complex. USP1 catalyzes the cleavage of Ubiquitin-AMC, releasing free AMC moiety, which leads to increase in fluorescence emission at 460 nm ($\lambda_{ex}$=380 nm) (Dang, L. C., Melandri, F. D., and Stein, R. L. (1998). Kinetic and mechanistic studies on the hydrolysis of ubiquitin C-terminal 7-amido-4-methylcoumarin by deubiquitinating enzymes. *Biochemistry* 37, 1868-1879). Catalytic activity towards Ub-AMC increases 35 fold compared to USP1 enzyme alone. Initial enzyme assay development was performed in 96 well plates with 100 µl reaction volume containing 20 mM HEPES-KOH, 0.1 mg/ml ovalbumin (Sigma), 0.5 mM EDTA and 10 mM DTT. 2.5 nM USP1/UAF1 enzyme complex was mixed with the reaction buffer, incubated at 37° C. for 10 minutes and the 0.3 µM Ub-AMC was added. Fluorescence was measured using a Fluostar Galaxy Fluorometer (BMG Labtech Inc.). Ubiquitin aldehyde is a potent covalent inhibitor of deubiquitinating enzymes, and inhibits the enzyme, by covalently attaching to the active site. There is a sharp decrease in enzyme activity upon incubation of USP1/UAF1 complex with 25 nM of Ub-Al. The significant decrease in signal upon Ub-Al can easily be detected in high throughput data collection and data interpretation. Hence, Ub-Al can be used as positive control for inhibition in high throughput screening and any potential inhibition signal can be compared to this control, wherein a significant decrease of fluorescence signal comparable to that of Ubiquitin aldehyde will be treated as positive hits.

Figure 14B:
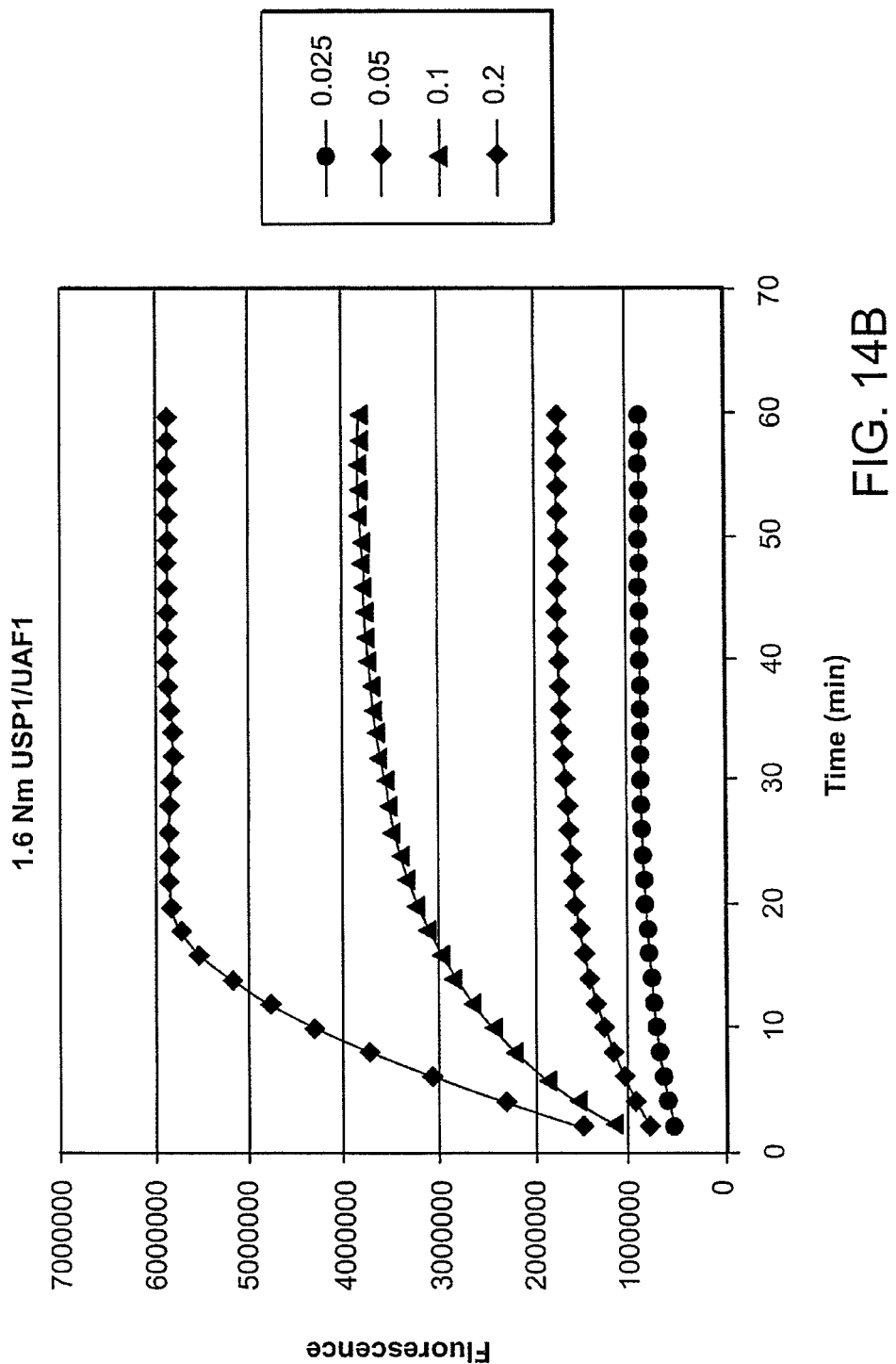
FIG. 14B shows a fluorescence reading of the 1.6 nM USP1/UAF1 set with different Ub-AMC concentrations.

Once the preliminary enzyme assay was established in 96 well format, it was optimized for 384 wells for high throughput screening of inhibitors. The major points to be considered were the volume of the reaction and amount of Ub-AMC substrate to be used in the assay. Since the price of Ub-AMC is very high, in order to make it a feasible assay for HTS, lowest workable amount of the AMC conjugate was used. Reaction volume was minimized to 30 µl in order to meet the recommendation of ICCB-L screening facility (Harvard). In the preliminary optimization experiment, a series of pilot experiments were performed with varying Ub-AMC concentrations (0.025 µM to 0.2 µM), along with the varying concentration of USP1/UAF1 complex (0.2 nM-3.2 nM, FIG. 14). This concentration grid was performed in 384 well plates (Corning, 3711) using the automated liquid handler present at ICCB-L screening facility. After incubating the enzyme and buffer at 37° C. for 10 minutes, Ub-AMC was added and fluorescence emission at 460 nm ($\lambda_{ex}$=380 nm) was measured in an automated plate reader Envision 2 (Perkin Elmer). Fluorescence reading for all time points up to one hour was noted and the data for different Ub-AMC concentration range was plotted with each USP1/UAF1 enzyme complex concentration (FIG. 14). Comparison of fluorescence emission in each sets shows that the minimum optimal Ub-Amc concentration required with optimum USP1/UAF1 concentration to obtain significant increase in signal compared to the baseline. Based on the results, 0.1 µM Ub-AMC concentration along with 1.6 nM USP1/UAF1 concentration produced significantly increased signal from the baseline and these optimum concentrations were and should be used for HTS. So by this optimization Ub-AMC concentration was reduced 3 times (0.3 µM to 0.1 µM) and volume of the reaction was reduced 3.33 times (100 µl to 30 µl). Taken together the overall use of the substrate was reduced 10 times by doing this optimization (3×3.33). Unlike single enzyme assay, only one time point can be collected in HTS with thousands of compound screen. This optimization step also shows the desirable time point to read fluorescence signal is 15 minutes after addition of Ub-AMC, as this is before the reaction reaches the saturation.

Scale Up for High Throughput Screening

After large scale expression-purification of USP1/UAF1 protein complex, the high throughput screening will be performed. Buffers and USP1/UAF1 complex were added into the 384 well plate (Corning, black 3711) using automated liquid handling robot-Bio-Tek Microfill (Bio-Tek Instruments Inc., VT). This was followed by addition of compounds to the plate wells using pin transfer robotic system. This includes a custom designed Seiko Cartesian robot with pin arrays (V & P Scientific Inc.) and Zymark Twister II robotic arm to stack and transfer compound plates and assay plates. In this step, 100 nL of the compounds (in DMSO) from compound library plates was added to the 384 well assay plates. After incubating the assay plates at 37° C. for 10 minutes desired volume of Ub-Amc was added by the automated liquid handler. Finally fluorescence emission at 460 nm ($\lambda_{ex}$=380 nm) was measured in an automated plate reader Envision 2 (Perkin Elmer, MA). The Z' factor for the assay was calculated (Zhang, J.-H., Chung, T. D. Y., and Oldenburg, K. R. (1999). A simple statistical parameter for use in evaluation and validation of high throughput screening assays. *J. Biomol. Screen* 4, 67-73) and if required, the assay was further optimized until Z'>0.5.

The HTS assay was run using the ICCB-L Biomol bioactive library (Harvard Medical School, Boston, Mass.).

ICCB-L has a collection of over 150,000 compounds in their compound library, which consists of known bioactive libraries, natural product libraries, and commercial libraries such as ChemDiv, ChemBridge etc. Known bioactive libraries containing Biomol ICCB known bioactives, NINDS and Prestwick collections were tested first for potential inhibitors. This set of the library contains many FDA approved drugs and the compounds are known to exhibit low toxicity and high cellular retention, making them excellent targets for further cell based assay. The reactions were performed using automated instruments as described above. Among the two bioactive library tested, three compounds, β-Lapachone, Biomol AP401 and RK-682 showed substantial low fluorescence signal in the range of Ub-Al treated positive control sets. These three compounds thus can serve as potential inhibitors and candidates for further secondary screening. Also, identification of these compounds by high throughput screening shows the validity of the experimental setup and suggests that this assay now can be used to screen 40,000 compounds.

Example 12

Secondary and Tertiary Screening

Hits from the primary screening will be analyzed further in the secondary screening. Expected number hits in the primary high throughput screen typically are in the range of 0.5%. In this step, the compounds will be re-tested for inhibition using the Ub-AMC in vitro enzyme assay. After reconfirming inhibition, different concentration range of the inhibitors will be tested to show dose dependency of inhibition and IC50 calculation. The final hits will be further grouped into different structural class to look for presence of any particular structural group.

Best hits from the secondary screening will be tested for specificity towards USP1/UAF1. Other deubiquitinating enzymes will be tested for inhibition using the Ub-AMC activity assay. For this purpose USP7, USP2, Isopeptidase T, Ubiquitin C-terminal hydrolase 1 (UCH-L1) will be tested first as these enzymes have been expressed and purified in other laboratories (Hu et al. (2002). Crystal structure of a UBP-family deubiquitinating enzyme in isolation and in complex with ubiquitin aldehyde. Cell 111, 1041-1054; Luchansky, et al. (2006). Substrate recognition and catalysis by UCH-L1. *Biochemistry* 45, 14717-14725; Renatus et al. (2006). Structural basis of ubiquitin recognition by the deubiquitinating protease USP2. *Structure* 14, 1293-1302).

These hits will then be used in cell based assay to look for USP1 inhibition in vivo using levels of FANCD2-Ub and PCNA-Ub as biomarker for inhibition. For the cell based assay, cells will be treated with the potential compounds and levels of monoubiquitinated FANCD2 and PCNA will be tested both with or without DNA damage. Expected readout of USP1 inhibition will be high level of endogenous monoubiquitinated FANCD2 and PCNA without the DNA damage and this will be persistent long after DNA damage as well. For this assay HeLa and HEK293T cells will be treated with these compounds and grown in Dulbecco's modified Eagle's medium supplemented with 15% heat-inactivated fetal calf serum in a humidified 5% $CO_2$ incubator at 37° C. Damage will be induced by both. UV irradiation using Stratalinker (Stratagene) and treatment with Mitomycin C (MMC, Sigma). After cell lysis, levels of monoubiquitinated FANCD2 and PCNA in whole cell lysate will be tested by immunoblotting with anti-FANCD2 antibody (FI-17) (Santa Cruz Biotechnology) and anti-PCNA antibody (ref). Protection from Chromosome aberrations will also be tested in UV/MMC damaged cells treated with potential USP1 inhibitors using standard chromosome breakage assay (Yang et al., 2001).

Potential inhibitors of USP1/UAF1 complex can inhibit the deubiquitinating activity by a number of different mechanisms. Crystal structures of USP7 and USP2 showed that ubiquitin binds to the enzyme via hydrogen bonding interactions with water molecules present in some specific pockets in enzyme. So inhibition may occur due to binding of the inhibitor in these water-binding pockets far away from the enzyme active sites. Also, UAF1 binding enhances USP1 enzyme activity by several folds suggesting a probable conformational change in USP1 after UAF1 binding may lead to an efficient conformation for catalysis. Inhibitor may also bind to such an allosteric site and may prevent the catalytically efficient conformational switch. These mechanisms of action will be tested by using a small substrate Gly-Gly-AMC (Boston Biochem, MA) instead of large ubiquitin conjugated AMC. If the compound is active site inhibitor, then it will fail to cleave Gly-Gly-AMC, but if the small inhibitor binds to a site away from the active site, then the enzyme will be fully active with Gly-Gly-AMC but not with Ub-AMC. Also, standard enzyme assays will be carried out to determine competitive or non-competitive nature of inhibition.

The invention claimed is:

1. An in vitro, biochemical method of identifying an inhibitor of ubiquitin specific protease 1(USP1) comprising:

(i) contacting an isolated USP1 with a test compound in the presence of monoubiquitinated proliferating cell nuclear antigen (PCNA) or ubiquitin-7-amido-4-methylcoumarin, wherein said USP1 is selected from the group consisting of SEQ ID NO: 3 or the polypeptide set forth by amino acids 17-785 of SEQ ID NO: 3, and wherein said PCNA comprises SEQ ID NO: 2; and (ii) detecting the deubiquitination of said PCNA or ubiquitin-7-amido-4-methylcoumarin using an antibody or fluorescence, wherein a decrease in the deubiquitination of said PCNA or ubiquitin-7-amido-4-methylcoumarin in the presence of the test compound, relative to the absence of the test compound, identifies said test compound as an inhibitor of USP1.

2. The method of claim 1, wherein USP1 is present in a heterodimeric complex with human USP1 associated factor 1 (UAF1).

3. An in vitro, biochemical method of identifying an inhibitor of USP1 comprising:

(i) contacting a composition comprising isolated USP1 and isolated human UAF1 with a test compound in the presence of ubiquitin-7-amido-4-methylcoumarin, wherein said USP1 is selected from the group consisting of SEQ ID NO: 3 or the polypeptide set forth by amino acids 17-785 of SEQ ID NO: 3, and (ii) detecting the deubiquitination of said ubiquitin-7-amido-4- methylcoumarin using fluorescence, wherein a decrease in the deubiquitination of said ubiquitin-7-amido-4- methylcoumarin in the presence of the test compound, relative to the absence of the test compound, identifies said test compound as an inhibitor of USP1.

4. The method of claim 3, wherein said method is adapted to a high throughput screen.

* * * * *